(12) United States Patent
Sturmer et al.

(10) Patent No.: US 9,492,822 B2
(45) Date of Patent: *Nov. 15, 2016

(54) MICROFLUIDIC FEEDBACK USING IMPEDANCE DETECTION

(71) Applicant: ADVANCED LIQUID LOGIC, INC., San Diego, CA (US)

(72) Inventors: Ryan A. Sturmer, Durham, NC (US); Vijay Srinivasan, Cary, NC (US); Arjun Sudarsan, Carlsbad, CA (US)

(73) Assignee: Advanced Liquid Logic, Inc., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/942,125

(22) Filed: Nov. 16, 2015

(65) Prior Publication Data

US 2016/0074863 A1 Mar. 17, 2016

Related U.S. Application Data

(63) Continuation of application No. 14/116,553, filed as application No. PCT/US2012/036949 on May 8, 2012, now Pat. No. 9,188,615.

(60) Provisional application No. 61/483,827, filed on May 9, 2011.

(51) Int. Cl.
*G01R 27/16* (2006.01)
*B01L 3/00* (2006.01)
*G01N 27/04* (2006.01)

(52) U.S. Cl.
CPC ...... *B01L 3/50273* (2013.01); *B01L 3/502792* (2013.01); *G01N 27/048* (2013.01);
(Continued)

(58) Field of Classification Search
CPC .. G01N 27/22; G01N 27/223; G01N 27/227; G01N 13/00; G01R 27/16; B01L 3/502
See application file for complete search history.

(56) References Cited

U.S. PATENT DOCUMENTS

| 4,127,460 A | 11/1978 | Gaske et al. |
| 4,244,693 A | 1/1981 | Guon |

(Continued)

FOREIGN PATENT DOCUMENTS

| JP | 2006078225 A | 3/2006 |
| JP | 2006317364 A | 11/2006 |

(Continued)

OTHER PUBLICATIONS

Benton et al., "Library Preparation Method 1 DNA Library Construction for Illumina SBS Sequencing Platforms using NEBNext® Library Preparation Reagents", Application Note, NuGEN, 2011.

(Continued)

*Primary Examiner* — Jennifer Dieterle
(74) *Attorney, Agent, or Firm* — Ward and Smith, P.A.; Ryan K. Simmons

(57) ABSTRACT

Methods comprising measuring the impedance of the electrode produced by the excitation signal, wherein the impedance indicates presence of liquid at the electrode are disclosed. Computer readable mediums storing processor executable instructions for performing the method, and systems are also disclosed. The systems comprise a processor, memory and code stored in the memory that when executed cause the processor at least to: receive an output voltage signal, superimpose an excitation signal onto the output voltage signal to produce a superimposed signal, connect the superimposed signal to an electrode in a droplet actuator, suppress the output voltage signal, when detecting an impedance of the electrode, and measure the impedance of the electrode produced by the excitation signal, wherein the impedance indicates presence of liquid at the electrode.

51 Claims, 25 Drawing Sheets

(52) U.S. Cl.
CPC ...... *G01R 27/16* (2013.01); *B01L 2200/0621* (2013.01); *B01L 2200/10* (2013.01); *B01L 2200/14* (2013.01); *B01L 2200/16* (2013.01); *B01L 2300/0645* (2013.01); *B01L 2300/087* (2013.01); *B01L 2300/089* (2013.01); *B01L 2300/0816* (2013.01); *B01L 2300/0829* (2013.01); *B01L 2400/0427* (2013.01)

(56) References Cited

U.S. PATENT DOCUMENTS

| | | |
|---|---|---|
| 4,636,785 A | 1/1987 | Le Pesant |
| 4,748,390 A | 5/1988 | Okushima et al. |
| 4,829,833 A | 5/1989 | Feller et al. |
| 4,936,828 A | 6/1990 | Chiang |
| 5,038,852 A | 8/1991 | Johnson et al. |
| 5,176,203 A | 1/1993 | Larzul |
| 5,181,016 A | 1/1993 | Lee et al. |
| 5,225,332 A | 7/1993 | Weaver et al. |
| 5,266,498 A | 11/1993 | Tarcha et al. |
| 5,455,008 A | 10/1995 | Earley et al. |
| 5,472,881 A | 12/1995 | Beebe et al. |
| 5,486,337 A | 1/1996 | Ohkawa et al. |
| 5,498,392 A | 3/1996 | Wilding et al. |
| 5,720,923 A | 2/1998 | Haff et al. |
| 5,779,977 A | 7/1998 | Haff et al. |
| 5,817,526 A | 10/1998 | Kinoshita et al. |
| 5,827,480 A | 10/1998 | Haff et al. |
| 5,945,281 A | 8/1999 | Prabhu et al. |
| 5,998,224 A | 12/1999 | Rohr et al. |
| 6,013,531 A | 1/2000 | Wang et al. |
| 6,033,880 A | 3/2000 | Haff et al. |
| 6,063,339 A | 5/2000 | Tisone et al. |
| 6,078,384 A | 6/2000 | Dammann et al. |
| 6,130,098 A | 10/2000 | Handique et al. |
| 6,152,181 A | 11/2000 | Wapner et al. |
| 6,180,372 B1 | 1/2001 | Franzen |
| 6,294,063 B1 | 9/2001 | Becker et al. |
| 6,319,668 B1 | 11/2001 | Nova et al. |
| 6,379,929 B1 | 4/2002 | Burns et al. |
| 6,432,290 B1 | 8/2002 | Harrison et al. |
| 6,453,928 B1 | 9/2002 | Kaplan et al. |
| 6,461,570 B2 | 10/2002 | Ishihara et al. |
| 6,548,311 B1 | 4/2003 | Knoll |
| 6,565,727 B1 | 5/2003 | Shenderov |
| 6,632,655 B1 | 10/2003 | Mehta et al. |
| 6,673,533 B1 | 1/2004 | Wohlstadter et al. |
| 6,734,436 B2 | 5/2004 | Faris et al. |
| 6,773,566 B2 | 8/2004 | Shenderov |
| 6,790,011 B1 | 9/2004 | Le Pesant et al. |
| 6,841,128 B2 | 1/2005 | Kambara et al. |
| 6,846,638 B2 | 1/2005 | Shipwash |
| 6,911,132 B2 | 6/2005 | Pamula et al. |
| 6,924,792 B1 | 8/2005 | Jessop |
| 6,955,881 B2 | 10/2005 | Tanaami |
| 6,977,033 B2 | 12/2005 | Becker et al. |
| 6,989,234 B2 | 1/2006 | Kolar et al. |
| 6,995,024 B2 | 2/2006 | Smith et al. |
| 7,052,244 B2 | 5/2006 | Fouillet et al. |
| 7,148,683 B2 | 12/2006 | Xiang et al. |
| 7,163,612 B2 | 1/2007 | Sterling et al. |
| 7,211,223 B2 | 5/2007 | Fouillet et al. |
| 7,211,442 B2 | 5/2007 | Gilbert et al. |
| 7,255,780 B2 | 8/2007 | Shenderov |
| 7,267,752 B2 | 9/2007 | King et al. |
| 7,300,131 B2 | 11/2007 | Sakagami et al. |
| 7,328,979 B2 | 2/2008 | Decre et al. |
| 7,329,545 B2 | 2/2008 | Pamula et al. |
| 7,438,860 B2 | 10/2008 | Takagi et al. |
| 7,439,014 B2 | 10/2008 | Pamula et al. |
| 7,439,072 B2 | 10/2008 | Shvets et al. |
| 7,458,661 B2 | 12/2008 | Kim et al. |
| 7,495,031 B2 | 2/2009 | Sakuma et al. |
| 7,531,072 B2 | 5/2009 | Roux et al. |
| 7,547,380 B2 | 6/2009 | Velev |
| 7,556,776 B2 | 7/2009 | Fraden et al. |
| 7,569,129 B2 | 8/2009 | Pamula et al. |
| 7,579,172 B2 | 8/2009 | Cho et al. |
| 7,641,779 B2 | 1/2010 | Becker et al. |
| 7,727,466 B2 | 6/2010 | Meathrel et al. |
| 7,727,723 B2 | 6/2010 | Pollack et al. |
| 7,759,132 B2 | 7/2010 | Pollack et al. |
| 7,763,471 B2 | 7/2010 | Pamula et al. |
| 7,767,147 B2 | 8/2010 | Adachi et al. |
| 7,767,435 B2 | 8/2010 | Chiu et al. |
| 7,815,871 B2 | 10/2010 | Pamula et al. |
| 7,816,121 B2 | 10/2010 | Pollack et al. |
| 7,822,510 B2 | 10/2010 | Paik et al. |
| 7,851,184 B2 | 12/2010 | Pollack et al. |
| 7,875,160 B2 | 1/2011 | Jary |
| 7,901,947 B2 | 3/2011 | Pollack et al. |
| 7,919,330 B2 | 4/2011 | De Guzman et al. |
| 7,922,886 B2 | 4/2011 | Fouillet et al. |
| 7,939,021 B2 | 5/2011 | Smith et al. |
| 7,943,030 B2 | 5/2011 | Shenderov |
| 7,989,056 B2 | 8/2011 | Plissonier et al. |
| 7,998,436 B2 | 8/2011 | Pollack |
| 8,007,739 B2 | 8/2011 | Pollack et al. |
| 8,035,949 B2 | 10/2011 | Miyano et al. |
| 8,041,463 B2 | 10/2011 | Pollack et al. |
| 8,048,628 B2 | 11/2011 | Pollack et al. |
| 8,075,754 B2 | 12/2011 | Sauter-Starace et al. |
| 8,088,578 B2 | 1/2012 | Hua et al. |
| 8,093,062 B2 | 1/2012 | Winger et al. |
| 8,093,064 B2 | 1/2012 | Shah et al. |
| 8,137,917 B2 | 3/2012 | Pollack et al. |
| 8,147,668 B2 | 4/2012 | Pollack et al. |
| 8,179,216 B2 | 5/2012 | Knospe |
| 8,202,686 B2 | 6/2012 | Pamula et al. |
| 8,208,146 B2 | 6/2012 | Srinivasan et al. |
| 8,221,605 B2 | 7/2012 | Pollack et al. |
| 8,236,156 B2 | 8/2012 | Sarrut et al. |
| 8,268,246 B2 | 9/2012 | Srinivasan et al. |
| 8,287,711 B2 | 10/2012 | Pollack et al. |
| 8,292,798 B2 | 10/2012 | Califorrniaa |
| 8,304,253 B2 | 11/2012 | Yi et al. |
| 8,313,698 B2 | 11/2012 | Pollack et al. |
| 8,317,990 B2 | 11/2012 | Pamula et al. |
| 8,337,778 B2 | 12/2012 | Stone et al. |
| 8,342,207 B2 | 1/2013 | Raccurt et al. |
| 8,349,276 B2 | 1/2013 | Pamula et al. |
| 8,364,315 B2 | 1/2013 | Sturmer et al. |
| 8,388,909 B2 | 3/2013 | Pollack et al. |
| 8,389,297 B2 | 3/2013 | Pamula et al. |
| 8,394,249 B2 | 3/2013 | Pollack et al. |
| 8,394,641 B2 | 3/2013 | Winger |
| 8,426,213 B2 | 4/2013 | Eckhardt et al. |
| 8,440,392 B2 | 5/2013 | Pamula et al. |
| 8,444,836 B2 | 5/2013 | Fouillet et al. |
| 8,872,527 B2 | 10/2014 | Sturmer et al. |
| 2002/0001544 A1 | 1/2002 | Hess et al. |
| 2002/0005354 A1 | 1/2002 | Spence et al. |
| 2002/0036139 A1 | 3/2002 | Becker et al. |
| 2002/0043463 A1 | 4/2002 | Shenderov |
| 2002/0058332 A1 | 5/2002 | Quake et al. |
| 2002/0143437 A1 | 10/2002 | Handique et al. |
| 2003/0007898 A1 | 1/2003 | Bohm et al. |
| 2003/0049177 A1 | 3/2003 | Smith et al. |
| 2003/0071639 A1 | 4/2003 | Haag et al. |
| 2003/0132538 A1 | 7/2003 | Chandler |
| 2003/0164295 A1 | 9/2003 | Sterling |
| 2003/0183525 A1 | 10/2003 | Elrod et al. |
| 2003/0184316 A1 | 10/2003 | Yamagishi et al. |
| 2003/0205632 A1 | 11/2003 | Kim et al. |
| 2004/0027405 A1 | 2/2004 | Stoessel et al. |
| 2004/0031688 A1 | 2/2004 | Shenderov |
| 2004/0055871 A1 | 3/2004 | Walton et al. |
| 2004/0055891 A1 | 3/2004 | Pamula et al. |
| 2004/0058450 A1 | 3/2004 | Pamula et al. |
| 2004/0086870 A1 | 5/2004 | Tyvoll et al. |
| 2004/0101445 A1 | 5/2004 | Shvets et al. |
| 2004/0118201 A1 | 6/2004 | Gerhardt et al. |
| 2004/0170530 A1 | 9/2004 | Hefti et al. |
| 2004/0180346 A1 | 9/2004 | Anderson et al. |
| 2004/0209376 A1 | 10/2004 | Natan et al. |

(56) References Cited

U.S. PATENT DOCUMENTS

| | | |
|---|---|---|
| 2004/0231987 A1 | 11/2004 | Sterling et al. |
| 2005/0118574 A1 | 6/2005 | Chandler et al. |
| 2005/0179746 A1 | 8/2005 | Roux et al. |
| 2005/0189049 A1 | 9/2005 | Ohno et al. |
| 2005/0227349 A1 | 10/2005 | Kim et al. |
| 2005/0260686 A1 | 11/2005 | Watkins et al. |
| 2005/0277197 A1 | 12/2005 | Chandler et al. |
| 2005/0282224 A1 | 12/2005 | Fouillet et al. |
| 2006/0021875 A1 | 2/2006 | Griffith et al. |
| 2006/0039823 A1 | 2/2006 | Yamakawa et al. |
| 2006/0040375 A1 | 2/2006 | Arney et al. |
| 2006/0054503 A1 | 3/2006 | Pamula et al. |
| 2006/0102477 A1 | 5/2006 | Vann et al. |
| 2006/0114296 A1 | 6/2006 | Gascoyne et al. |
| 2006/0159962 A1 | 7/2006 | Chandler et al. |
| 2006/0164490 A1 | 7/2006 | Kim et al. |
| 2006/0194331 A1 | 8/2006 | Pamula et al. |
| 2006/0210443 A1 | 9/2006 | Stearns et al. |
| 2006/0231398 A1 | 10/2006 | Sarrut et al. |
| 2006/0254933 A1 | 11/2006 | Adachi et al. |
| 2006/0286549 A1 | 12/2006 | Sohn et al. |
| 2007/0015289 A1 | 1/2007 | Kao et al. |
| 2007/0019041 A1 | 1/2007 | Mataki |
| 2007/0023292 A1 | 2/2007 | Kim et al. |
| 2007/0037294 A1 | 2/2007 | Pamula et al. |
| 2007/0045117 A1 | 3/2007 | Pamula et al. |
| 2007/0064990 A1 | 3/2007 | Roth |
| 2007/0075922 A1 | 4/2007 | Jessop |
| 2007/0086927 A1 | 4/2007 | Natarajan et al. |
| 2007/0179641 A1 | 8/2007 | Lucas et al. |
| 2007/0202538 A1 | 8/2007 | Glezer et al. |
| 2007/0207513 A1 | 9/2007 | Sorensen et al. |
| 2007/0217956 A1 | 9/2007 | Pamula et al. |
| 2007/0241068 A1 | 10/2007 | Pamula et al. |
| 2007/0242105 A1 | 10/2007 | Srinivasan et al. |
| 2007/0242111 A1 | 10/2007 | Pamula et al. |
| 2007/0243634 A1 | 10/2007 | Pamula et al. |
| 2007/0267294 A1 | 11/2007 | Shenderov |
| 2007/0275415 A1 | 11/2007 | Srinivasan et al. |
| 2008/0003142 A1 | 1/2008 | Link et al. |
| 2008/0003588 A1 | 1/2008 | Hasson et al. |
| 2008/0006535 A1 | 1/2008 | Paik et al. |
| 2008/0023330 A1 | 1/2008 | Viovy |
| 2008/0038810 A1 | 2/2008 | Pollack et al. |
| 2008/0044893 A1 | 2/2008 | Pollack et al. |
| 2008/0044914 A1 | 2/2008 | Pamula et al. |
| 2008/0050834 A1 | 2/2008 | Pamula et al. |
| 2008/0053205 A1 | 3/2008 | Pollack et al. |
| 2008/0086183 A1 | 4/2008 | Greenberg et al. |
| 2008/0105549 A1 | 5/2008 | Pamela et al. |
| 2008/0113081 A1 | 5/2008 | Hossainy et al. |
| 2008/0124252 A1 | 5/2008 | Marchand et al. |
| 2008/0142376 A1 | 6/2008 | Fouillet et al. |
| 2008/0151240 A1 | 6/2008 | Roth |
| 2008/0166793 A1 | 7/2008 | Beer et al. |
| 2008/0210558 A1 | 9/2008 | Sauter-Starace et al. |
| 2008/0221215 A1 | 9/2008 | Summers et al. |
| 2008/0231291 A1 | 9/2008 | Ramsey et al. |
| 2008/0247920 A1 | 10/2008 | Pollack et al. |
| 2008/0264797 A1 | 10/2008 | Pamula et al. |
| 2008/0274513 A1 | 11/2008 | Shenderov et al. |
| 2008/0281471 A1 | 11/2008 | Smith et al. |
| 2008/0283414 A1 | 11/2008 | Monroe et al. |
| 2008/0302431 A1 | 12/2008 | Marchand et al. |
| 2008/0305481 A1 | 12/2008 | Whitman et al. |
| 2009/0014394 A1 | 1/2009 | Yi et al. |
| 2009/0042319 A1 | 2/2009 | De Guzman et al. |
| 2009/0053726 A1 | 2/2009 | Owen et al. |
| 2009/0127123 A1 | 5/2009 | Raccurt et al. |
| 2009/0134027 A1 | 5/2009 | Jary |
| 2009/0142564 A1 | 6/2009 | Plissonnier et al. |
| 2009/0155902 A1 | 6/2009 | Pollack et al. |
| 2009/0192044 A1 | 7/2009 | Fouillet |
| 2009/0225111 A1 | 9/2009 | Zapka et al. |
| 2009/0260988 A1 | 10/2009 | Pamula et al. |
| 2009/0263834 A1 | 10/2009 | Sista et al. |
| 2009/0280251 A1 | 11/2009 | De Guzman et al. |
| 2009/0280475 A1 | 11/2009 | Pollack et al. |
| 2009/0280476 A1 | 11/2009 | Srinivasan et al. |
| 2009/0283407 A1 | 11/2009 | Shah et al. |
| 2009/0288710 A1 | 11/2009 | Viovy et al. |
| 2009/0291433 A1 | 11/2009 | Pollack et al. |
| 2009/0304944 A1 | 12/2009 | Sudarsan et al. |
| 2009/0311713 A1 | 12/2009 | Pollack et al. |
| 2009/0321262 A1 | 12/2009 | Adachi et al. |
| 2010/0025242 A1 | 2/2010 | Pamula et al. |
| 2010/0025250 A1 | 2/2010 | Pamula et al. |
| 2010/0028920 A1 | 2/2010 | Eckhardt |
| 2010/0032293 A1 | 2/2010 | Pollack et al. |
| 2010/0041086 A1 | 2/2010 | Pamula et al. |
| 2010/0048410 A1 | 2/2010 | Shenderov et al. |
| 2010/0062508 A1 | 3/2010 | Pamula et al. |
| 2010/0068764 A1 | 3/2010 | Sista et al. |
| 2010/0084273 A1 | 4/2010 | Becker et al. |
| 2010/0087012 A1 | 4/2010 | Shenderov et al. |
| 2010/0096266 A1 | 4/2010 | Kim et al. |
| 2010/0116640 A1 | 5/2010 | Pamula et al. |
| 2010/0118307 A1 | 5/2010 | Srinivasan et al. |
| 2010/0120130 A1 | 5/2010 | Srinivasan et al. |
| 2010/0126860 A1 | 5/2010 | Srinivasan et al. |
| 2010/0130369 A1 | 5/2010 | Shenderov et al. |
| 2010/0140093 A1 | 6/2010 | Pamula et al. |
| 2010/0143963 A1 | 6/2010 | Pollack |
| 2010/0151439 A1 | 6/2010 | Pamula et al. |
| 2010/0181195 A1 | 7/2010 | Garcia Tello |
| 2010/0190263 A1 | 7/2010 | Srinivasan et al. |
| 2010/0194408 A1 | 8/2010 | Sturmer et al. |
| 2010/0221713 A1 | 9/2010 | Pollack et al. |
| 2010/0236927 A1 | 9/2010 | Pope et al. |
| 2010/0236928 A1 | 9/2010 | Srinivasan et al. |
| 2010/0236929 A1 | 9/2010 | Pollack et al. |
| 2010/0258441 A1 | 10/2010 | Sista et al. |
| 2010/0270156 A1 | 10/2010 | Srinivasan et al. |
| 2010/0279374 A1 | 11/2010 | Sista et al. |
| 2010/0282608 A1 | 11/2010 | Srinivasan et al. |
| 2010/0282609 A1 | 11/2010 | Pollack et al. |
| 2010/0291578 A1 | 11/2010 | Pollack et al. |
| 2010/0307917 A1 | 12/2010 | Srinivasan et al. |
| 2010/0320088 A1 | 12/2010 | Fouillet et al. |
| 2010/0323405 A1 | 12/2010 | Pollack et al. |
| 2011/0076692 A1 | 3/2011 | Sista et al. |
| 2011/0086377 A1 | 4/2011 | Thwar et al. |
| 2011/0091989 A1 | 4/2011 | Sista et al. |
| 2011/0097763 A1 | 4/2011 | Pollack et al. |
| 2011/0100823 A1 | 5/2011 | Pollack et al. |
| 2011/0104725 A1 | 5/2011 | Pamula et al. |
| 2011/0104747 A1 | 5/2011 | Pollack et al. |
| 2011/0104816 A1 | 5/2011 | Pollack et al. |
| 2011/0114490 A1 | 5/2011 | Pamula et al. |
| 2011/0118132 A1 | 5/2011 | Winger et al. |
| 2011/0147215 A1 | 6/2011 | Fuchs et al. |
| 2011/0180571 A1 | 7/2011 | Srinivasan et al. |
| 2011/0186433 A1 | 8/2011 | Pollack et al. |
| 2011/0203930 A1 | 8/2011 | Pamula et al. |
| 2011/0209998 A1 | 9/2011 | Shenderov |
| 2011/0213499 A1 | 9/2011 | Sturmer et al. |
| 2011/0303542 A1 | 12/2011 | Srinivasan et al. |
| 2011/0311980 A1 | 12/2011 | Pollack et al. |
| 2012/0018306 A1 | 1/2012 | Srinivasan et al. |
| 2012/0044299 A1 | 2/2012 | Winger |
| 2012/0132528 A1 | 5/2012 | Shenderov et al. |
| 2012/0136147 A1 | 5/2012 | Winger |
| 2012/0165238 A1 | 6/2012 | Pamula et al. |
| 2013/0017544 A1 | 1/2013 | Eckhardt et al. |
| 2013/0018611 A1 | 1/2013 | Sturmer |
| 2013/0059366 A1 | 3/2013 | Pollack et al. |
| 2013/0168250 A1 | 7/2013 | Fogleman et al. |
| 2013/0217113 A1 | 8/2013 | Srinivasan et al. |
| 2013/0217583 A1 | 8/2013 | Link et al. |
| 2013/0280131 A1 | 10/2013 | Handique et al. |
| 2013/0293246 A1 | 11/2013 | Pollack et al. |

(56) References Cited

U.S. PATENT DOCUMENTS

| | | | |
|---|---|---|---|
| 2014/0190830 A1 | 7/2014 | Sturmer et al. | |
| 2014/0332380 A1 | 11/2014 | Sturmer et al. | |

FOREIGN PATENT DOCUMENTS

| | | | |
|---|---|---|---|
| JP | 2006329899 A | | 12/2006 |
| JP | 2006329904 A | | 12/2006 |
| JP | 2008096590 A | | 4/2008 |
| WO | 0069565 | A1 | 11/2000 |
| WO | 0073655 | A1 | 12/2000 |
| WO | 02080822 | A2 | 10/2002 |
| WO | 2004011938 | A2 | 2/2004 |
| WO | 2004029585 | A1 | 4/2004 |
| WO | 2004030820 | | 4/2004 |
| WO | 2004073863 | A2 | 9/2004 |
| WO | 2005047696 | A1 | 5/2005 |
| WO | 2005069015 | A1 | 7/2005 |
| WO | 2006003292 | A1 | 1/2006 |
| WO | 2006013303 | A1 | 2/2006 |
| WO | 2006070162 | A1 | 7/2006 |
| WO | 2006081558 | | 8/2006 |
| WO | 2006085905 | A1 | 8/2006 |
| WO | 2006124458 | A2 | 11/2006 |
| WO | 2006127451 | A2 | 11/2006 |
| WO | 2006129486 | A1 | 12/2006 |
| WO | 2006132211 | A1 | 12/2006 |
| WO | 2006134307 | A1 | 12/2006 |
| WO | 2006138543 | | 12/2006 |
| WO | 2007003720 | A1 | 1/2007 |
| WO | 2007012638 | A1 | 2/2007 |
| WO | 2007033990 | A1 | 3/2007 |
| WO | 2007048111 | | 4/2007 |
| WO | 2007120240 | A2 | 10/2007 |
| WO | 2007120241 | A2 | 10/2007 |
| WO | 2007123908 | A2 | 11/2007 |
| WO | 2008051310 | A2 | 5/2008 |
| WO | 2008055256 | A3 | 5/2008 |
| WO | 2008068229 | A1 | 6/2008 |
| WO | 2008091848 | A2 | 7/2008 |
| WO | 2008098236 | A2 | 8/2008 |
| WO | 2008101194 | A2 | 8/2008 |
| WO | WO 2008/101194 | * | 8/2008 |
| WO | 2008106678 | A1 | 9/2008 |
| WO | 2008109664 | A1 | 9/2008 |
| WO | 2008112856 | A1 | 9/2008 |
| WO | 2008116209 | A1 | 9/2008 |
| WO | 2008116221 | A1 | 9/2008 |
| WO | 2008118831 | A2 | 10/2008 |
| WO | 2008124846 | A2 | 10/2008 |
| WO | 2008131420 | A2 | 10/2008 |
| WO | 2008134153 | A1 | 11/2008 |
| WO | 2009002920 | A1 | 12/2008 |
| WO | 2009003184 | A1 | 12/2008 |
| WO | 2009011952 | A1 | 1/2009 |
| WO | 2009021173 | A1 | 2/2009 |
| WO | 2009021233 | A2 | 2/2009 |
| WO | 2009026339 | A2 | 2/2009 |
| WO | 2009029561 | A2 | 3/2009 |
| WO | 2009032863 | A2 | 3/2009 |
| WO | 2009052095 | A1 | 4/2009 |
| WO | 2009052123 | A2 | 4/2009 |
| WO | 2009052321 | A2 | 4/2009 |
| WO | 2009052345 | A1 | 4/2009 |
| WO | 2009052348 | A2 | 4/2009 |
| WO | 2009076414 | | 6/2009 |
| WO | 2009086403 | A2 | 7/2009 |
| WO | 2009111769 | A2 | 9/2009 |
| WO | 2009135205 | A2 | 11/2009 |
| WO | 2009137415 | A2 | 11/2009 |
| WO | 2009140373 | A2 | 11/2009 |
| WO | 2009140671 | A2 | 11/2009 |
| WO | 2010004014 | A1 | 1/2010 |
| WO | 2010006166 | A2 | 1/2010 |
| WO | 2010009463 | A2 | 1/2010 |
| WO | 2010019782 | A2 | 2/2010 |
| WO | 2010027894 | A2 | 3/2010 |
| WO | 2010042637 | A2 | 4/2010 |
| WO | 2010077859 | A3 | 7/2010 |
| WO | 2011002957 | A2 | 1/2011 |
| WO | 2011020011 | A2 | 2/2011 |
| WO | 2011046615 | A2 | 4/2011 |
| WO | 2011057197 | A2 | 5/2011 |
| WO | 2011084703 | A2 | 7/2011 |
| WO | 2011126892 | A2 | 10/2011 |
| WO | 2012009320 | A2 | 1/2012 |
| WO | 2012012090 | A2 | 1/2012 |
| WO | 2012037308 | A2 | 3/2012 |
| WO | 2012068055 | A3 | 5/2012 |
| WO | 2013009927 | A3 | 1/2013 |

OTHER PUBLICATIONS

Boles et al., "Droplet-Based Pyrosequencing Using Digital Microfluidics", Analytical Chemistry, vol. 83, Sep. 2011, 8439-47.

Bottausci et al., "Fully Integrated EWOD Based Bio-Analysis Device", Labautomation 2011, Palm Springs Convention Center, Palm Springs, CA, USA; Abstract in Proceedings on line, poster distributed, Jan. 29-Feb. 2, 2011.

Burde et al., "Digital Microfluidic Rapid HIV Point-of-Care Diagnostic Device for Resource Limited Settings", Workshop on TB and HIV Diagnostics, Silver Spring, MD. (Poster, copies distributed to attendees.) http://www.blsmeetings.net/TB-HIV-DX-Wkshop/index.cfm, Jun. 28, 2011.

Burton et al., "Diagnosis of Fabry and Gaucher diseases from the Pilot Screening of Newborns for Lysosomal Storage Disorders in Illinois", APHL Newborn Screening and Genetic Testing Symposium, San Diego, 2011.

Chakrabarty, "Automated Design of Microfluidics-Based Biochips: connecting Biochemistry of Electronics CAD", IEEE International Conference on Computer Design, San Jose, CA, Oct. 1-4, 2006, 93-100.

Chakrabarty et al., "Design Automation Challenges for Microfluidics-Based Biochips", DTIP of MEMS & MOEMS, Montreux, Switzerland, Jun. 1-3, 2005.

Chakrabarty et al., "Design Automation for Microfluidics-Based Biochips", ACM Journal on Engineering Technologies in Computing Systems , 1(3), Oct. 2005, 186-223.

Chakrabarty, "Design, Testing, and Applications of Digital Microfluidics-Based Biochips", Proceedings of the 18th International Conf. on VLSI held jointly with 4th International Conf. on Embedded Systems Design (VLSID'05), IEEE, Jan. 3-7, 2005.

Chen et al., "Development of Mesoscale Actuator Device with Micro Interlocking Mechanism", J. Intelligent Material Systems and Structures, vol. 9, No. 4, Jun. 1998, pp. 449-457.

Chen et al., "Mesoscale Actuator Device with Micro Interlocking Mechanism", Proc. IEEE Micro Electro Mechanical Systems Workshop, Heidelberg, Germany, Jan. 1998, pp. 384-389.

Chen et al., "Mesoscale Actuator Device: Micro Interlocking Mechanism to Transfer Macro Load", Sensors and Actuators, vol. 73, Issues 1-2, Mar. 1999, pp. 30-36.

Cohen, "Automated Multianalyte Screening Tool for Classification of Forensic Samples", NIJ conference 2012, http://www.nij.gov/nij/events/nij_conference/2012/nij-2012-program-book.pdf, 2012.

Cohen, "Digital Microfluidic Sample Prep & Bioanalytical Systems", BioDot Workshop: From R&D to Quantitative IVDs, Irvine, CA, Apr. 24, 2012.

Cotten et al., "Digital Microfluidics: a novel platform for multiplexed detection of lysosomal storage diseases", Abstract # 3747.9. Pediatric Academic Society Conference, 2008.

Delapierre et al., "SmartDrop: An Integrated System from Sample Collection to Result using real-time PCR," 4th National Bio-Threat Conference, Dec. 7-9, 2010, New Orleans, LA, USA; Abstract in Proceedings, Poster presented at conference.

Delattre, Movie in news on TF1 (at 12'37" Cyril Delattre), http://videos.tf1.fr/jt-we/zoom-sur-grenoble-6071525.html, 2009, (English translation of audio).

(56) References Cited

OTHER PUBLICATIONS

Delattre, Movie in talk show "C Dans l'air" (at 24" Cyril Delattre), http://www.france5.fr/c-dans-l-air/sante/bientot-vous-ne-serez-plus-malade-31721, 2009, (English translation of audio).

Delattre, Movie on Web TV—Cite des sciences (at 3'26" Cyril Delattre), http://www.universcience.tv/video-laboratorie-de-poche-793.html, 2009, (English translation of audio).

Delattre et al., "Macro to microfluidics system for biological environmental monitoring", Biosensors and Bioelectronics, vol. 36, Issue 1, 2012, Available online, Apr. 27, 2012, 230-235.

Delattre et al., "SmartDrop: an integrated system from sample preparation to analysis using real-time PCR", 10th International Symposium on Protection against Chemical and Biological Warfare Agents; Stockholm, Sweden; poster, Jun. 10, 2010.

Delattre et al., "SmartDrop: An integrated system from sample preparation to analysis using real-time PCR", 10th International Symposium on Protection against Chemical and Biological Warfare Agents; Stockholm, Sweden; Abstract,paper,, Jun. 8-11, 2010.

Delattre et al., "Towards an industrial fabrication process for electrowetting chip using standard MEMS Technology", µTAS2008, San Diego; poster presented, Oct. 15, 2008.

Delattre et al., "Towards an industrial fabrication process for electrowetting chip using standard MEMS Technology", µTAS2008, San Diego; Abstract in proceedings, Oct. 13-16, 2008, 1696-1698.

Dewey, "Towards a Visual Modeling Approach to Designing Microelectromechanical System Transducers", Journal of Micromechanics and Microengineering, vol. 9, Dec. 1999, 332-340.

Dewey et al., "Visual modeling and design of microelectromechanical system tansducers", Microelectronics Journal, vol. 32, Apr. 2001, 373-381.

Eckhardt et al., "Development and validation of a single-step fluorometric assay for Hunter syndrome", APHL Newborn Screening and Genetic Testing Symposium, San Diego, 2011.

Emani et al., "Novel microfluidic platform for automated lab-on-chip testing of hypercoagulability panel", Blood Coagulation and Fibrinolysis, vol. 23(8), 2012, 760-8.

Emani et al., "Novel Microfluidic Platform for Point of Care Hypercoagulability Panel Testing", Circulation, vol. 122, 2010, A14693.

Fair et al., "A Micro- Watt Metal-Insulator-Solution-Transport (MIST) Device for Scalable Digital Bio-Microfluidic Systems", IEEE IEDM Technical Digest, 2001, 16.4.1-4.

Fair et al., "Advances in droplet-based bio lab-on-a-chip", BioChips 2003, Boston, 2003.

Fair et al., "Bead-Based and Solution-Based Assays Performed on a Digital Microfluidic Platform", Biomedical Engineering Society (BMES) Fall Meeting, Baltimore, MD, Oct. 1, 2005.

Fair, "Biomedical Applications of Electrowetting Systems", 5th International Electrowetting Workshop, Rochester, NY, May 31, 2006.

Fair et al., "Chemical and Biological Applications of Digital-Microfluidic Devices", IEEE Design & Test of Computers, vol. 24(1), Jan.-Feb. 2007, 10-24.

Fair et al., "Chemical and biological pathogen detection in a digital microfluidic platform", DARPA Workshop on Microfluidic Analyzers for DoD and National Security Applications, Keystone, CA, 2006.

Fair, "Digital microfluidics: is a true lab-on-a-chip possible?", Microfluid Nanofluid, vol. 3, Mar. 8, 2007, 245-281.

Fair, "Droplet-based microfluidic Genome sequencing", NHGRI PI's meeting, Boston, 2005.

Fair et al., "Electrowetting-based On-Chip Sample Processing for Integrated Microfluidics", IEEE Inter. Electron Devices Meeting (IEDM), 2003, 32.5.1-32.5.4.

Fair et al., "Integrated chemical/biochemical sample collection, pre-concentration, and analysis on a digital microfluidic lab-on-a-chip platform", Lab-on-a-Chip: Platforms, Devices, and Applications, Conf. 5591, SPIE Optics East, Philadelphia, Oct. 25-28, 2004.

Fair, "Scaling of Digital Microfluidic Devices for Picoliter Applications", The 6th International Electrowetting Meeting, Aug. 20-22, 2008, p. 14.

Fouillet, "Bio-Protocol Integration in Digital Microfluidic Chips", The 6th International Electrowetting Meeting, Aug. 20-22, 2008, p. 15.

Fouillet et al., "Design and Validation of a Complex Generic Fluidic Microprocessor Based on EWOD Droplet for Biological Applications", 9th International Conference on Miniaturized Systems for Chem and Life Sciences, Boston, MA, Oct. 9-13, 2005, 58-60.

Fouillet et al., "Digital microfluidic design and optimization of classic and new fluidic functions for lab on a chip systems", Microfluid Nanofluid, vol. 4, 2008, 159-165.

Graham et al., "Development of Quality Control Spots for Lysosomal Storage Disorders under cGMP", APHL Newborn Screening and Genetic Testing Symposium, San Diego, 2011.

Hua et al., "Multiplexed real-time polymerase chain reaction on a digital microfluidic platform", Analytical Chemistry, vol. 82, No. 6, Mar. 15, 2010, Published on Web, Feb. 12, 2010, 2310-2316.

Hua et al., "Rapid Detection of Methicillin-Resistant *Staphylococcus aureus* (MRSA) Using Digital Microfluidics", 12th Intl Conference on Miniaturized Systems for Chemistry and Life Sciences, Proc. µTAS, Oct. 12-16, 2008.

Jary et al., "Development of complete analytical system for Environment and homeland security", 14th International Conference on Biodetection Technologies 2009, Technological Responses to Biological Threats, Baltimore, MD; Abstract in Proceedings, poster distributed at conference, Jun. 25-26, 2009, 663.

Jary et al., "SmartDrop, Microfluidics for Biology", Forum 4i 2009, Grenoble, France; Flyer distributed at booth, May 14, 2009.

Jinks et al., "Newborn Screening for Krabbe and other Lysosomal Storage Diseases", The 3rd Annual Workshop on Krabbe Disease, Java Center, New York, Jul. 19-21, 2010.

Jun et al., "Valveless Pumping using Traversing Vapor Bubbles in Microchannels", J. Applied Physics, vol. 83, No. 11, Jun. 1998, pp. 5658-5664.

Kim et al., "MEMS Devices Based on the Use of Surface Tension", Proc. Int. Semiconductor Device Research Symposium (ISDRS'99), Charlottesville, VA, Dec. 1999, pp. 481-484.

Kim, "Microelectromechanical Systems (MEMS) at the UCLA Micromanufacturing Lab", Dig. Papers, Int. Microprocesses and Nanotechnology Conf. (MNC'98), Kyungju, Korea, Jul. 1998, pp. 54-55.

Kim et al., "Micromachines Driven by Surface Tension", AIAA 99/3800, 30th AIAA Fluid Dynamics Conference, Norfolk, VA, (Invited lecture), Jun. 1999, pp. 1-6.

Kleinert et al., "Dynamics and Stability of Oil Films During Droplet Transport by Electrowetting", 86th ACS Colloid & Surface Science Symposium, Abstract, Jun. 13, 2012.

Kleinert et al., "Dynamics and Stability of Oil Films During Droplet Transport by Electrowetting", 86th ACS Colloid & Surface Science Symposium, Presentation, Jun. 13, 2012.

Kleinert et al., "Dynamics and stability of oil films during droplet transport by electrowetting", 8th International Meeting on Electrowetting, Athens, Greece, Jun. 21-23, 2012.

Kleinert et al., "Electric Field Assisted Convective Assembly of Colloidal Crystal Coatings", Symposium MM: Evaporative Self Assembly of Polymers, Nanoparticles, and DNA, 2010 MRS Spring Meeting, San Francisco, CA., Apr. 6-8, 2010.

Kleinert et al., "Electric Field-Assisted Convective Assembly of Large-Domain Colloidal Crystals", The 82nd Colloid & Surface Science Symposium, ACS Division of Colloid & Surface Science, North Carolina State University, Raleigh, NC. www.colloids2008.org., Jun. 15-18, 2008.

Kleinert, "Electric-Field-Assisted Convective Assembly of Colloidal Crystal Coatings", Langmuir, vol. 26(12), May 13, 2010, 10380-10385.

Lee et al., "Microactuation by Continuous Electrowetting Phenomenon and Silicon Deep Rie Process", Proc. MEMS (DSC—vol. 66) ASME Int. Mechanical Engineering Congress and Exposition, Anaheim, CA, Nov. 1998, 475-480.

(56) References Cited

OTHER PUBLICATIONS

Lee et al., "Liquid Micromotor Driven by Continuous Electrowetting", Proc. IEEE Micro Electro Mechanical Systems Workshop, Heidelberg, Germany, Jan. 1998, pp. 538-543.

Lee et al., "Theory and Modeling of Continuous Electrowetting Microactuation", Proc. MEMS (MEMS-vol. 1), ASME Int. Mechanical Engineering Congress and Exposition, Nashville, TN, Nov. 1999, pp. 397-403.

Malk et al., "EWOD in coplanar electrode configurations", Proceedings of ASME 2010 3rd Joint US-European Fluids Engineering Summer Meeting and 8th International Conference on Nanochannels, Microchannels, and Minichannels, http://asmedl.org/getabs/servlet/GetabsServlet?prog=normal&id=ASMECP002010054501000023900000, Aug. 1-5, 2010.

Marchand et al., "Organic Synthesis in Soft Wall-Free Microreactors: Real-Time Monitoring of Fluorogenic Reactions", Analytical Chemistry, vol. 80, Jul. 2, 2008, 6051-6055.

Millington et al., "Applications of tandem mass spectrometry and microfluidics in newborn screening", Southeastern Regional Meeting of the American Chemical Society, Raleigh, North Carolina, 2012.

Millington et al., "Digital microfluidics: a future technology in the newborn screening laboratory", Seminars in Perinatology, vol. 34, Apr. 2010, 163-169.

Millington et al., "Digital Microfluidics: a novel platform for multiplexed detection of LSDs with potential for newborn screening", Association of Public Health Laboratories Annual Conference, San Antonio, TX, Nov 4, 2008.

Millington et al., "Digital Microfluidics: A Novel Platform for Multiplexing Assays Used in Newborn Screening", Proceedings of the7th International and Latin American Congress. Oral Presentations. Rev Invest Clin; vol. 61 (Supl. 1), 2009, 21-33.

Mugele et al., "Electrowetting: from basics to applications", Institution of Physics Publishing, Journal of Physics: Condensed Matter, 2005, R705-R774.

Paik et al., "A digital-microfluidic approach to chip cooling", IEEE Design & Test of Computers, vol. 25, Jul. 2008, 372-381.

Paik et al., "Adaptive Cooling of Integrated Circuits Using Digital Microfluidics", IEEE Transactions on VLSI, vol. 16, No. 4, 2008, 432-443.

Paik et al., "Adaptive Cooling of Integrated Circuits Using Digital Microfluidics", accepted for publication in IEEE Transactions on VLSI Systems, 2007, and Artech House, Norwood, MA, 2007.

Paik, "Adaptive Hot-Spot Cooling of Integrated Circuits Using Digital Microfluidics", Dissertation, Dept. of Electrical and Computer Engineering, Duke University, Apr. 25, 2006, 1-188.

Paik et al., "Adaptive hot-spot cooling of integrated circuits using digital microfluidics", Proceedings ASME International Mechanical Engineering Congress and Exposition, Orlando, Florida, USA. IMECE2005-81081, Nov. 5-11, 2005, 1-6.

Paik et al., "Coplanar Digital Microfluidics Using Standard Printed Circuit Board Processes", 9th International Conference on Miniaturized Systems for Chemistry and Life Sciences (MicroTAS), Boston, MA; Poster, 2005.

Paik et al., "Coplanar Digital Microfluidics Using Standard Printed Circuit Board Processes", 9th Int'l Conf. on Miniaturized Systems for Chemistry and Life Sciences, Boston, MA, Oct. 9-13, 2005, 566-68.

Paik et al., "Droplet-Based Hot Spot Cooling Using Topless Digital Microfluidics on a Printed Circuit Board", Int'l Workshops on Thermal Investigations of ICs and Systems (THERMINIC), 2005, 278-83.

Paik et al., "Electrowetting-based droplet mixers for microfluidic systems", Lab on a Chip (LOC), vol. 3. (more mixing videos available, along with the article, at LOC's website), 2003, 28-33.

Paik et al., "Programmable Flow-Through Real Time PCR Using Digital Microfluidics", 11th International Conference on Miniaturized Systems for Chemistry and Life Sciences, Paris, France, Oct. 7-11, 2007, 1559-1561.

Paik et al., "Programmable flow-through real-time PCR using digital microfluidics", Proc. Micro Total Analysis Systems (µTAS), Handout, 2007.

Paik et al., "Programmable flow-through real-time PCR using digital microfluidics", Proc. Micro Total Analysis Systems (µTAS), Poster, 2007.

Paik et al., "Rapid Droplet Mixers for Digital Microfluidic Systems", Masters Thesis, Duke Graduate School., 2002, 1-82.

Paik et al., "Rapid droplet mixers for digital microfluidic systems", Lab on a Chip, vol. 3. (More mixing videos available, along with the article, at LOC's website.), 2003, 253-259.

Paik et al., "Thermal effects on Droplet Transport in Digital Microfluids with Application to Chip Cooling Processing for Integrated Microfluidics", International Conference on Thermal, Mechanics, and Thermomechanical Phenomena in Electronic Systems (ITherm), 2004, 649-654.

Pamula, "A digital microfluidic platform for multiplexed explosive detection", Chapter 18, Electronics Noses and Sensors for the Detection of Explosives, Eds., J.W. Gardner and J. Yinon, Kluwer Academic Publishers, 2004.

Pamula et al., "A droplet-based lab-on-a-chip for colorimetric detection of nitroaromatic explosives", Proceedings of Micro Electro Mechanical Systems, 2005, 722-725.

Pamula et al., "Cooling of integrated circuits using droplet-based microfluidics", Proc. ACM Great Lakes Symposium on VLSI, Apr. 2003, 84-87.

Pamula, "Digital microfluidic lab-on-a-chip for multiplexing tests in newborn screening", Newborn Screening Summit: Envisioning a Future for Newborn Screening, Bethesda, MD, Dec. 7, 2009.

Pamula et al., "Digital microfluidic lab-on-a-chip for protein crystallization", 5th Protein Structure Initiative "Bottlenecks" Workshop, NIH, Bethesda, MD, Apr. 13-14, 2006, I-16.

Pamula et al., "Digital Microfluidic Methods in Diagnosis of Neonatal Biochemical Abnormalities", Developing Safe and Effective Devices and Instruments for Use in the Neonatal Intensive Care for the 21st Century, Pediatric Academic Societies' Annual Meeting, Vancouver, Canada, May 1-4, 2010.

Pamula et al., "Digital Microfluidic Platform for Multiplexing LSD Assays in Newborn Screening", LSD World Meeting, Las Vegas, NV, Feb. 16-18, 2011.

Pamula et al., "Digital Microfluidics Platform for Lab-on-a-chip applications", Duke University Annual Post Doctoral Research Day, 2002.

Pamula et al., "Microfluidic electrowetting-based droplet mixing", IEEE, 2002, 8-10.

Pamula et al., "Rapid LSD assays on a multiplex digital microfluidic platform for newborn screening", Lysosomal Disease Network World Symposium 2012, San Diego, CA, Feb. 8-19, 2012, 39.

Pamula, "Sample Preparation and Processing using Magnetic Beads on a Digital Microfluidic Platform", CHI's Genomic Sample Prep, San Francisco, CA, Jun. 9-10, 2009.

Pamula, "Sample-to-sequence-molecular diagnostics on a digital microfluidic lab on a chip", Pre-conference workshops, 4th International Conference on Birth Defects and Disabilities in the Developing World, New Dehli, India, Oct. 4, 2009.

Pollack et al., "Applications of Electrowetting-Based Digital Microfluidics in Clinical Diagnostics", Expert Rev. Mol. Diagn., vol. 11(4), 2011, 393-407.

Pollack et al., "Continuous sequencing-by-synthesis-based on a digital microfluidic platform", National Human Genome Research Institute, Advanced DNA Sequencing Technology Development Meeting, Chapel Hill, NC, Mar. 10-11, 2010.

Pollack, et al., "Electrowetting-Based Actuation of Droplets for Integrated Microfluidics", Lab on a Chip (LOC), vol. 2, 2002, 96-101.

Pollack et al., "Electrowetting-based actuation of liquid droplets for microfluidic applications", Appl. Phys. Letters, vol. 77, No. 11, Sep. 11, 2000, 1725-1726.

Pollack, "Electrowetting-based Microactuation of Droplets for Digital Microfluidics", PhD Thesis, Department of Electrical and Computer Engineering, Duke University, 2001.

(56) References Cited

OTHER PUBLICATIONS

Pollack et al., "Electrowetting-Based Microfluidics for High-Throughput Screening", smallTalk 2001 Conference Program Abstract, San Diego, Aug. 27-31, 2001, 149.
Pollack et al., "Investigation of electrowetting-based microfluidics for real-time PCR applications", Proc. 7th Int'l Conference on Micro Total Analysis Systems (mTAS), Squaw Valley, CA, Oct. 5-9, 2003, 619-622.
Pollack, "Lab-on-a-chip platform based digital microfluidics", The 6th International Electrowetting Meeting, Aug. 20-22, 2008, 16.
Pollack, "Sample Preparation Using Digital Microfluidics", Sample Prep 2012, Knowledge Press, Inc., May 3-4, 2012.
Punnamaraju, "Voltage and Photo Induced Effects in Droplet-Interface-Bilayer Lipid", PhD Thesis, University of Cincinnati, 2011.
Punnamaraju et al., "Voltage Control of Droplet Interface Bilayer Lipid Membrane Dimensions", Langmuir The ACS Journal of Surfaces and Colloids, vol. 27, Issue 2, 2011, Published on Web, Dec. 10, 2010, 618-626.
Ren et al., "Automated electrowetting-based droplet dispensing with good reproducibility", Proc. Micro Total Analysis Systems (mTAS), 7th Int. Conf.on Miniaturized Chem and Biochem Analysis Systems, Squaw Valley, CA, Oct. 5-9, 2003, 993-996.
Ren et al., "Automated on-chip droplet dispensing with volume control by electro-wetting actuation and capacitance metering", Sensors and Actuators B: Chemical, vol. 98, Mar. 2004, 319-327.
Ren et al., "Design and testing of an interpolating mixing architecture for electrowetting-droplet-on-chip chemical dilution", Transducers, 12th International Conference on Solid-State Sensors, Actuators and Microsystems, 2003, 619-622.
Ren et al., "Dynamics of electro-wetting droplet transport", Sensors and Actuators B (Chemical), vol. B87, No. 1, Nov. 15, 2002, 201-206.
Ren et al., "Micro/Nano Liter Droplet Formation and Dispensing by Capacitance Metering and Electrowetting Actuation", IEEE-NANO, 2002, 369-372.
Rival et al., "EWOD Digital Microfluidic Device for Single Cells Sample Preparation and Gene Expression Analysis", Lab Automation 2010, Palm Springs Convention Center, Palm Springs, CA, USA; Abstract in Proceedings, Poster distributed at conference, Jan. 23-27, 2010.
Rival et al., "Expression de gènes de quelques cellules sur puce EWOD/Gene expression of few cells on EWOD chip", iRTSV,http://www-dsv.cea.fr/var/plain/storage/original/media/File/iRTSV/thema_08(2).pdf (english translation), Winter 2009-2010.
Rival et al., "New insight on droplet dynamics under electrowetting actuation and design tools for speeding up product development", 8th Electrowetting Workshop, Athens, Greece. Abstract, 2012.
Rival et al., "New insight on droplet dynamics under electrowetting actuation and design tools for speeding up product development", 8th Electrowetting Workshop, Athens, Greece, Presentation, 2012.
Rival et al., "Towards Single Cells Gene Expression on EWOD Lab on Chip", ESONN 2008, Grenoble, France; Poster presented, Aug. 26, 2008.
Rival et al., "Towards single cells gene expression on EWOD lab on chip", ESONN, Grenoble, France, abstract in proceedings, Aug. 2008.
Rival et al., "Towards single cells gene expression preparation and analysis on ewod lab on chip", Nanobio Europe 2009, Poster distributed at conference, Jun. 16-18, 2009.
Rival et al., "Towards single cells gene expression preparation and analysis on ewod lab on chip", Nanobio Europe 2009, Abstract in proceedings, Jun. 16-18, 2009.
Rival et al., "Towards single cells gene expression preparation and analysis on ewod lab on chip", Lab on Chip Europe 2009 poster distributed at Conference, May 19-20, 2009.
Rival et al., "Towards single cells gene expression preparation and analysis on ewod lab on chip", Lab on Chip Europe 2009, Abstract in proceedings, May 19-20, 2009.
Rouse et al., "Digital microfluidics: a novel platform for multiplexing assays used in newborn screening", Poster 47, 41st AACC's Annual Oak Ridge Conference Abstracts, Clinical Chemistry, vol. 55, 2009, 1891.
Schell et al., "Evaluation of a Digital Microfluidic real-time PCR Platform to detect DNA of Candida albicans", Eur. J. Clin Microbiol Infect Dis, Published on-line DOI 10.1007/S10096-012-15616, Feb. 2012.
Sherman et al., "Flow Control by Using High-Aspect-Ratio, In-Plane Microactuators", Sensors and Actuators, vol. 73, 1999, pp. 169-175.
Sherman et al., "In-Plane Microactuator for Fluid Control Application", Proc. IEEE Micro Electro Mechanical Systems Workshop, Heidelberg, Germany, Jan. 1998, pp. 454-459.
Shi et al., "Evaluation of stability of fluorometric reagent kits for screening of Lysosomal Storage Disorders", APHL Newborn Screening and Genetic Testing Symposium, San Diego, 2011.
Sista et al., "96-Immunoassay Digital Microfluidic Multiwell Plate", Proc. µTAS, Oct. 12-16, 2008.
Sista, "Development of a Digital Microfluidic Lab-on-a-Chip for Automated Immunoassays with Magnetically Responsive Beads", PhD Thesis, Department of Chemical Engineering, Florida State University, 2007.
Sista et al., "Development of a digital microfluidic platform for point of care testing", Lab on a chip, vol. 8, Dec. 2008, First published as an Advance Article on the web, Nov. 5, 2008, 2091-2104.
Sista et al., "Digital Microfluidic Platform for Multiplexing Enzyme Assays: Implications for Lysosomal Storage Disease Screening in Newborns", Clinical Chemistry, vol. 57, Aug. 22, 2011, 1444-51.
Sista et al., "Digital Microfluidic platform for multiplexing LSD assays in newborn screening", APHL Newborn Screening and Genetic Testing Symposium, Orlando, May 3-6, 2010.
Sista et al., "Heterogeneous immunoassays using magnetic beads on a digital microfluidic platform", Lab on a Chip, vol. 8, Dec. 2008, First published as an Advance Article on the web, Oct. 14, 2008, 2188-2196.
Sista et al., "Multiplex Digital Microfluidic Platform for Rapid Newborn Screening of Lysosomal Storage Disorders", ACMG Annual Meeting, Charlotte, NC, 2012.
Sista et al., "Performance of a digital microfluidic assay for Gaucher and Hurler disorders", APHL Newborn Screening and Genetic Testing Symposium, San Diego, 2011.
Sista et al., "Rapid, Single-Step Assay for Hunter Syndrome in Dried Blood Spots Using Digital Microfluidics", Clinica Chimica Acta, vol. 412, 2011, 1895-97.
Sista et al., "Spatial multiplexing of immunoassays for small-volume samples", 10th PI Meeting IMAT, Bethesda, 2009.
Srinivasan et al., "3-D imaging of moving droplets for microfluidics using optical coherence tomography", Proc. 7th International Conference on Micro Total Analysis Systems (mTAS), Squaw Valley, CA, Oct. 5-9, 2003, 1303-1306.
Srinivasan et al., "A digital microfluidic biosensor for multianalyte detection", Proc. IEEE 16th Annual Int'l Conf. on Micro Electro Mechanical Systems Conference, 2003, 327-330.
Srinivasan, "A Digital Microfluidic Lab-on-a-Chip for Clinical Diagnostic Applications", Ph.D. thesis, Dept of Electrical and Computer Engineering, Duke University, 2005,.
Srinivasan et al., "An integrated digital microfluidic lab-on-a-chip for clinical diagnostics on human physiological fluids", Lab on a Chip, vol. 4, 2004, 310-315.
Srinivasan et al., "Clinical diagnostics on human whole blood, plasma, serum, urine, saliva, sweat and tears on a digital microfluidic platform", Proc. 7th International Conference on Micro Total Analysis Systems (mTAS), Squaw Valley, CA, Oct. 5-9, 2003, 1287-1290.
Srinivasan et al., "Commercializing electrowetting-based digital microfluidics: from the lab to a product", 8th International Meeting on Electrowetting, Athens, Greece, Jun. 21-23, 2012.
Srinivasan et al., "Digital Microfluidic Lab-on-a-Chip for Protein Crystallization", The 82nd ACS Colloid and Surface Science Symposium, 2008.

(56) References Cited

OTHER PUBLICATIONS

Srinivasan et al., "Digital Microfluidics: a novel platform for multiplexed detection of lysosomal storage diseases for newborn screening", AACC Oak Ridge Conference Abstracts, Clinical Chemistry, vol. 54, 2008, 1934.
Srinivasan et al., "Droplet-based microfluidic lab-on-a-chip for glucose detection", Analytica Chimica Acta, vol. 507, No. 1, 2004, 145-150.
Srinivasan et al., "Electrowetting", Chapter 5, Methods in Bioengineering: Biomicrofabrication and Biomicrofluidics, Ed. J.D. Zahn, ISBN: 9781596934009, Artech House Publishers, 2010.
Srinivasan et al., "Feasibility of a point of care newborn screening platform for hyperbilirubinemia", APHL Newborn Screening and Genetic Testing Symposium, San Diego, 2011.
Srinivasan et al., "Low cost digital microfluidic platform for protein crystallization", Enabling Technologies for Structural Biology, NIGMS Workshop, Bethesda, MD., Mar. 4-6, 2009, J-23.
Srinivasan et al., "Protein Stamping for MALDI Mass Spectrometry Using an Electrowetting-based Microfluidic Platform", Lab-on-a-Chip: Platforms, Devices, and Applications, Conf. 5591, SPIE Optics East, Philadelphia, Oct. 25-28, 2004.
Srinivasan et al., "Scalable Macromodels for Microelectromechanical Systems", Technical Proc. 2001 Int. Conf. on Modeling and Simulation of Microsystems, 2001, 72-75.
Su et al., "Yield Enhancement of Digital Microfluidics-Based Biochips Using Space Redundancy and Local Reconfiguration", Proc. Design, Automation and Test in Europe (DATE) Conf., IEEE, 2005, 1196-1201.
Sudarsan et al., "Printed circuit technology for fabrication of plastic based microfluidic devices", Analytical Chemistry vol. 76, No. 11, Jun. 1, 2004, Previously published on-line, line, May 2004, 3229-3235.
Thwar et al., "DNA sequencing using digital microfluidics", Poster 42, 41st AACC's Annual Oak Ridge Conference Abstracts, Clinical Chemistry vol. 55, 2009, 1891.
Tolun et al., "A Novel Fluorometric Enzyme Analysis Method for Hunter Syndrome Using Dried Blood Spots", Mol. Genet. Metab., 105, Issue 3, 2012; doi:10.1016/j.ymgme.2011.12.011, Epub, Dec. 21, 2011, 519-521.
Tolun et al., "Dried blood spot based enzyme assays for lysosomal storage disorders", 2011 Tokyo Meeting on Lysosomal Storage Disease Screening, Tokyo, Aug. 5, 2011.
Wang et al., "Comparison of enzyme activities for Pompe, Fabry, and Gaucher diseases on CDC's Quality Control spots between microplate fluorometry, mass spectrometry, and digital microfluidic fluorometry", APHL Newborn Screening and Genetic Testing Symposium, San Diego, 2011.
Wang et al., "Droplet-based micro oscillating-flow PCR chip", J. Micromechanics and Microengineering, vol. 15, 2005, 1369-1377.
Wang et al., "Efficient in-droplet separation of magnetic particles for digital microfluidics", Journal of Micromechanics and Microengineering, vol. 17, 2007, 2148-2156.
Weaver, "Application of Magnetic Microspheres for Pyrosequencing on a Digital Microfluidic Platform", Department of Electrical and Computer Engineering, Duke University, 2005.
Wulff-Burchfield et al., "Microfluidic platform versus conventional real-time polymerase chain reaction for the detection of Mycoplasma pneumoniae in respiratory specimens", Diagnostic Microbiology and Infectious Disease, vol. 67, 2010, 22-29.
Xu et al., "A Cross-Referencing-Based Droplet Manipulation Method for High-Throughput and Pin-Constrained Digital Microfluidic Arrays", Proceedings of conference on Design, Automation and Test in Europe, Apr. 2007.
Xu et al., "Automated Design of Pin-Constrained Digital Microfluidic Biochips Under Droplet-Interference Constraints", ACM Journal on Emerging Technologies is Computing Systems, vol. 3(3), 2007, 14:1-14:23.
Xu et al., "Automated solution preparation on a digital microfluidic lab-on-chip", PSI Bottlenecks Workshop, 2008.

Xu et al., "Automated, Accurate and Inexpensive Solution-Preparation on a Digital Microfluidic Biochip", Proc. IEEE Biomedical Circuits and Systems Conference (BioCAS), 2008, 301-304.
Xu et al., "Defect-Aware Synthesis of Droplet-Based Microfluidic Biochips", IEEE, 20th International Conference on VLSI Design, 2007.
Xu et al., "Defect-Tolerant Design and Optimization of a Digital Microfluidic Biochip for Protein Crystallization", IEEE Transactions on Computer Aided Design, vol. 29, No. 4, 2010, 552-565.
Xu et al., "Design and Optimization of a Digital Microfluidic Biochip for Protein Crystallization", Proc. IEEE/ACM International Conference on Computer-Aided Design (ICCAD), Nov. 2008, 297-301.
Xu et al., "Digital Microfluidic Biochip Design for Protein Crystallization", IEEE-NIH Life Science Systems and Applications Workshop, LISA, Bethesda, MD, Nov. 8-9, 2007, 140-143.
Xu et al., "Droplet-Trace-Based Array Partitioning and a Pin Assignment Algorithm for the Automated Design of Digital Microfluidic Biochips", CODES, 2006, 112-117.
Xu et al., "Integrated Droplet Routing in the Synthesis of Microfluidic Biochips", IEEE, 2007, 948-953.
Xu et al., "Parallel Scan-Like Test and Multiple-Defect Diagnosis for Digital Microfluidic Biochips", IEEE Transactions on Biomedical Circuits and Systems, vol. 1(2), Jun. 2007, 148-158.
Xu et al., "Parallel Scan-Like Testing and Fault Diagnosis Techniques for Digital Microfluidic Biochips", Proceedings of the 12th IEEE European Test Symposium (ETS), Freiburg, Germany, May 20-24, 2007, 63-68.
Yang et al., "Manipulation of droplets in microfluidic systems", Trends in Analytical Chemistry, vol. 29, Feb. 2010, 141-157.
Yao et al., "Spot Cooling Using Thermoelectric Microcooler", Proc. 18th Int. Thermoelectric Conf, Baltimore, VA, pp. 256-259, Aug. 1999.
Yi et al., "Channel-to-droplet extractions for on-chip sample preparation", Solid-State Sensor, Actuators and Microsystems Workshop (Hilton Head '06), Hilton Head Island, SC, Jun. 2006, 128-131.
Yi et al., "Characterization of electrowetting actuation on addressable single-side coplanar electrodes", Journal of Micromechanics and Microengineering, vol. 16.,Oct. 2006, 2053-2059.
Yi et al., "EWOD Actuation with Electrode-Free Cover Plate", Digest of Tech. papers, 13th International Conference on Solid-State Sensors, Actuators and Microsystems (Transducers '05), Seoul, Korea, Jun. 5-9, 2005, 89-92.
Yi et al., "Geometric surface modification of nozzles for complete transfer of liquid drops", Solid-State Sensor, Actuator and Microsystems Workshop, Hilton Head Island, South Carolina, Jun. 6-10, 2004, 164-167.
Yi, "Soft Printing of Biological Liquids for Micro-arrays: Concept, Principle, Fabrication, and Demonstration", Ph.D. dissertation, UCLA, 2004.
Yi et al., "Soft Printing of Droplets Digitized by Electrowetting", Transducers 12th Int'l Conf. on Solid State Sensors, Actuators and Microsystems, Boston, Jun. 8-12, 2003, 1804-1807.
Yi et al., "Soft Printing of Droplets Pre-Metered by Electrowetting", Sensors and Actuators A: Physical, vol. 114, Jan. 2004, 347-354.
Zeng et al., "Actuation and Control of Droplets by Using Electrowetting-on-Dielectric", Chin. Phys. Lett., vol. 21(9), 2004, 1851-1854.
Zhao et al., "Droplet Manipulation and Microparticle Sampling on Perforated Microfilter Membranes", J. Micromech. Microeng., vol. 18, 2008, 1-11.
Zhao et al., "In-droplet particle separation by travelling wave dielectrophoresis (twDEP) and EWOD", Solid-State Sensor, Actuators and Microsystems Workshop (Hilton Head '06), Hilton Head Island, SC, Jun. 2006, 181-184.
Zhao et al., "Micro air bubble manipulation by electrowetting on dielectric (EWOD): transporting, splitting, merging and eliminating of bubbles", Lab on a chip, vol. 7, 2007, First published as an Advance Article on the web, Dec. 4, 2006, 273-280.
Zhao et al., "Microparticle Concentration and Separation byTraveling-Wave Dielectrophoresis (twDEP) for Digital Microfluidics", J. Microelectromechanical Systems, vol. 16, No. 6, Dec. 2007, 1472-1481.

(56) References Cited

OTHER PUBLICATIONS

Zhao et al., "Optimization Techniques for the Synchronization of Concurrent Fluidic Operations in Pin-Constrained Digital Microfluidic Biochips", IEEE Transactions on Very Large Scale Integration (VLSI) Systems, vol. 20, No. 6, Jun. 2012, 1132-1145.
Zhao et al., "Synchronization of Concurrently-Implemented Fluidic Operations in Pin-Constrained Digital Microfluidic Biochips", VLSI Design, (Best Paper Award), 2010.
International Search Report and Written Opinion dated Nov. 23, 2012 from PCT International Application No. PCT/US2012/036949.
International Preliminary Report on Patentability dated Nov. 12, 2013 from PCT International Application No. PCT/US2012/036949.
Dhindsa et al. "Virtual electrowetting channels: electronic liquid transport with continuous channel functionality" Lab Chip vol. 10, 2010, pp. 832-836.
Fan et al., "General digital microfluidic platform manipulating dielectric and conductive droplets by dielectrophoresis and electrowetting", Lab Chip, 2009, 9:1236-1242.
European Search Report dated Oct. 14, 2014 from EP Application No. 12781709.
Office Action dated Apr. 24, 2015 from U.S. Appl. No. 13/545,716.
International Preliminary Report on Patentability dated Mar. 19, 2013 from PCT International Application No. PCT/US2011/051691.
International Search Report and Written Opinion dated May 1, 2012 from PCT International Application No. PCT/US2011/051691.
Office Action dated Jul. 10, 2015 from U.S. Appl. No. 13/822,990.
International Search Report and Written Opinion dated Jul. 9, 2012 from PCT International Application No. PCT/US2011/060714.
International Preliminary Report on Patentability dated May 21, 2013 from PCT International Application No. PCT/US2011/060714.
Office Action dated Aug. 17, 2015 from U.S. Appl. No. 13/988,190.
Ding, "System level architectural optimization of semi-reconfigurable micro fluidic system", M.S. Thesis, Duke University Dept of Electrical Engineering, 2000.
Gong et al., "Portable digital microfluidics platform with active but disposable Lab-On-Chip," Micro Electro Mechanical Systems, 17th IEEE International Conference on (MEMS), Maastricht, Netherlands, Jan. 25-29, 2004; Piscataway, NJ, IEEE, Jan. 25, 2004, pp. 355-358.
Moon, Ph.D. thesis, "Electrowetting-on-dielectric microfluidics: Modeling, physics, and MALDI application," University of California, Los Angeles, 2005.
Pamula et al., "Digital microfluidics for lab-on-a-chip applications", Emerging CAD challenges for biochip design, design, automation, and test in Europe, Munich, Germany, 2006.
Pamula et al., Microfluidic electrowetting-based droplet mixing, Proceedings, MEMS Conference Berkeley, Aug. 8-10, 2001.
Yi et al., "Microfluidics technology for manipulation and analysis of biological cells", Analytica Chimica Acta, vol. 560, 2006, 1-23.
Office Action dated Nov. 26, 2012 from U.S. Appl. No. 12/527,208.
Office Action dated Mar. 26, 2013 from U.S. Appl. No. 12/527,208.
International Search Report and Written Opinion dated Jul. 30, 2008 from PCT International Application No. PCT/US2008/054134.
International Preliminary Report on Patentability dated Nov. 17, 2009 from PCT International Application No. PCT/US2008/054134.
Published abstract from NIH Grant Project No. DK066956-02.
Published abstract from NIH Grant Project No. GM072155-02.
Office Action dated Jul. 20, 2015 from U.S. Appl. No. 14/338,889.
Paik, et al., "Active cooling techniques for integrated circuits", IEEE Transactions on VLSI, vol. 16, No. 4, 2008, 432-443.
Office Action dated Nov. 26, 2012 from related U.S. Pat. No. 8,872,527.
Office Action dated Mar. 26, 2013 from related U.S. Pat. No. 8,872,527.
Office Action dated Nov. 6, 2015 from U.S. Appl. No. 13/545,716.
Response to Office Action dated Jul. 24, 2015 from U.S. Appl. No. 13/545,716.
Response to Office Action dated Nov. 17, 2015 from U.S. Appl No. 13/988,190.
Response to Office Action dated Oct. 8, 2015 from U.S. Appl. No. 13/822,990.
Response to Office Action dated Feb. 18, 2015 from U.S. Pat. No. 8,872,527.
Binks, "Wetting: theory and experiment", Current Opinion in Colloids and Interface Science, vol. 6, No. 1, 17-21, 2001.
Chamberlain, et al., "Deletion screening of Duchenne musular dystrophy locus via multiplex DNA amplification", Nuc. Acid. Res. 16, pp. 11141-11156, 1988.
Cho, et al., "Concentration and binary separation of micro particles for droplet-based digital microfluidics", Lab Chip, vol. 7, 490-498, 2007.
Coltro et al., "Toner and paper-based fabrication techniques for microfluidic applications", Electrophoresis, vol. 31, 2487-2498, Jul. 2010.
Dorfman, et al., "Contamination-Free Continuouse Flow Microfluidic Polymerase Chain Reaction for Quantitative and Clinical Applications", Analytical Chemistry 77, 3700-3704, 2005.
Fowler, "Labon-on-a-Chip Technology May Present New ESD Challenges", Electrostatic Discharge (ESD) Journal. Retrieved on Apr. 18, 2008 from:http://www.esdjournal.com/articles/labchip/Lab.htm., Mar. 2002.
Gijs, Mam, "Magnetic bead handling on-chip:new opportunities for analytical applications", Microfluidics and Nanofluidics, vol. 1, 22-40, Oct. 2, 2004.
Huang, et al., "MEMS-based sample preparation for molecular diagnostics", Analytical and Bioanalytical Chemistry, vol. 372, 49-65, 2002.
Jones, et al., "Dielectrophoretic liquid actuation and nanodroplet formation", J. Appl. Phys., vol. 89, No. 2, 1441-1448, Jan. 2001.
Kim, et al., "Electrowetting on paper for electronic paper display", ACS Applied Materials & Interfaces, vol. 2, 3318-3323, Nov. 2010.
Margulies, et al., "Genome sequencing in microfabricated high-density picolitre reactors", Nature, vol. 437, 376-380 and Supplemental Materials, 2005.
Park, et al., "Single-sided continuous optoelectrowetting (SCOEW) droplet manipulation with light patterns", Lab on a chip, vol. 10, 1655-1661, Jul. 2010.
Pinho, et al., "Haemopoietic progenitors in the adult mouse omentum: permanent production of B lymphocytes and monocytes", Cell Tissue Res., vol. 319, No. 1, 91-102, Jan. 2005.
Poliski, Making materials fit the future: accommodating relentless technological requirements means researchers must recreate and reconfigure materials, frequently challenging established laws of physics, while keeping an eye on Moore's Law, R&D Magazine Conference, Dec. 2001.
Raj, et al., Composite Dielectrics and Surfactants for Low Voltage Electrowetting Devices, University/Government/Industry Micro/Nano Symposium, vol. 17, 187-190, Jul. 13-16, 2008.
Russom, et al., "Pyrosequencing in a Microfluidic Flow-Through Device", Anal. Chem. vol. 77, 7505-7511, 2005.
Schwartz, et al., "Dielectrophoretic approaches to sample preparation and analysis", The University of Texas, Dissertation, Dec. 2001.
Shah, et al., "EWOD-driven droplet microfluidic device integrated with optoelectronic tweezers as an automated platform for cellular isolation and analysis", Lab on a Chip, vol. 9, 1732-1739, Jun. 2009.
Tsuchiya, et al., "On-chip polymerase chain reaction microdevice employing a magnetic droplet-manipulation system", Sensors and Actuators B, vol. 130, 583-588, Oct. 18, 2007.
Welch, et al., "Picoliter DNA sequencing chemistry on an electrowetting-based digital microfluidic platform", Biotechnology Journal, vol. 6, 165-176, Feb. 2011.
Wheeler, et al., "Electrowetting-Based Microfluidics for Analysis of Peptides and Proteins by Matrix-Assisted Laser Desportion/Ionization Mass Spectrometry", Anal. Chem. 76, 4833-4838, 2004.
Yl et al., "Microfluidics technology for manipulation and analysis of biological cells", Analytica Chimica Acta, vol. 560, 1-23, 2006.

* cited by examiner

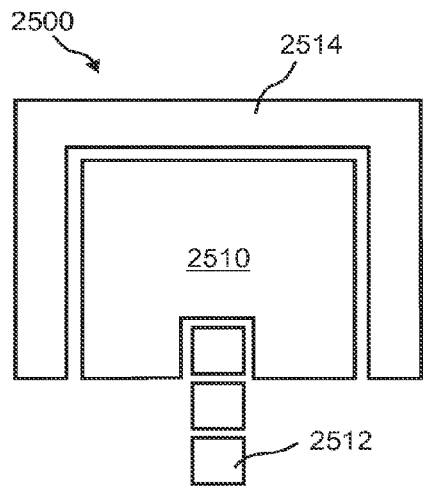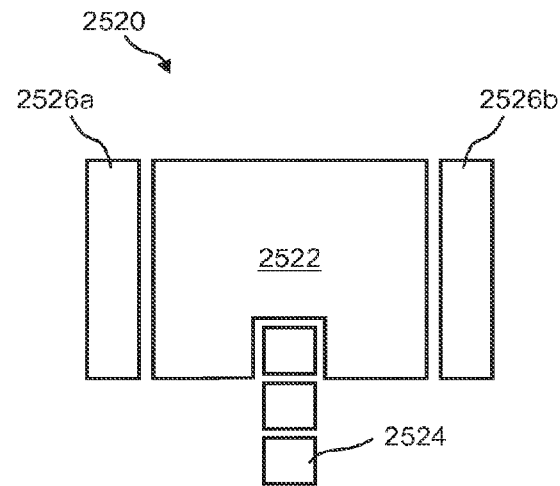
Figure 24A  Figure 24B
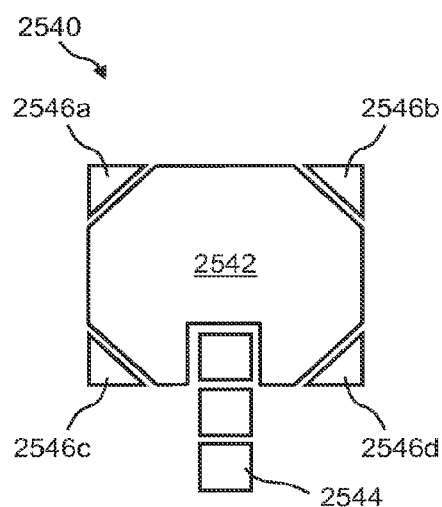
Figure 24C

MICROFLUIDIC FEEDBACK USING IMPEDANCE DETECTION

1 RELATED APPLICATIONS

This application is a continuation of U.S. patent application Ser. No. 14/116,553, filed Mar. 12, 2014, the application of which is a 35 U.S.C. 371 U.S. national phase entry of International Application No. PCT/US2012/036949 having an international filing date of May 8, 2012, the application of which claims the benefit of U.S. Provisional Application No. 61/483,827, filed May 9, 2011, the content of each of the aforementioned applications is herein incorporated by reference in its entirety.

2 BACKGROUND

A droplet actuator typically includes one or more substrates configured to form a surface or gap for conducting droplet operations. The one or more substrates establish a droplet operations surface or gap for conducting droplet operations and may also include electrodes arrange to conduct the droplet operations. The droplet operations substrate or the gap between the substrates may be coated or filled with a filler fluid that is immiscible with the liquid that forms the droplets. It may be beneficial to determine and/or verify the presence or absence of liquid at certain electrodes of a droplet actuator, such as at droplet operations electrodes and reservoir electrodes. Therefore, there is a need for methods of microfluidic feedback in droplet actuators.

3 BRIEF DESCRIPTION OF THE INVENTION

In one embodiment, the invention provides a method, which includes receiving an output voltage signal produced by a power supply, superimposing an excitation signal onto the output voltage signal to produce a superimposed signal, connecting the superimposed signal to an electrode in a droplet actuator, suppressing the output voltage signal when detecting an impedance of the electrode, and measuring the impedance of the electrode produced by the excitation signal, wherein the impedance indicates presence of liquid at the electrode. In some cases, superimposing the excitation signal includes adding the excitation signal to the output voltage signal. In certain embodiments suppressing the output voltage signal includes stopping the output voltage signal. In certain embodiments suppressing the output voltage signal includes disabling a switching action of the power supply. In certain embodiments suppressing the output voltage signal includes disabling the power supply. In certain embodiments the method includes receiving a suppression signal to suppress the output voltage signal from the power supply. In certain embodiments the method includes determining a saturation of the impedance. In certain embodiments the method includes: injecting the liquid into the droplet actuator, and stopping injection when the impedance indicates the liquid has flowed to the electrode. In certain embodiments the method includes: injecting the liquid into a gap in the droplet actuator, and stopping injection when the impedance indicates the liquid has flowed to the electrode. In certain embodiments the method includes: injecting the liquid into a reservoir in the droplet actuator, and stopping injection when the impedance indicates the liquid has flowed to the electrode. In certain embodiments the method includes: injecting the liquid to fill a reservoir in the droplet actuator, and stopping injection when the impedance indicates the liquid has flowed from the reservoir to the electrode. In certain embodiments the method includes: establishing a fluid path in the droplet actuator from an input port to a reservoir to the electrode, injecting the liquid through the input port to fill the reservoir, and stopping injection when the impedance indicates the liquid has flowed to the electrode. In certain embodiments the method includes: arranging an input port outside a boundary of a reservoir in the droplet actuator, forming a fluid path from the input port to the reservoir to the electrode, injecting the liquid through the input port to fill the reservoir, and stopping injection when the impedance indicates the liquid has flowed to the electrode. In another embodiment, the method includes generating an output voltage by a power supply, storing charge produced by the output voltage, superimposing an excitation signal onto the output voltage to produce a superimposed signal, connecting the superimposed signal to an electrode in a droplet actuator, suppressing the output voltage from the power supply when detecting an impedance at the electrode, supplying the charge to the droplet actuator to activate the electrode during the impedance, and measuring the impedance produced by the excitation signal while the output voltage is suppressed, wherein the impedance indicates presence of liquid at the electrode. In certain embodiments superimposing the excitation signal includes adding the excitation signal to the output voltage. In certain embodiments suppressing the output voltage includes at least one of stopping the output voltage generated by the power supply, disabling a switching action of the power supply, and disabling the power supply during the impedance measurement. In certain embodiments the invention includes activating a suppression signal to suppress the output voltage generated by the power supply. In certain embodiments the method includes deactivating the suppression signal to resume the output voltage generated by the power supply. In certain embodiments the method includes charging a capacitor to store the charge. In certain embodiments the method includes determining whether the impedance is saturated. In certain embodiments the method includes: injecting the liquid into the droplet actuator, and stopping injection when the impedance indicates the liquid has flowed to the electrode. In certain embodiments the method includes: injecting the liquid into a gap in the droplet actuator, and stopping injection into the gap when the impedance indicates the liquid has flowed to the electrode. In certain embodiments the method includes: injecting the liquid into a reservoir in the droplet actuator, and stopping injection into the reservoir when the impedance indicates the liquid has flowed to the electrode. In certain embodiments the method includes: establishing a fluid path in the droplet actuator from an input port to a reservoir to the electrode, injecting the liquid through the input port to fill the reservoir, and stopping injection when the impedance indicates the liquid has flowed to the electrode. In certain embodiments the method includes: arranging an input port outside a boundary of a reservoir in the droplet actuator, forming a fluid path from the input port to the reservoir to the electrode, injecting the liquid through the input port to fill the reservoir, and stopping injection when the impedance indicates the liquid has flowed to the electrode.

In another embodiment, the invention provides a system, comprising: a processor, memory, and code stored in the memory that when executed cause the processor at least to: receive an output voltage signal, superimpose an excitation signal onto the output voltage signal to produce a superimposed signal, connect the superimposed signal to an electrode in a droplet actuator, suppress the output voltage signal when detecting an impedance of the electrode, and measure the impedance of the electrode produced by the excitation signal, wherein the impedance indicates presence of liquid at the electrode. In some cases, the code further causes the processor to at least one of add the excitation signal to the output voltage signal, stop the output voltage signal, disable a switching action of the power supply, and disable the power supply. In some cases, the code further causes the processor to determine a saturation of the impedance. In some cases, the code further causes the processor to: cause injection of the liquid into the droplet actuator, and stop the injection when the impedance indicates the liquid has flowed to the electrode. In some cases, the code further causes the processor to: cause injection of the liquid into a gap in the droplet actuator, and stop the injection when the impedance indicates the liquid has flowed to the electrode. In some cases, the code further causes the processor to: cause injection of the liquid into a reservoir in the droplet actuator, and stop the injection when the impedance indicates the liquid has flowed to the electrode. In some cases, the code further causes the processor to: cause the injection of the liquid to fill a reservoir in the droplet actuator, and stop the injection when the impedance indicates the liquid has flowed from the reservoir to the electrode. In some cases, the code further causes the processor to: cause injection of the liquid into an input port of a reservoir in the droplet actuator, and stop the injection when the impedance indicates the liquid has flowed along a fluid path from the reservoir to the electrode. The code may be cause the operation of any of the methods of the invention.

The invention provides a computer readable medium storing processor executable instructions for performing a method, the method comprising: generating an output voltage by a power supply, storing charge produced by the output voltage, superimposing an excitation signal onto the output voltage to produce a superimposed signal, connecting the superimposed signal to an electrode in a droplet actuator, suppressing the output voltage from the power supply when detecting an impedance at the electrode, supplying the charge to the droplet actuator to activate the electrode during the impedance, and measuring the impedance produced by the excitation signal while the output voltage is suppressed, wherein the impedance indicates presence of liquid at the electrode. In some cases, the computer readable medium includes instructions for at least one of adding the excitation signal to the output voltage, stopping the output voltage generated by the power supply, disabling a switching action of the power supply, and disabling the power supply during the impedance measurement. In some cases, the computer readable medium includes instructions for activating a suppression signal to suppress the output voltage generated by the power supply. In some cases, the computer readable medium includes instructions for deactivating the suppression signal to resume the output voltage generated by the power supply. In some cases, the computer readable medium includes instructions for charging a capacitor to store the charge. In some cases, the computer readable medium includes instructions for determining the impedance is saturated. In some cases, the computer readable medium includes instructions for: injecting the liquid into the droplet actuator, and stopping injection when the impedance indicates the liquid has flowed to the electrode. In some cases, the computer readable medium includes instructions for: injecting the liquid into a gap in the droplet actuator, and stopping injection into the gap when the impedance indicates the liquid has flowed to the electrode. In some cases, the computer readable medium includes instructions for: injecting the liquid into a reservoir in the droplet actuator, and stopping injection into the reservoir when the impedance indicates the liquid has flowed to the electrode. In some cases, the computer readable medium includes instructions for: injecting the liquid through an input port to fill a reservoir in the droplet actuator, stopping injection when the impedance indicates the liquid has flowed to the electrode. In some cases, the computer readable medium includes instructions for: injecting the liquid into an input port of a reservoir in the droplet actuator, and stopping injection when the impedance indicates the liquid has flowed along a fluid path from the reservoir to the electrode.

4 DEFINITIONS

As used herein, the following terms have the meanings indicated.

"Activate," with reference to one or more electrodes, means affecting a change in the electrical state of the one or more electrodes which, in the presence of a droplet, results in a droplet operation. Activation of an electrode can be accomplished using alternating or direct current. Any suitable voltage may be used. For example, an electrode may be activated using a voltage which is greater than about 150 V, or greater than about 200 V, or greater than about 250 V, or from about 275 V to about 375 V, or about 300 V. Where alternating current is used, any suitable frequency may be employed. For example, an electrode may be activated using alternating current having a frequency from about 1 Hz to about 100 Hz, or from about 10 Hz to about 60 Hz, or from about 20 Hz to about 40 Hz, or about 30 Hz. Droplet operations and other droplet control electrodes of the invention may be activated.

"Bead," with respect to beads on a droplet actuator, means any bead or particle that is capable of interacting with a droplet on or in proximity with a droplet actuator. Beads may be any of a wide variety of shapes, such as spherical, generally spherical, egg shaped, disc shaped, cubical, amorphous and other three dimensional shapes. The bead may, for example, be capable of being subjected to a droplet operation in a droplet on a droplet actuator or otherwise configured with respect to a droplet actuator in a manner which permits a droplet on the droplet actuator to be brought into contact with the bead on the droplet actuator and/or off the droplet actuator. Beads may be provided in a droplet, in a droplet operations gap, or on a droplet operations surface. Beads may be provided in a reservoir that is external to a droplet operations gap or situated apart from a droplet operations surface, and the reservoir may be associated with a flow path that permits a droplet including the beads to be brought into a droplet operations gap or into contact with a droplet operations surface. Beads may be manufactured using a wide variety of materials, including for example, resins, and polymers. The beads may be any suitable size, including for example, microbeads, microparticles, nanobeads and nanoparticles. In some cases, beads are magnetically responsive; in other cases beads are not significantly magnetically responsive. For magnetically responsive beads, the magnetically responsive material may constitute substantially all of a bead, a portion of a bead, or only one component of a bead. The remainder of the bead may include, among other things, polymeric material, coatings, and moieties which permit attachment of an assay reagent Examples of suitable beads include flow cytometry microbeads, polystyrene microparticles and nanoparticles, functionalized polystyrene microparticles and nanoparticles, coated polystyrene microparticles and nanoparticles, silica microbeads, fluorescent microspheres and nanospheres, functionalized fluorescent microspheres and nanospheres, coated fluorescent microspheres and nanospheres, color dyed microparticles and nanoparticles, magnetic microparticles and nanoparticles, superparamagnetic microparticles and nanoparticles (e.g., DYNABEADS® particles, available from Invitrogen Group, Carlsbad, Calif.), fluorescent microparticles and nanoparticles, coated magnetic microparticles and nanoparticles, ferromagnetic microparticles and nanoparticles, coated ferromagnetic microparticles and nanoparticles, and those described in U.S. Patent Publication Nos. 20050260686, entitled "Multiplex flow assays preferably with magnetic particles as solid phase," published on Nov. 24, 2005; 20030132538, entitled "Encapsulation of discrete quanta of fluorescent particles," published on Jul. 17, 2003; 20050118574, entitled "Multiplexed Analysis of Clinical Specimens Apparatus and Method," published on Jun. 2, 2005; 20050277197. Entitled "Microparticles with Multiple Fluorescent Signals and Methods of Using Same," published on Dec. 15, 2005; 20060159962, entitled "Magnetic Microspheres for use in Fluorescence-based Applications," published on Jul. 20, 2006; the entire disclosures of which are incorporated herein by reference for their teaching concerning beads and magnetically responsive materials and beads. Beads may be pre-coupled with a biomolecule or other substance that is able to bind to and form a complex with a biomolecule. Beads may be pre-coupled with an antibody, protein or antigen, DNA/RNA probe or any other molecule with an affinity for a desired target. Examples of droplet actuator techniques for immobilizing magnetically responsive beads and/or non-magnetically responsive beads and/or conducting droplet operations protocols using beads are described in U.S. patent application Ser. No. 11/639,566, entitled "Droplet-Based Particle Sorting," filed on Dec. 15, 2006; U.S. Patent Application No. 61/039,183, entitled "Multiplexing Bead Detection in a Single Droplet," filed on Mar. 25, 2008; U.S. Patent Application No. 61/047,789, entitled "Droplet Actuator Devices and Droplet Operations Using Beads," filed on Apr. 25, 2008; U.S. Patent Application No. 61/086,183, entitled "Droplet Actuator Devices and Methods for Manipulating Beads," filed on Aug. 5, 2008; International Patent Application No. PCT/US2008/053545, entitled "Droplet Actuator Devices and Methods Employing Magnetic Beads," filed on Feb. 11, 2008; International Patent Application No. PCT/US2008/058018, entitled "Bead-based Multiplexed Analytical Methods and Instrumentation," filed on Mar. 24, 2008; International Patent Application No. PCT/US2008/058047, "Bead Sorting on a Droplet Actuator," filed on Mar. 23, 2008; and International Patent Application No. PCT/US2006/047486, entitled "Droplet-based Biochemistry," filed on Dec. 11, 2006; the entire disclosures of which are incorporated herein by reference. Bead characteristics may be employed in the multiplexing aspects of the invention. Examples of beads having characteristics suitable for multiplexing, as well as methods of detecting and analyzing signals emitted from such beads, may be found in U.S. Patent Publication No. 20080305481, entitled "Systems and Methods for Multiplex Analysis of PCR in Real Time," published on Dec. 11, 2008; U.S. Patent Publication No. 20080151240, "Methods and Systems for Dynamic Range Expansion," published on Jun. 26, 2008; U.S. Patent Publication No. 20070207513, entitled "Methods, Products, and Kits for Identifying an Analyte in a Sample," published on Sep. 6, 2007; U.S. Patent Publication No. 20070064990, entitled "Methods and Systems for Image Data Processing," published on Mar. 22, 2007; U.S. Patent Publication No. 20060159962, entitled "Magnetic Microspheres for use in Fluorescence-based Applications," published on Jul. 20, 2006; U.S. Patent Publication No. 20050277197, entitled "Microparticles with Multiple Fluorescent Signals and Methods of Using Same," published on Dec. 15, 2005; and U.S. Patent Publication No. 20050118574, entitled "Multiplexed Analysis of Clinical Specimens Apparatus and Method," published on Jun. 2, 2005.

"Droplet" means a volume of liquid on a droplet actuator. Typically, a droplet is at least partially bounded by a filler fluid. For example, a droplet may be completely surrounded by a filler fluid or may be bounded by filler fluid and one or more surfaces of the droplet actuator. As another example, a droplet may be bounded by filler fluid, one or more surfaces of the droplet actuator, and/or the atmosphere. As yet another example, a droplet may be bounded by filler fluid and the atmosphere. Droplets may, for example, be aqueous or non-aqueous or may be mixtures or emulsions including aqueous and non-aqueous components. Droplets may take a wide variety of shapes; nonlimiting examples include generally disc shaped, slug shaped, truncated sphere, ellipsoid, spherical, partially compressed sphere, hemispherical, ovoid, cylindrical, combinations of such shapes, and various shapes formed during droplet operations, such as merging or splitting or formed as a result of contact of such shapes with one or more surfaces of a droplet actuator. For examples of droplet fluids that may be subjected to droplet operations using the approach of the invention, see International Patent Application No. PCT/US 06/47486, entitled, "Droplet-Based Biochemistry," filed on Dec. 11, 2006. In various embodiments, a droplet may include a biological sample, such as whole blood, lymphatic fluid, serum, plasma, sweat, tear, saliva, sputum, cerebrospinal fluid, amniotic fluid, seminal fluid, vaginal excretion, serous fluid, synovial fluid, pericardial fluid, peritoneal fluid, pleural fluid, transudates, exudates, cystic fluid, bile, urine, gastric fluid, intestinal fluid, fecal samples, liquids containing single or multiple cells, liquids containing organelles, fluidized tissues, fluidized organisms, liquids containing multi-celled organisms, biological swabs and biological washes. Moreover, a droplet may include a reagent, such as water, deionized water, saline solutions, acidic solutions, basic solutions, detergent solutions and/or buffers. Other examples of droplet contents include reagents, such as a reagent for a biochemical protocol, such as a nucleic acid amplification protocol, an affinity-based assay protocol, an enzymatic assay protocol, a sequencing protocol, and/or a protocol for analyses of biological fluids. A droplet may include one or more beads.

"Droplet Actuator" means a device for manipulating droplets. For examples of droplet actuators, see Pamula et al., U.S. Pat. No. 6,911,132, entitled "Apparatus for Manipulating Droplets by Electrowetting-Based Techniques," issued on Jun. 28, 2005; Pamula et al., U.S. patent application Ser. No. 11/343,284, entitled "Apparatuses and Methods for Manipulating Droplets on a Printed Circuit Board," filed on filed on Jan. 30, 2006; Pollack et al., International Patent Application No. PCT/US2006/047486, entitled "Droplet-Based Biochemistry," filed on Dec. 11, 2006; Shenderov, U.S. Pat. No. 6,773,566, entitled "Electrostatic Actuators for Microfluidics and Methods for Using Same," issued on Aug. 10, 2004 and U.S. Pat. No. 6,565,727, entitled "Actuators for Microfluidics Without Moving Parts," issued on Jan. 24, 2000; Kim and/or Shah et al., U.S. patent application Ser. No. 10/343,261, entitled "Electrowetting-driven Micropumping," filed on Jan. 27, 2003, Ser. No. 11/275,668, entitled "Method and Apparatus for Promoting the Complete Transfer of Liquid Drops from a Nozzle," filed on Jan. 23, 2006, Ser. No. 11/460,188, entitled "Small Object Moving on Printed Circuit Board," filed on Jan. 23, 2006, Ser. No. 12/465,935, entitled "Method for Using Magnetic Particles in Droplet Microfluidics," filed on May 14, 2009, and Ser. No. 12/513,157, entitled "Method and Apparatus for Real-time Feedback Control of Electrical Manipulation of Droplets on Chip," filed on Apr. 30, 2009; Velev, U.S. Pat. No. 7,547,380, entitled "Droplet Transportation Devices and Methods Having a Fluid Surface," issued on Jun. 16, 2009; Sterling et al., U.S. Pat. No. 7,163,612, entitled "Method, Apparatus and Article for Microfluidic Control via Electrowetting, for Chemical, Biochemical and Biological Assays and the Like." issued on Jan. 16, 2007; Becker and Gascoyne et al., U.S. Pat. No. 7,641,779, entitled "Method and Apparatus for Programmable fluidic Processing," issued on Jan. 5, 2010, and U.S. Pat. No. 6,977,033, entitled "Method and Apparatus for Programmable fluidic Processing," issued on Dec. 20, 2005; Decre et al., U.S. Pat. No. 7,328,979, entitled "System for Manipulation of a Body of Fluid," issued on Feb. 12, 2008; Yamakawa et al., U.S. Patent Pub. No. 20060039823, entitled "Chemical Analysis Apparatus," published on Feb. 23, 2006; Wu, International Patent Pub. No. WO/2009/003184, entitled "Digital Microfluidics Based Apparatus for Heat-exchanging Chemical Processes," published on Dec. 31, 2008; Fouillet et al., U.S. Patent Pub. No. 20090192044, entitled "Electrode Addressing Method," published on Jul. 30, 2009; Fouillet et al., U.S. Pat. No. 7,052,244, entitled "Device for Displacement of Small Liquid Volumes Along a Micro-catenary Line by Electrostatic Forces," issued on May 30, 2006; Marchand et al., U.S. Patent Pub. No. 20080124252, entitled "Droplet Microreactor," published on May 29, 2008; Adachi et al., U.S. Patent Pub. No. 20090321262, entitled "Liquid Transfer Device," published on Dec. 31, 2009; Roux et al., U.S. Patent Pub. No. 20050179746, entitled "Device for Controlling the Displacement of a Drop Between two or Several Solid Substrates," published on Aug. 18, 2005; Dhindsa et al., "Virtual Electrowetting Channels: Electronic Liquid Transport with Continuous Channel Functionality," Lab Chip, 10:832-836 (2010); the entire disclosures of which are incorporated herein by reference, along with their priority documents. Certain droplet actuators will include one or more substrates arranged with a droplet operations gap therebetween and electrodes associated with (e.g., layered on, attached to, and/or embedded in) the one or more substrates and arranged to conduct one or more droplet operations. For example, certain droplet actuators will include a base (or bottom) substrate, droplet operations electrodes associated with the substrate, one or more dielectric layers atop the substrate and/or electrodes, and optionally one or more hydrophobic layers atop the substrate, dielectric layers and/or the electrodes forming a droplet operations surface. A top substrate may also be provided, which is separated from the droplet operations surface by a gap, commonly referred to as a droplet operations gap. Various electrode arrangements on the top and/or bottom substrates are discussed in the above-referenced patents and applications and certain novel electrode arrangements are discussed in the description of the invention. During droplet operations it is preferred that droplets remain in continuous contact, frequent contact or intermittent contact with a ground or reference electrode. A ground or reference electrode may be associated with the top substrate facing the gap, the bottom substrate facing the gap, in the gap. Where electrodes are provided on both substrates, electrical contacts for coupling the electrodes to a droplet actuator instrument for controlling or monitoring the electrodes may be associated with one or both plates. In some cases, electrodes on one substrate are electrically coupled to the other substrate so that only one substrate is in contact with the droplet actuator. In one embodiment, a conductive material (e.g., an epoxy, such as MASTER BOND™ Polymer System EP79, available from Master Bond, Inc., Hackensack, N.J.) provides the electrical connection between electrodes on one substrate and electrical paths on the other substrates, e.g., a ground electrode on a top substrate may be coupled to an electrical path on a bottom substrate by such a conductive material. Where multiple substrates are used, a spacer may be provided between the substrates to determine the height of the gap therebetween and define dispensing reservoirs. The spacer height may, for example, be from about 5 µm to about 600 µm, or about 100 µm to about 400 µm, or about 200 µm to about 350 µm, or about 250 µm to about 300 µm, or about 275 µm. The spacer may, for example, be formed of a layer of projections form the top or bottom substrates, and/or a material inserted between the top and bottom substrates. One or more openings may be provided in the one or more substrates for forming a fluid path through which liquid may be delivered into the droplet operations gap. The one or more openings may in some cases be aligned for interaction with one or more electrodes, e.g., aligned such that liquid flowed through the opening will come into sufficient proximity with one or more droplet operations electrodes to permit a droplet operation to be effected by the droplet operations electrodes using the liquid. The one or more openings may in some cases serve as vents for releasing liquid or gas from within the droplet operations gap. In some cases, the openings may be sealed or covered with a permeable material such as a membrane. For example a membrane having oleophobicity and hydrophobicity, such as VERSAPOR® Membrane (Pall Corp., Port Washington, N.Y.) may be used to cover an opening to facilitate escape of gasses while preventing escape of oil and aqueous liquids. The base (or bottom) and top substrates may in some cases be formed as one integral component, such as a folded or layered plastic or layered semiconductor construction. One or more reference electrodes may be provided on the base (or bottom) and/or top substrates and/or in the gap. Examples of reference electrode arrangements are provided in the above referenced patents and patent applications. In various embodiments, the manipulation of droplets by a droplet actuator may be electrode mediated, e.g., electrowetting mediated or dielectrophoresis mediated or Coulombic force mediated. Examples of other techniques for controlling droplet operations that may be used in the droplet actuators of the invention include using devices that induce hydrodynamic fluidic pressure, such as those that operate on the basis of mechanical principles (e.g. external syringe pumps, pneumatic membrane pumps, vibrating membrane pumps, vacuum devices, centrifugal forces, piezoelectric/ultrasonic pumps and acoustic forces); electrical or magnetic principles (e.g. electroosmotic flow, electrokinetic pumps, ferrofluidic plugs, electrohydrodynamic pumps, attraction or repulsion using magnetic forces and magnetohydrodynamic pumps); thermodynamic principles (e.g. gas bubble generation/phase-change-induced volume expansion); other kinds of surface-wetting principles (e.g. electrowetting, and opto-electrowetting, as well as chemically, thermally, structurally and radioactively induced surface-tension gradients); gravity; surface tension (e.g., capillary action): electrostatic forces (e.g., electroosmotic flow): centrifugal flow (substrate disposed on a compact disc and rotated); magnetic forces (e.g., oscillating ions causes flow); magnetohydrodynamic forces; and vacuum or pressure differential. In certain embodiments, combinations of two or more of the foregoing techniques may be employed to conduct a droplet operation in a droplet actuator of the invention. Similarly, one or more of the foregoing may be used to deliver liquid into a droplet operations gap, e.g., from a reservoir in another device or from an external reservoir of the droplet actuator (e.g., a reservoir associated with a droplet actuator substrate and a flow path from the reservoir into the droplet operations gap). Droplet operations surfaces of certain droplet actuators of the invention may be made from hydrophobic materials or may be coated or treated to make them hydrophobic. For example, in some cases some portion or all of the droplet operations surfaces may be derivatized with low surface-energy materials or chemistries, e.g., by deposition or using in situ synthesis using compounds such as poly- or per-fluorinated compounds in solution or polymerizable monomers. Examples include TEFLON® AF (available from DuPont, Wilmington, Del.), members of the cytop family of materials, coatings in the FLUOROPEL® family of hydrophobic and superhydrophobic coatings (available from Cytonix Corporation, Beltsville, Md.), silane coatings, fluorosilane coatings, hydrophobic phosphonate derivatives (e.g., those sold by Aculon, Inc), and NOVEC™ electronic coatings (available from 3M Company, St. Paul, Minn.), and other fluorinated monomers for plasma-enhanced chemical vapor deposition (PECVD). In some cases, the droplet operations surface may include a hydrophobic coating having a thickness ranging from about 10 nm to about 1,000 nm. Moreover, in some embodiments, the top substrate of the droplet actuator includes an electrically conducting organic polymer, which is then coated with a hydrophobic coating or otherwise treated to make the droplet operations surface hydrophobic. For example, the electrically conducting organic polymer that is deposited onto a plastic substrate may be poly(3,4-ethylenedioxythiophene) poly(styrenesulfonate) (PEDOT:PSS). Other examples of electrically conducting organic polymers and alternative conductive layers are described in Pollack et al., International Patent Application No. PCT/US2010/040705, entitled "Droplet Actuator Devices and Methods," the entire disclosure of which is incorporated herein by reference. One or both substrates may be fabricated using a printed circuit board (PCB), glass, indium tin oxide (ITO)-coated glass, and/or semiconductor materials as the substrate. When the substrate is ITO-coated glass, the ITO coating is preferably a thickness in the range of about 20 to about 200 nm, preferably about 50 to about 150 nm, or about 75 to about 125 nm, or about 100 nm. In some cases, the top and/or bottom substrate includes a PCB substrate that is coated with a dielectric, such as a polyimide dielectric, which may in some cases also be coated or otherwise treated to make the droplet operations surface hydrophobic. When the substrate includes a PCB, the following materials are examples of suitable materials: MITSUI™ BN-300 (available from MITSUI Chemicals America, Inc., San Jose Calif.); ARLON™ 11N (available from Arlon, Inc, Santa Ana, Calif.).; NELCO® N4000-6 and N5000-30/32 (available from Park Electrochemical Corp., Melville, N.Y.); ISOLA™ FR406 (available from Isola Group, Chandler, Ariz.), especially IS620; fluoropolymer family (suitable for fluorescence detection since it has low background fluorescence); polyimide family; polyester; polyethylene naphthalate; polycarbonate; polyetheretherketone; liquid crystal polymer, cyclo-olefin copolymer (COC); cyclo-olefin polymer (COP); aramid; THERMOUNT® non-woven aramid reinforcement (available from DuPont. Wilmington, Del.); NOMEX® brand fiber (available from DuPont, Wilmington, Del.); and paper. Various materials are also suitable for use as the dielectric component of the substrate. Examples include: vapor deposited dielectric, such as PARYLENE® (especially on glass) and PARYLENE™ N (available from Parylene Coating Services, Inc., Katy, Tex.); TEFLON® AF coatings; cytop; soldermasks, such as liquid photoimageable soldermasks (e.g., on PCB) like TAIYO™ PSR4000 series, TAIYO™ PSR and AUS series (available from Taiyo America, Inc. Carson City, Nev.) (good thermal characteristics for applications involving thermal control), and PROBIMER™ 8165 (good thermal characteristics for applications involving thermal control (available from Huntsman Advanced Materials Americas Inc., Los Angeles, Calif.); dry film soldermask, such as those in the VACREL® dry film soldermask line (available from DuPont, Wilmington, Del.); film dielectrics, such as polyimide film (e.g., KAPTON® polyimide film, available from DuPont, Wilmington, Del.), polyethylene, and fluoropolymers (e.g., FEP), polytetrafluoroethylene; polyester; polyethylene naphthalate; cyclo-olefin copolymer (COC); cyclo-olefin polymer (COP); any other PCB substrate material listed above; black matrix resin; and polypropylene. Droplet transport voltage and frequency may be selected for performance with reagents used in specific assay protocols. Design parameters may be varied, e.g., number and placement of on-actuator reservoirs, number of independent electrode connections, size (volume) of different reservoirs, placement of magnets/bead washing zones, electrode size, inter-electrode pitch, and gap height (between top and bottom substrates) may be varied for use with specific reagents, protocols, droplet volumes, etc. In some cases, a substrate of the invention may derivatized with low surface-energy materials or chemistries, e.g., using deposition or in situ synthesis using poly- or per-fluorinated compounds in solution or polymerizable monomers. Examples include TEFLON® AF coatings and FLUOROPEL® coatings for dip or spray coating, and other fluorinated monomers for plasma-enhanced chemical vapor deposition (PECVD). Additionally, in some cases, some portion or all of the droplet operations surface may be coated with a substance for reducing background noise, such as background fluorescence from a PCR substrate. For example, the noise-reducing coating may include a black matrix resin, such as the black matrix resins available from Toray industries, Inc., Japan. Electrodes of a droplet actuator are typically controlled by a controller or a processor, which is itself provided as part of a system, which may include processing functions as well as data and software storage and input and output capabilities. Reagents may be provided on the droplet actuator in the droplet operations gap or in a reservoir fluidly coupled to the droplet operations gap. The reagents may be in liquid form, e.g., droplets, or they may be provided in a reconstitutable form in the droplet operations gap or in a reservoir fluidly coupled to the droplet operations gap. Reconstitutable reagents may typically be combined with liquids for reconstitution. An example of reconstitutable reagents suitable for use with the invention includes those described in Meathrel, et al., U.S. Pat. No. 7,727,466, entitled "Disintegratable films for diagnostic devices," granted on Jun. 1, 2010.

"Droplet operation" means any manipulation of a droplet on a droplet actuator. A droplet operation may, for example, include: loading a droplet into the droplet actuator, dispensing one or more droplets from a source droplet; splitting, separating or dividing a droplet into two or more droplets; transporting a droplet from one location to another in any direction; merging or combining two or more droplets into a single droplet; diluting a droplet; mixing a droplet; agitating a droplet; deforming a droplet; retaining a droplet in position; incubating a droplet; heating a droplet; vaporizing a droplet; cooling a droplet; disposing of a droplet; transporting a droplet out of a droplet actuator; other droplet operations described herein; and/or any combination of the foregoing. The terms "merge," "merging," "combine," "combining" and the like are used to describe the creation of one droplet from two or more droplets. It should be understood that when such a term is used in reference to two or more droplets, any combination of droplet operations that are sufficient to result in the combination of the two or more droplets into one droplet may be used. For example, "merging droplet A with droplet B," can be achieved by transporting droplet A into contact with a stationary droplet B, transporting droplet B into contact with a stationary droplet A, or transporting droplets A and B into contact with each other. The terms "splitting," "separating" and "dividing" are not intended to imply any particular outcome with respect to volume of the resulting droplets (i.e., the volume of the resulting droplets can be the same or different) or number of resulting droplets (the number of resulting droplets may be 2, 3, 4, 5 or more). The term "mixing" refers to droplet operations which result in more homogenous distribution of one or more components within a droplet. Examples of "loading" droplet operations include microdialysis loading, pressure assisted loading, robotic loading, passive loading, and pipette loading. Droplet operations may be electrode-mediated. In some cases, droplet operations are further facilitated by the use of hydrophilic and/or hydrophobic regions on surfaces and/or by physical obstacles. For examples of droplet operations, see the patents and patent applications cited above under the definition of "droplet actuator." Impedance or capacitance sensing or imaging techniques may sometimes be used to determine or confirm the outcome of a droplet operation. Examples of such techniques are described in Sturmer et al., International Patent Pub. No. WO/2008/101194, entitled "Capacitance Detection in a Droplet Actuator," published on Aug. 21, 2008, the entire disclosure of which is incorporated herein by reference. Generally speaking, the sensing or imaging techniques may be used to confirm the presence or absence of a droplet at a specific electrode. For example, the presence of a dispensed droplet at the destination electrode following a droplet dispensing operation confirms that the droplet dispensing operation was effective. Similarly, the presence of a droplet at a detection spot at an appropriate step in an assay protocol may confirm that a previous set of droplet operations has successfully produced a droplet for detection. Droplet transport time can be quite fast. For example, in various embodiments, transport of a droplet from one electrode to the next may exceed about 1 sec, or about 0.1 sec, or about 0.01 sec, or about 0.001 sec. In one embodiment, the electrode is operated in AC mode but is switched to DC mode for imaging. It is helpful for conducting droplet operations for the footprint area of droplet to be similar to electrowetting area; in other words, 1×-, 2×-3×-droplets are usefully controlled operated using 1, 2, and 3 electrodes, respectively. If the droplet footprint is greater than the number of electrodes available for conducting a droplet operation at a given time, the difference between the droplet size and the number of electrodes should typically not be greater than 1; in other words, a 2× droplet is usefully controlled using 1 electrode and a 3× droplet is usefully controlled using 2 electrodes. When droplets include beads, it is useful for droplet size to be equal to the number of electrodes controlling the droplet, e.g., transporting the droplet.

"Filler fluid" means a fluid associated with a droplet operations substrate of a droplet actuator, which fluid is sufficiently immiscible with a droplet phase to render the droplet phase subject to electrode-mediated droplet operations. For example, the droplet operations gap of a droplet actuator is typically filled with a filler fluid. The filler fluid may, for example, be a low-viscosity oil, such as silicone oil or hexadecane filler fluid. The filler fluid may fill the entire gap of the droplet actuator or may coat one or more surfaces of the droplet actuator. Filler fluids may be conductive or non-conductive. Filler fluids may, for example, be doped with surfactants or other additives. For example, additives may be selected to improve droplet operations and/or reduce loss of reagent or target substances from droplets, formation of microdroplets, cross contamination between droplets, contamination of droplet actuator surfaces, degradation of droplet actuator materials, etc. Composition of the filler fluid, including surfactant doping, may be selected for performance with reagents used in the specific assay protocols and effective interaction or non-interaction with droplet actuator materials. Examples of filler fluids and filler fluid formulations suitable for use with the invention are provided in Srinivasan et al, International Patent Pub. Nos. WO/2010/027894, entitled "Droplet Actuators, Modified Fluids and Methods," published on Mar. 11, 2010, and WO/2009/021173, entitled "Use of Additives for Enhancing Droplet Operations," published on Feb. 12, 2009; Sista et al., International Patent Pub. No. WO/2008/098236, entitled "Droplet Actuator Devices and Methods Employing Magnetic Beads," published on Aug. 14, 2008; and Monroe et al., U.S. Patent Publication No. 20080283414, entitled "Electrowetting Devices," filed on May 17, 2007; the entire disclosures of which are incorporated herein by reference, as well as the other patents and patent applications cited herein.

"Immobilize" with respect to magnetically responsive beads, means that the beads are substantially restrained in position in a droplet or in filler fluid on a droplet actuator. For example, in one embodiment, immobilized beads are sufficiently restrained in position in a droplet to permit execution of a droplet splitting operation, yielding one droplet with substantially all of the beads and one droplet substantially lacking in the beads.

"Magnetically responsive" means responsive to a magnetic field. "Magnetically responsive beads" include or are composed of magnetically responsive materials. Examples of magnetically responsive materials include paramagnetic materials, ferromagnetic materials, ferrimagnetic materials, and metamagnetic materials. Examples of suitable paramagnetic materials include iron, nickel, and cobalt, as well as metal oxides, such as $Fe_3O_4$, $BaFe_{12}O_{19}$, CoO, NiO, $Mn_2O_3$, $Cr_2O_3$, and CoMnP.

"Reservoir" means an enclosure or partial enclosure configured for holding, storing, or supplying liquid. A droplet actuator system of the invention may include on-cartridge reservoirs and/or off-cartridge reservoirs. On-cartridge reservoirs may be (1) on-actuator reservoirs, which are reservoirs in the droplet operations gap or on the droplet operations surface; (2) off-actuator reservoirs, which are reservoirs on the droplet actuator cartridge, but outside the droplet operations gap, and not in contact with the droplet operations surface: or (3) hybrid reservoirs which have on-actuator regions and off-actuator regions. An example of an off-actuator reservoir is a reservoir in the top substrate. An off-actuator reservoir is typically in fluid communication with an opening or flow path arranged for flowing liquid from the off-actuator reservoir into the droplet operations gap, such as into an on-actuator reservoir. An off-cartridge reservoir may be a reservoir that is not part of the droplet actuator cartridge at all, but which flows liquid to some portion of the droplet actuator cartridge. For example, an off-cartridge reservoir may be part of a system or docking station to which the droplet actuator cartridge is coupled during operation. Similarly, an off-cartridge reservoir may be a reagent storage container or syringe which is used to force fluid into an on-cartridge reservoir or into a droplet operations gap. A system using an off-cartridge reservoir will typically include a fluid passage means whereby liquid may be transferred from the off-cartridge reservoir into an on-cartridge reservoir or into a droplet operations gap.

"Transporting into the magnetic field of a magnet," "transporting towards a magnet," and the like, as used herein to refer to droplets and/or magnetically responsive beads within droplets, is intended to refer to transporting into a region of a magnetic field capable of substantially attracting magnetically responsive beads in the droplet. Similarly, "transporting away from a magnet or magnetic field," "transporting out of the magnetic field of a magnet," and the like, as used herein to refer to droplets and/or magnetically responsive beads within droplets, is intended to refer to transporting away from a region of a magnetic field capable of substantially attracting magnetically responsive beads in the droplet, whether or not the droplet or magnetically responsive beads is completely removed from the magnetic field. It will be appreciated that in any of such cases described herein, the droplet may be transported towards or away from the desired region of the magnetic field, and/or the desired region of the magnetic field may be moved towards or away from the droplet. Reference to an electrode, a droplet, or magnetically responsive beads being "within" or "in" a magnetic field, or the like, is intended to describe a situation in which the electrode is situated in a manner which permits the electrode to transport a droplet into and/or away from a desired region of a magnetic field, or the droplet or magnetically responsive beads is/are situated in a desired region of the magnetic field, in each case where the magnetic field in the desired region is capable of substantially attracting any magnetically responsive beads in the droplet. Similarly, reference to an electrode, a droplet, or magnetically responsive beads being "outside of" or "away from" a magnetic field, and the like, is intended to describe a situation in which the electrode is situated in a manner which permits the electrode to transport a droplet away from a certain region of a magnetic field, or the droplet or magnetically responsive beads is/are situated away from a certain region of the magnetic field, in each case where the magnetic field in such region is not capable of substantially attracting any magnetically responsive beads in the droplet or in which any remaining attraction does not eliminate the effectiveness of droplet operations conducted in the region. In various aspects of the invention, a system, a droplet actuator, or another component of a system may include a magnet, such as one or more permanent magnets (e.g., a single cylindrical or bar magnet or an array of such magnets, such as a Halbach array) or an electromagnet or array of electromagnets, to form a magnetic field for interacting with magnetically responsive beads or other components on chip. Such interactions may, for example, include substantially immobilizing or restraining movement or flow of magnetically responsive beads during storage or in a droplet during a droplet operation or pulling magnetically responsive beads out of a droplet.

"Washing" with respect to washing a bead means reducing the amount and/or concentration of one or more substances in contact with the bead or exposed to the bead from a droplet in contact with the bead. The reduction in the amount and/or concentration of the substance may be partial, substantially complete, or even complete. The substance may be any of a wide variety of substances: examples include target substances for further analysis, and unwanted substances, such as components of a sample, contaminants, and/or excess reagent. In some embodiments, a washing operation begins with a starting droplet in contact with a magnetically responsive bead, where the droplet includes an initial amount and initial concentration of a substance. The washing operation may proceed using a variety of droplet operations. The washing operation may yield a droplet including the magnetically responsive bead, where the droplet has a total amount and/or concentration of the substance which is less than the initial amount and/or concentration of the substance. Examples of suitable washing techniques are described in Pamula et al., U.S. Pat. No. 7,439,014, entitled "Droplet-Based Surface Modification and Washing," granted on Oct. 21, 2008, the entire disclosure of which is incorporated herein by reference.

The terms "top," "bottom," "over," "under," and "on" are used throughout the description with reference to the relative positions of components of the droplet actuator, such as relative positions of top and bottom substrates of the droplet actuator. It will be appreciated that the droplet actuator is functional regardless of its orientation in space.

When a liquid in any form (e.g., a droplet or a continuous body, whether moving or stationary) is described as being "on", "at", or "over" an electrode, array, matrix or surface, such liquid could be either in direct contact with the electrode/array/matrix/surface, or could be in contact with one or more layers or films that are interposed between the liquid and the electrode/array/matrix/surface.

When a droplet is described as being "on" or "loaded on" a droplet actuator, it should be understood that the droplet is arranged on the droplet actuator in a manner which facilitates using the droplet actuator to conduct one or more droplet operations on the droplet, the droplet is arranged on the droplet actuator in a manner which facilitates sensing of a property of or a signal from the droplet, and/or the droplet has been subjected to a droplet operation on the droplet actuator.

BRIEF DESCRIPTION OF THE DRAWINGS

FIGS. 24A, 24B, and 24C illustrate top views of three electrode arrangements, respectively, which are more examples of electrode configurations for helping to detect whether a sample reservoir is fully loaded.

6 DESCRIPTION

The present invention is microfluidic feedback methods using impedance detection with respect to electrodes of droplet actuators. For example, the microfluidic feedback methods of the invention may correlate impedance measurements to the presence or absence of liquid at certain electrodes of a droplet actuator, such as at certain droplet operations electrodes and/or certain reservoir electrodes. In this way, impedance detection operations may be used to verify and/or monitor the presence or absence of liquid at a certain electrode in a droplet actuator. Additionally, certain actions may be taken in the protocol that is executing on the droplet actuator based on the presence or absence of liquid at a certain electrode, as determined using impedance detection according to the present invention.

Certain embodiments of the invention include improved impedance sensing circuits. In one example, the impedance sensing circuit provides a mechanism for reducing, preferably entirely eliminating, noise on the reference voltage power supply during impedance detection operations. In another example, the impedance sensing circuit provides a mechanism for flagging a saturation condition with respect to the response signal.

6.1 Digital Microfluidics

Digital microfluidic technology conducts droplet operations on discrete droplets by electrical control of their surface tension (electrowetting). The droplets may be sandwiched between two substrates, a bottom substrate and a top substrate separated by a gap. The bottom substrate may, for example, be a printed circuit board (PCB) with an arrangement of electrically addressable electrodes. The top substrate may, for example, be an injection molded plastic top substrate with a reference electrode plane made, for example, from conductive ink or indium-tin oxide (ITO). The bottom substrate and the top substrate may be coated with a hydrophobic material. The space around the droplets (i.e., the gap between bottom and top substrates) may be filled with an immiscible inert fluid, such as silicone oil, to prevent evaporation of the droplets and to facilitate their transport within the device. An electric field, formed when voltage is applied to a control electrode on the bottom substrate, reduces the interfacial tension between the droplet and the electrode. This effect may be used to transport droplets using surface energy gradients established by activating a pattern of control electrodes on the bottom substrate along any path of contiguous electrodes. Other droplet operations may be effected by varying the patterns of voltage activation; examples include merging, splitting, mixing, and dispensing of droplets.

6.2 Methods of Microfluidic Feedback Using Impedance Detection

Figure 1:
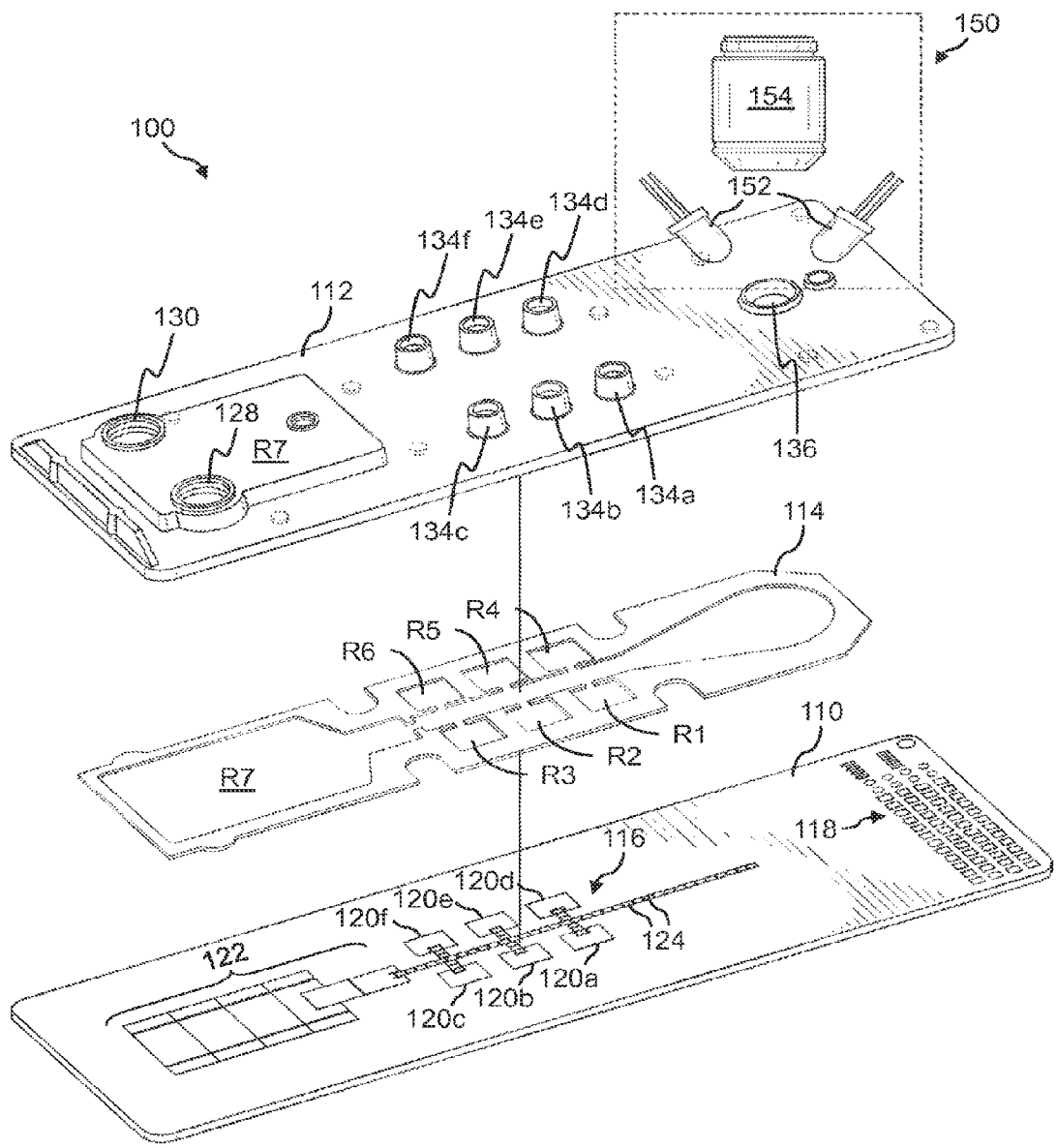
FIG. 1 illustrates an exploded view of an example of a droplet actuator that is suitable for using impedance detection as a mechanism of microfluidics feedback in a droplet actuator.

FIG. 1 illustrates an exploded view of an example of a droplet actuator 100 that may be used to provide microfluidic feedback using impedance detection. In one embodiment, droplet actuator 100 is configured for integrated sample preparation and nucleic acid testing of a single sample. Droplet actuator 100 may include a bottom substrate 110 and a top substrate 112. A gasket 114 may be sandwiched between bottom substrate 110 and top substrate 112.

In one example, bottom substrate 110 may be a PCB that has an electrode arrangement 116 and a set of power/signal input/output (I/O) pads 118 patterned thereon. Electrode arrangement 116 may include, for example, reservoir electrodes 120a through 120f that are associated with reservoirs R1 through R6, respectively. Electrode arrangement 116 may also include a sample reservoir electrode 122 that is associated with a sample reservoir R7. Reservoir electrodes 120a through 120f and sample reservoir electrode 122 are arranged in relation to a path, line, and/or array of droplet operations electrodes 124 (e.g., electrowetting electrodes). Sample reservoir electrode 122 may be segmented into an arrangement of multiple individually controlled electrodes, which is shown with reference to FIGS. 2 and 3. Droplet operations are conducted atop these various electrodes on a droplet operations surface. More details of electrode arrangement 116 are described with reference to FIGS. 2, 3, 4A, and 4B.

Top substrate 112 may be formed of a material that is substantially transparent to visible light, ultraviolet (UV) light, and/or any wavelength light of interest. For example, top substrate 112 may be formed of glass, injection-molded plastic, and/or silicon. Additionally, top substrate 112 may be coated with ITO, thereby providing an electrical ground plane.

A clearance region is provided in gasket 114. When bottom substrate 110, top substrate 112, and gasket 114 are assembled together, the clearance region of gasket 114 forms a gap between bottom substrate 110 and top substrate 112 at the droplet operations surface. The thickness of gasket 114 may be used to set the height of the gap. Further, the shape of the clearance region of gasket 114 substantially corresponds to the shape of electrode arrangement 116 of bottom substrate 110. In one example, the shape of the clearance region of gasket 114 at reservoir electrodes 120a through 120f and at sample reservoir electrode 122, together with bottom substrate 110 and top substrate 112, form reservoirs R1 through R6 and sample reservoir R7. Reservoirs R1 through R6 and sample reservoir R7 are examples of on-actuator reservoirs. Reservoirs R1 through R6 may be, for example, reagent reservoirs for holding/dispensing various reagent fluids, such as, but not limited to, elution buffer solution and wash buffer solution. Respective input ports 134 (e.g., input ports 134a through 134f) of reservoirs R1 through R6 may be integrated into top substrate 112.

Sample reservoir R7 may be provided for preparing and dispensing sample fluids. Sample reservoir R7 may be of sufficient size to contain a large volume of fluid, e.g., about 1.5 mL. One or more input ports of sample reservoir R7 may be integrated into top substrate 112. For example, an input port 128 for loading sample fluids into sample reservoir R7 may be integrated into top substrate 112. Additionally, an input port 130 for loading sample preparation reagents (e.g., lysis buffer, nucleic acid capture beads) into sample reservoir R7 may be integrated into top substrate 112. Top substrate 112 may include certain features (not shown) for helping define the volume of the on-actuator reservoirs (e.g., reservoirs R1 through R6 and sample reservoir R7).

When bottom substrate 110, top substrate 112, and gasket 114 are assembled together, input port 128 and input port 130 in top substrate 112 are substantially aligned with at least a portion of sample reservoir electrode 122 of bottom substrate 110. Similarly, input ports 134 in top substrate 112 are substantially aligned with at least a portion of their respective reservoir electrodes 120 of bottom substrate 110. More details of droplet actuator 100 are described with reference to FIGS. 2 through 5H.

A port (e.g., input port 128, input port 130, and input ports 134) is an entrance/exit (opening) to the droplet operations gap. Liquid may flow through the port into any portion of the gap. That could be into a reservoir region of the gap or onto a droplet operations pathway. A port may be used to fill the gap with filler fluid. However, in most cases, a reagent fluid or sample fluid flowing through a port should come into sufficient proximity with an electrode, such that the electrode can be used to conduct one or more droplet operations using the liquid, such as droplet transport, splitting, and dispensing.

Additionally, the gap height at sample reservoir R7 may be greater than the gap height at reservoirs R1 through R6 and/or along unit-sized droplet operations electrodes 124. For example, the gap height at sample reservoir R7 may be about >3 mm to facilitate storage of larger liquid volumes (e.g., about 1.5 mL) and ready dispensing of droplets. While the gap height at reservoirs R1 through R6 and/or along droplet operations electrodes 124 may be about 250-500 μm in order to facilitate, for example, rapid transport, mixing, washing, and/or incubation of one or more droplets. The gap height transition region may be at the dispensing end of sample reservoir R7, which is the portion of sample reservoir R7 that feeds the line of droplet operations electrodes 124.

An imaging system 150 may be used in combination with droplet actuator 100. For example, a detection electrode 135 is provided at the end of the line of droplet operations electrodes 124 that is opposite sample reservoir R7. Accordingly, a detection window 136 may be included in top substrate 112 at detection electrode 135. Imaging system 150 uses detection window 136 for performing detection operations on any droplet atop detection electrode 135. The amount of transparency provided at detection window 136 may vary. Detection window 136 may be formed to direct and/or filter light, e.g., formed as a lens and/or as an optical filter that excludes certain wavelengths. Light energy that is generated in the gap of droplet actuator 100 may be transmitted through detection window 136 and then captured by imaging system 150. In one example, imaging system 150 may include one or more light-emitting diodes (LEDs) 152 (i.e., an illumination source) and a digital image capture device, such as a charge-coupled device (CCD) camera 154. (Only the lens of CCD camera 154 is shown in FIG. 1). In one example, one LED 152 may emit green light (525 nm wavelength) and another LED 152 may emit red light (635 nm wavelength).

Figure 2:
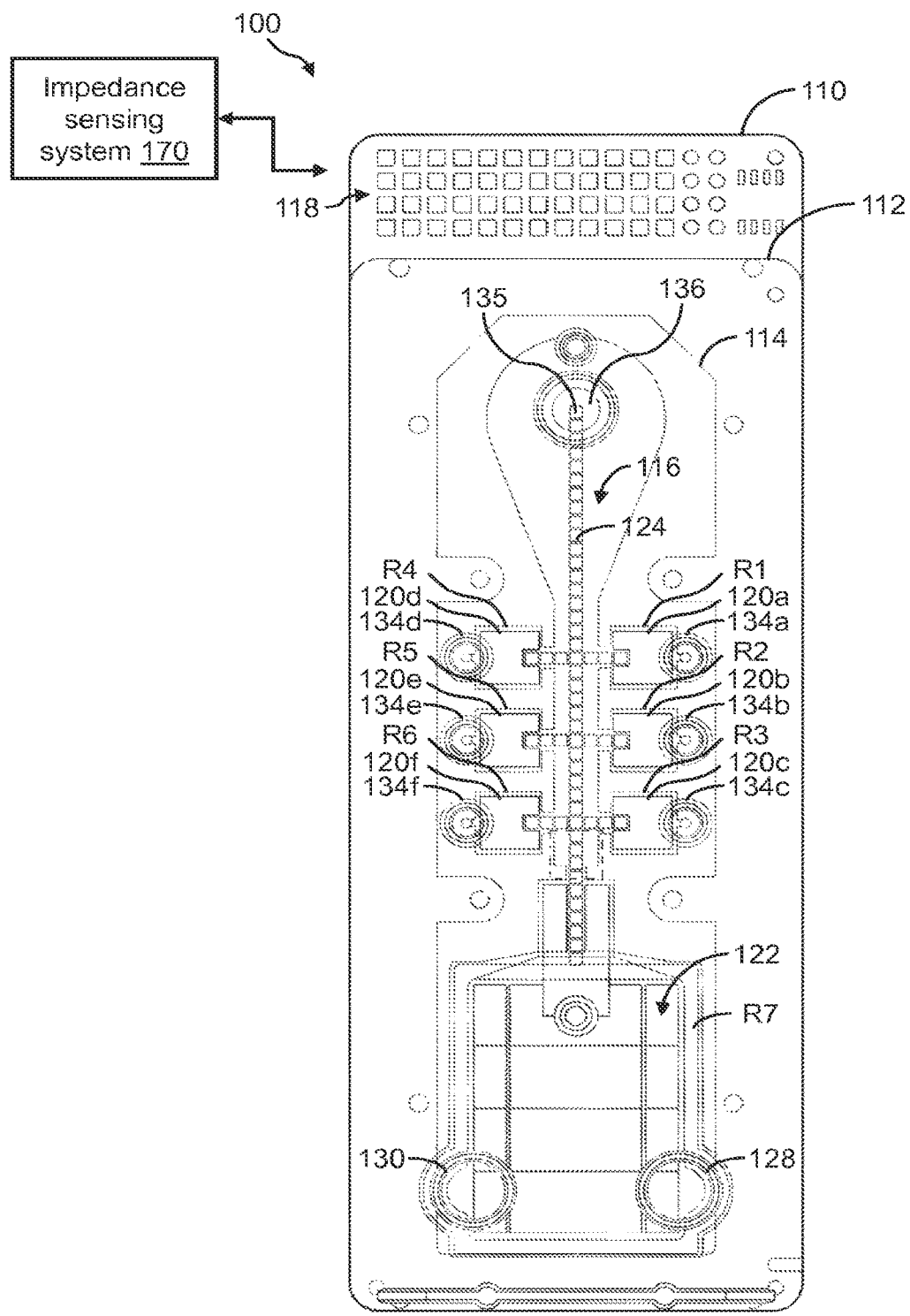
FIG. 2 illustrates a top down view of the droplet actuator of FIG. 1 when its components are fully assembled.

FIG. 2 illustrates a top down view of droplet actuator 100 when its components are fully assembled. More specifically, FIG. 2 shows bottom substrate 110, top substrate 112, and gasket 114 assembled together to form droplet actuator 100. FIG. 2 shows that the clearance region of gasket 114 substantially corresponds to the shape of electrode arrangement 116 of bottom substrate 110. Additionally, the alignment is shown of sample reservoir R7 to sample reservoir electrode 122 of bottom substrate 110. Similarly, the alignment is shown of reservoirs R1 through R6 to their respective reservoir electrodes 120 of bottom substrate 110.

I/O pads 118 are contacts that are connected by wiring traces to the electrodes, such as to reservoir electrodes 120, sample reservoir electrode 122, and droplet operations electrodes 124. In one example, I/O pads 118 are used for applying electrowetting voltages. When a droplet actuator, such as droplet actuator 100, is installed in a microfluidics system (not shown), I/O pads 118 are coupled to a controller, which includes the circuitry for detecting impedance at a specific electrode. One I/O pad 118 may be coupled to top substrate 112 to provide the return path for the circuit. FIG. 2 also shows an impedance sensing system 170, which is one example of circuitry for detecting impedance at a specific electrode. Impedance sensing system 170 may be, for example, an impedance spectrometer.

Impedance sensing system 170 may be used to monitor the capacitive loading of any electrode with or without liquid thereon. For examples of suitable capacitance detection techniques, see Sturmer et al., International Patent Publication No. WO/2008/101194, entitled "Capacitance Detection in a Droplet Actuator," published on Aug. 21, 2008; and Kale et al., International Patent Publication No. WO/2002/080822, entitled "System and Method for Dispensing Liquids," published on Oct. 17, 2002; the entire disclosures of which are incorporated herein by reference.

According to the invention, impedance sensing system 170 may be used to capture an impedance measurement between any electrode of bottom substrate 110 and the ground reference electrode of top substrate 112. For example, impedance sensing system 170 may be used to scan the reservoir electrodes 120, sample reservoir electrode 122, and droplet operations electrodes 124. An impedance measurement may be stored for each individual electrode of droplet actuator 100. For example, the microfluidic feedback methods of the invention may use impedance measurements taken by impedance sensing system 170 to determine the presence or absence of liquid at certain electrodes of droplet actuator 100, such as at certain reservoir electrodes 120, sample reservoir electrode 122, and certain droplet operations electrodes 124.

Figure 3:
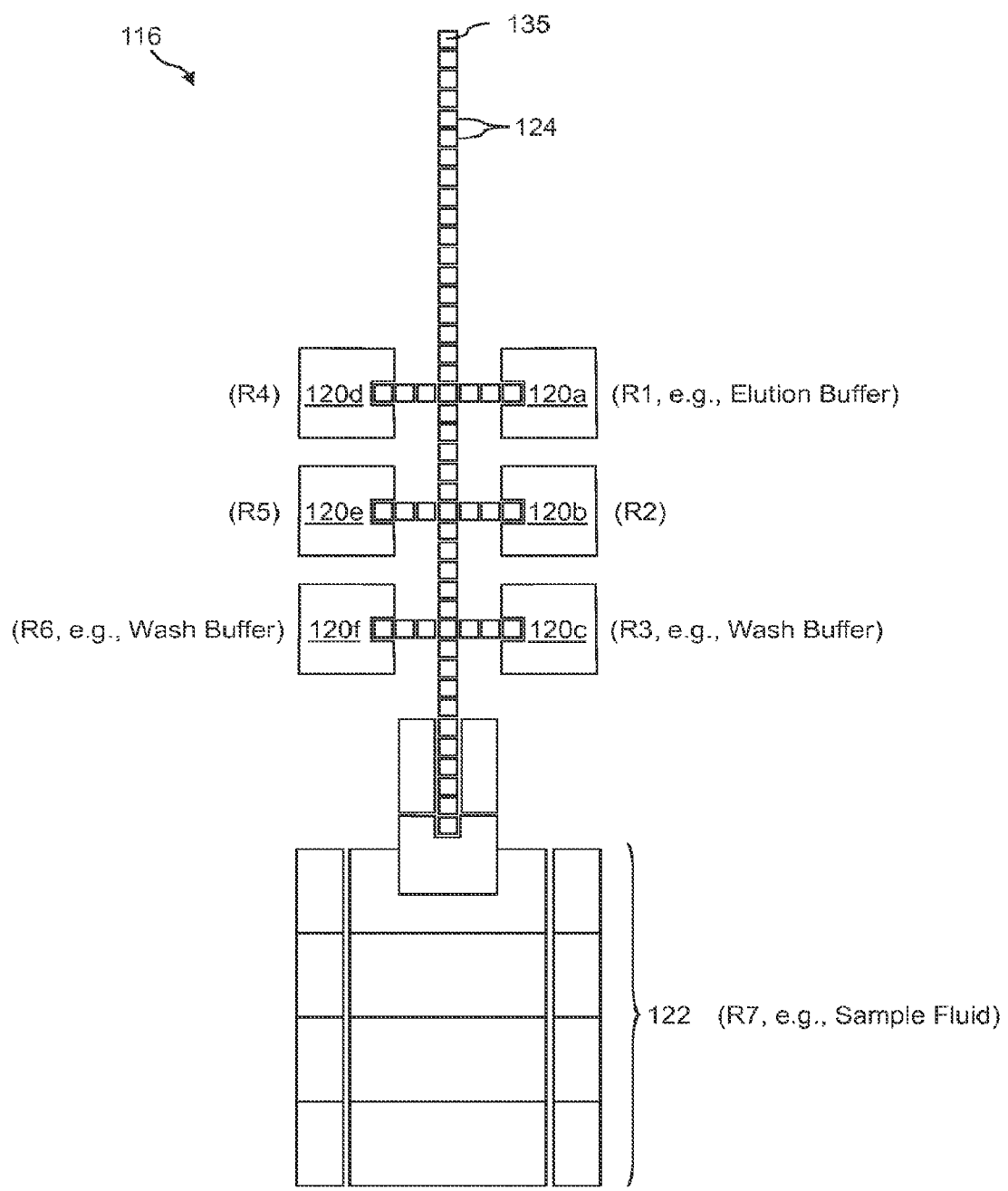
FIG. 3 illustrates a top view of an electrode arrangement of the droplet actuator of FIG. 1.

FIG. 3 illustrates a top view of electrode arrangement 116 of droplet actuator 100 of FIG. 1. Again, electrode arrangement 116 includes reservoir electrodes 120a through 120f and sample reservoir electrode 122, which are arranged in relation to the droplet operations electrodes 124. When droplet actuator 100 is in use, in one example, reservoir R1 at reservoir electrode 120a may be filled with elution buffer solution, reservoir R3 at reservoir electrode 120c may be filled with wash buffer solution, reservoir R3 at reservoir electrode 120f may be also filled with wash buffer solution, and sample reservoir R7 at sample reservoir electrode 122 may be filled with sample fluid.

Figure 4A:
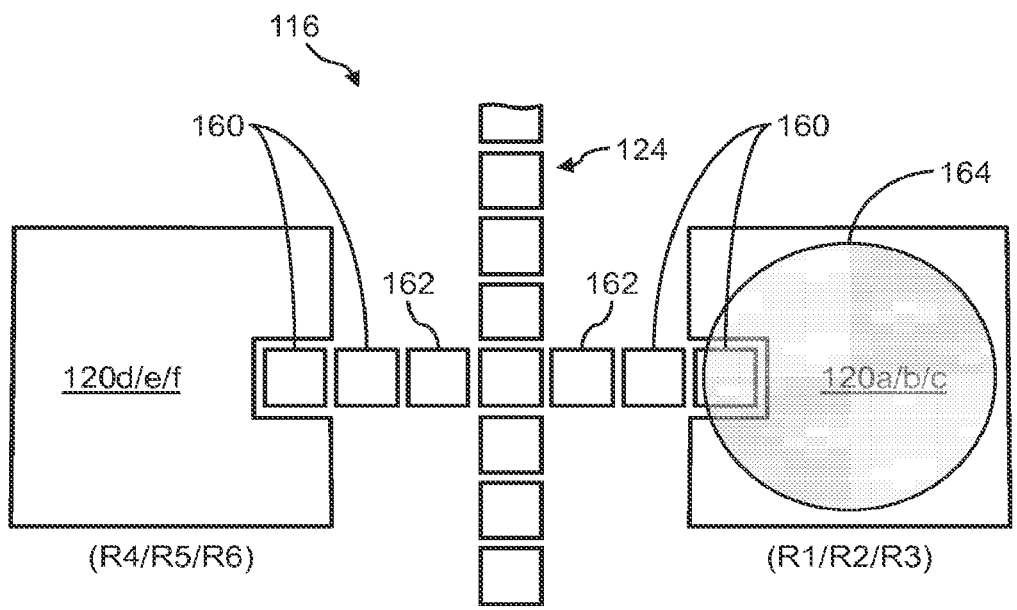
FIGS. 4A and 4B illustrate top views of a portion of the electrode arrangement of the droplet actuator of FIG. 1 and show more details of certain reservoir electrodes.
Figure 4B:
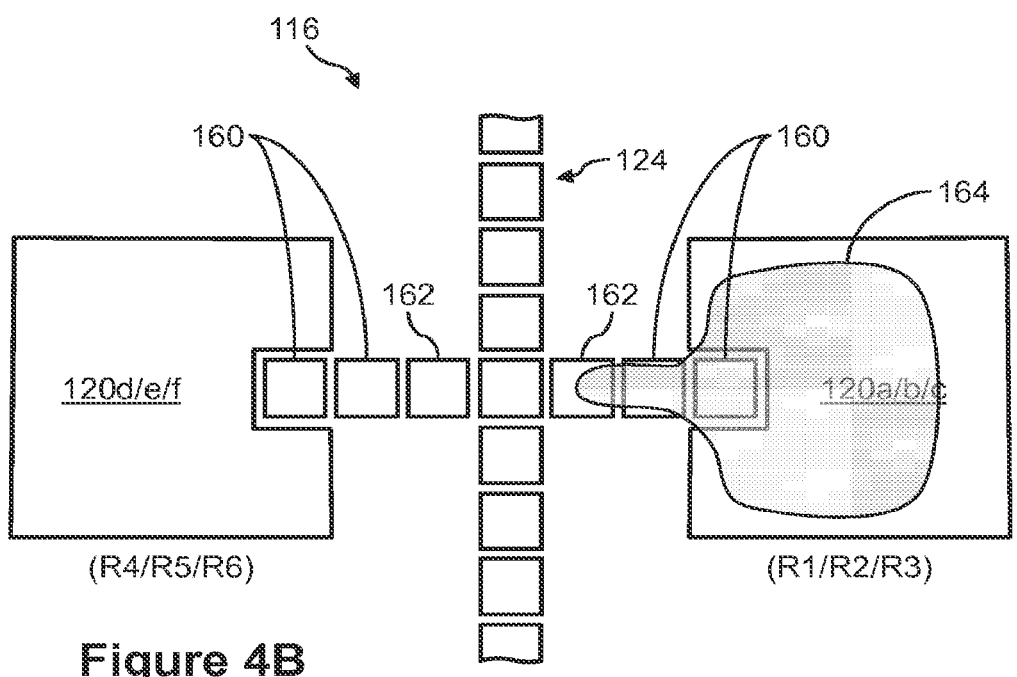

FIGS. 4A and 4B illustrate top views of a portion of electrode arrangement 116 of droplet actuator 100 of FIG. 1 and show more details of reservoir electrodes 120a through 120f of reservoirs R1 through R6, respectively. Each of the reservoirs R1 through R6 may have three electrodes in the path leading to the line of droplet operations electrodes 124. For example, at the dispensing side of each of the reservoirs R1 through R6 may be two dispensing electrodes 160 followed by a gate electrode 162. Gate electrode 162 is nearest the droplet operations electrodes 124.

FIG. 4A shows a volume of fluid 164 atop, for example, reservoir electrode 120a of reservoir R1. In this example, the fluid 164 is positioned substantially within the boundaries of reservoir electrode 120a. However, when there is some volume of fluid atop any reservoir electrode, there is a risk of the fluid drifting toward the line of droplet operations electrodes 124, as shown in FIG. 4B. If the droplet operations electrode 124 near, for example, gate electrode 162 of reservoir R1 happens to be activated, there is a risk of some of this fluid merging with other droplets (not shown) moving along the path of droplet operations electrodes 124. Therefore, a microfluidics feedback mechanism, such as impedance measurements taken of dispensing electrodes 160 and gate electrode 162 of reservoir R1, may be useful to monitor the position of fluid 164 in reservoir R1. If it is detected that that fluid 164 is drifting toward droplet operations electrodes 124, fluid 164 can be pulled back into the reservoir by, for example, activating reservoir electrode 120a of reservoir R1. In this way, any chance of fluid 164 in reservoir R1 interfering with other droplets moving along droplet operations electrodes 124 may be reduced, preferably entirely eliminated. An example of using impedance detection to monitor and/or verify the presence or absence of fluid on, for example, certain electrodes of droplet actuator 100 is described with reference to FIGS. 5A through 17.

FIGS. 5A through 5H illustrate top views of electrode arrangement 116 of droplet actuator 100 of FIG. 1 and an example of an electrode activation sequence of certain impedance detection operations. The electrode activation sequence and impedance detection operations of FIGS. 5A through 5H is one example of a microfluidics feedback mechanism in a droplet actuator.

Figure 5A:
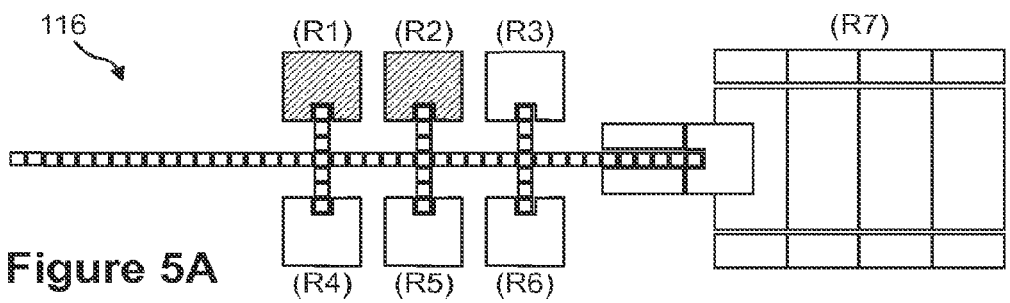
FIGS. 5A through 5H illustrate top views of the electrode arrangement of the droplet actuator of FIG. 1 and examples of the electrode activation during certain impedance detection operations.

Referring to FIG. 5A, reservoir electrode 120a of reservoir R1 and reservoir electrode 120b of reservoir R2 are activated and an impedance measurement is taken of reservoir electrode 120a and reservoir electrode 120b (together) using, for example, impedance sensing system 170 of FIG. 2.

Figure 5B:
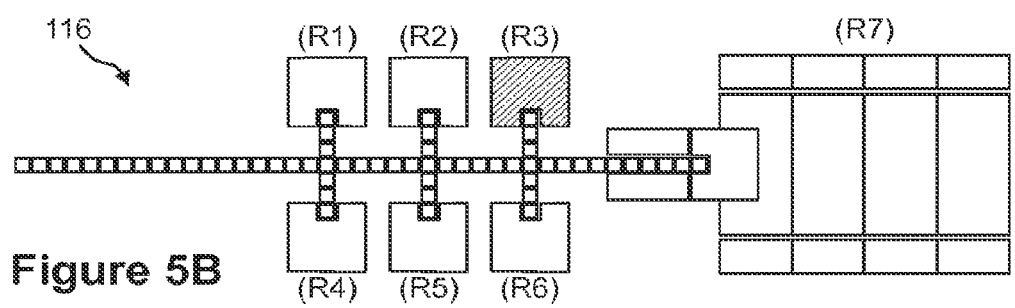

Referring to FIG. 5B, reservoir electrode 120c of reservoir R3 is activated and an impedance measurement is taken of reservoir electrode 120c using impedance sensing system 170 of FIG. 2.

Figure 5C:
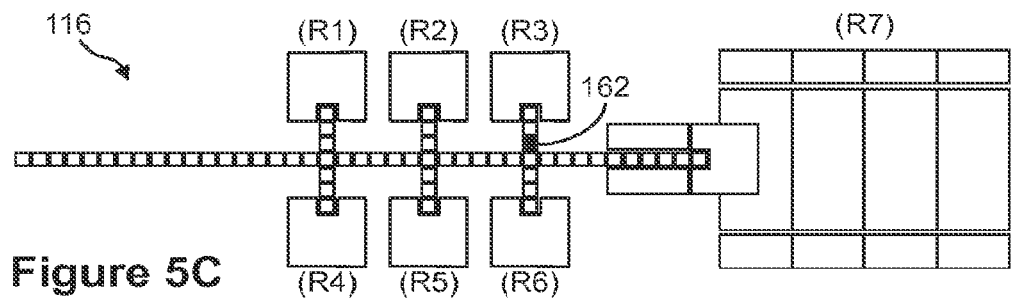

Referring to FIG. 5C, gate electrode 162 of reservoir R3 is activated and an impedance measurement is taken of this gate electrode 162 using impedance sensing system 170 of FIG. 2.

Figure 5D:
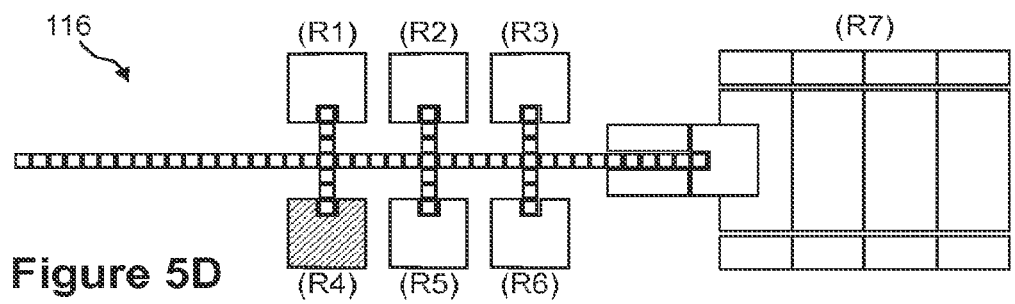

Referring to FIG. 5D, reservoir electrode 120d of reservoir R4 is activated and an impedance measurement is taken of reservoir electrode 120d using impedance sensing system 170 of FIG. 2.

Figure 5E:
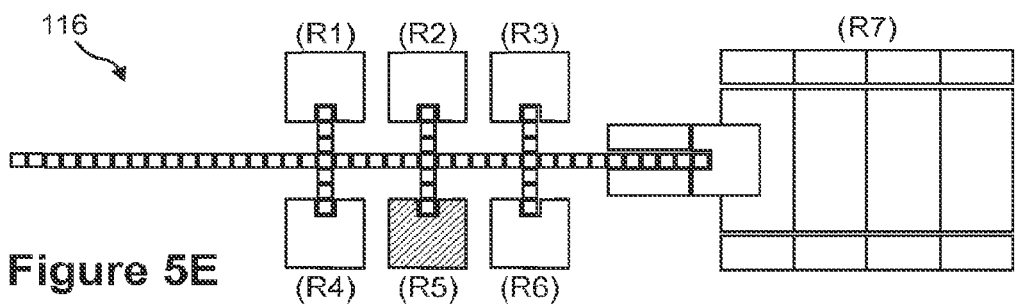

Referring to FIG. 5E, reservoir electrode 120e of reservoir R5 is activated and an impedance measurement is taken of reservoir electrode 120e using impedance sensing system 170 of FIG. 2.

Figure 5F:
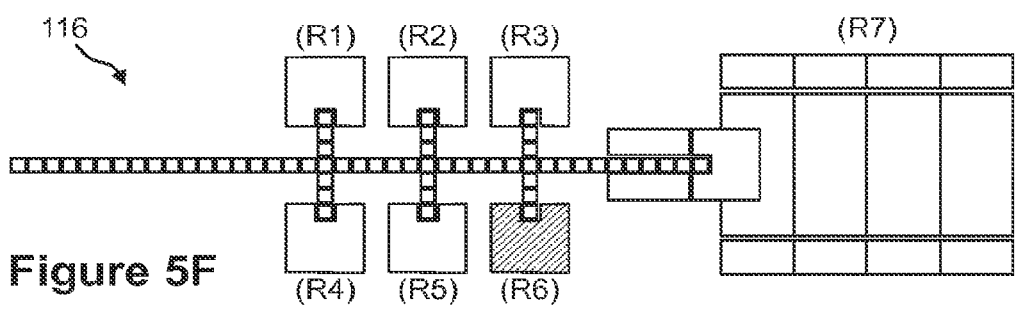

Referring to FIG. 5F, reservoir electrode 120f of reservoir R6 is activated and an impedance measurement is taken of reservoir electrode 120f using impedance sensing system 170 of FIG. 2.

Figure 5G:
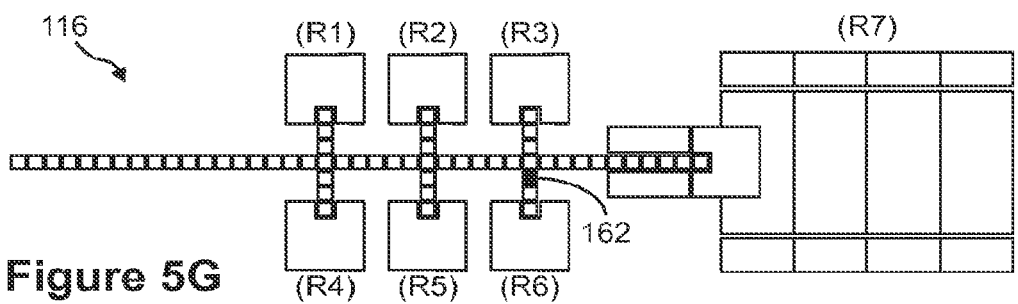

Referring to FIG. 5G, gate electrode 162 of reservoir R6 is activated and an impedance measurement is taken of this gate electrode 162 using impedance sensing system 170 of FIG. 2.

Figure 5H:
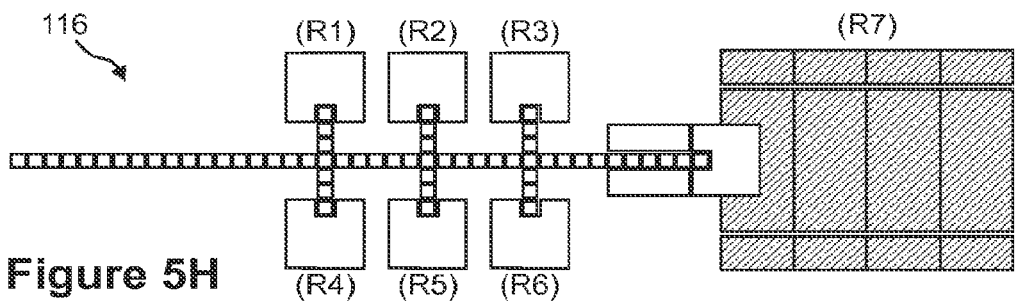

Referring to FIG. 5H, sample reservoir electrode 122 of sample reservoir R7 is activated and an impedance measurement is taken of sample reservoir electrode 122 using impedance sensing system 170 of FIG. 2.

With respect to FIGS. 5A through 5H, there is an expected difference in the impedance measurement readings when filler oil only is at the electrode vs. when fluid is present at the electrode. Examples of the results of multiple impedance detection operations of droplet actuator 100 are shown with reference to FIGS. 6 through 16.

FIGS. 6 through 16 illustrate graphs of examples of impedance measurements taken of certain electrodes of droplet actuator 100 of FIG. 1 and under the various conditions and with the electrode activation shown in FIGS. 5A through 5H. For example, a set of impedance measurements were taken of certain electrodes of droplet actuator 100 with filler oil only at the electrodes of interest. Then, another set of impedance measurements were taken of certain electrodes of droplet actuator 100 with fluid at the electrodes. The graphs shown in FIGS. 6 through 16 are provided to show the contrast between the impedance measurements taken under the two different conditions, thereby demonstrating the use of impedance detection operations as a suitable microfluidic feedback mechanism for determining the presence or absence of fluid at any electrode of interest.

Figure 6:
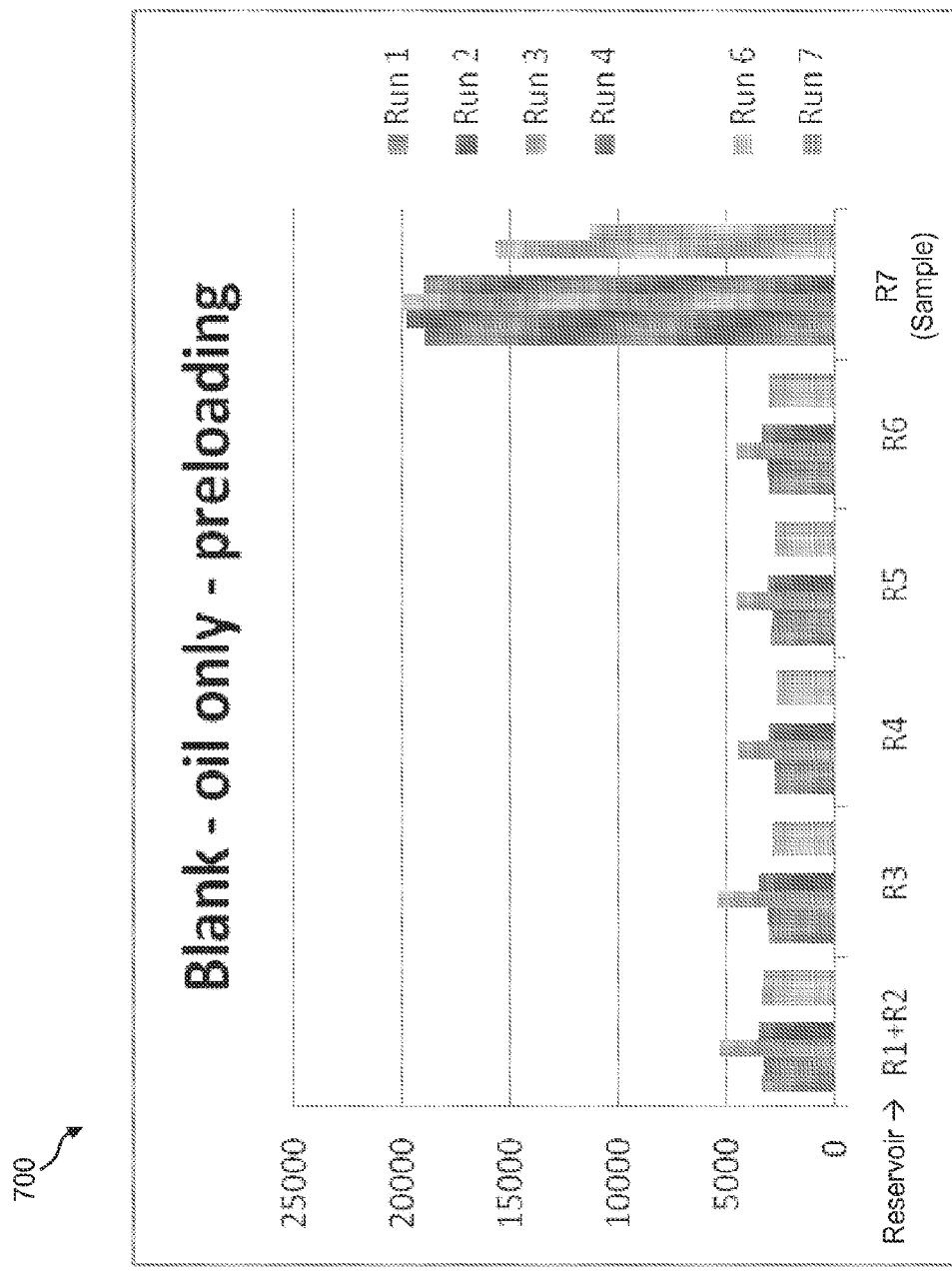
FIGS. 6 through 16 illustrate graphs of examples of impedance measurements taken of certain electrodes of the droplet actuator of FIG. 1 and under various conditions.

Referring to FIG. 6, a bar graph 700 shows the impedance measurements acquired with filler oil only in the gap of droplet actuator 100. That is, the gap of droplet actuator 100 is loaded with filler oil and this set of impedance measurements is acquired prior to loading droplet actuator 100 with any other fluids. Therefore, bar graph 700 shows pre-liquid loading impedance values at certain reservoirs of droplet actuator 100. The set of impedance readings shown in bar graph 700 may be referred to as the "blank values." By way of example, multiple detection operations (or runs) were performed and plotted in bar graph 700. For example, seven detection operations (runs 1 through 7) were performed and recorded with respect to reservoir R1 and reservoir R2 (see FIG. 5A), reservoir R3 (see FIG. 5B), reservoir R4 (see FIG. 5D), reservoir R5 (see FIG. 5E), reservoir R6 (see FIG. 5F), and sample reservoir R7 (see FIG. 5H) of droplet actuator 100. Run 5 is not shown due to technical problem during the run. Runs 1 through 7 may be the results of detection operations performed on one or more instances of droplet actuator 100. The impedance values in bar graph 700 and in subsequent bar graphs and plots are given in ohms.

Bar graph 700 shows some variation in the blank values of sample reservoir R7. During runs 1 through 7 an air bubble is intentionally left in sample reservoir R7. A variation in the position of this bubble from one run to the next may contribute to the variation in the blank values. Additionally, the presence of the two openings in top substrate 112 at sample reservoir R7 (i.e., input ports 128 and 130) may contribute to the variation in the blank values of sample reservoir R7.

Figure 7:
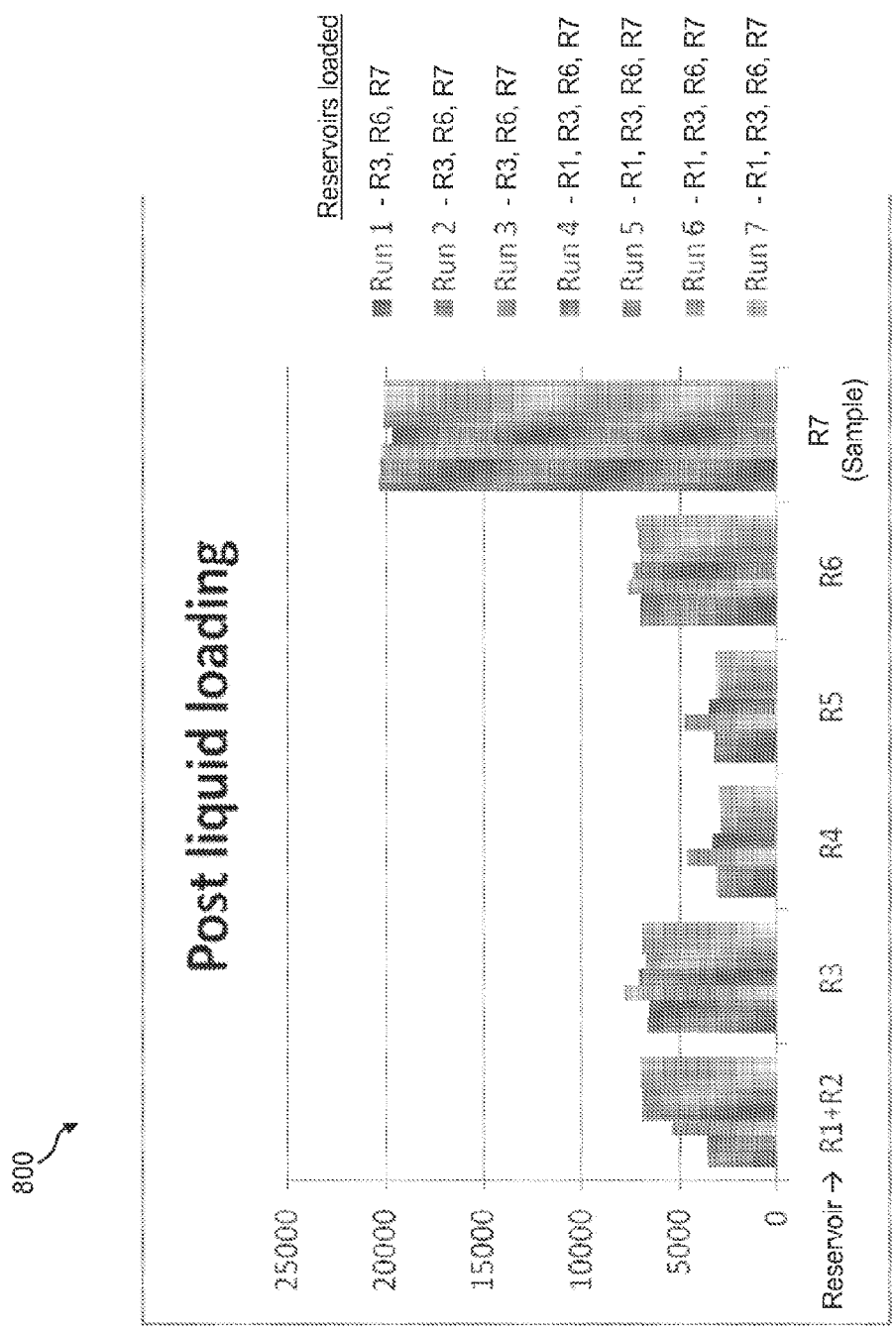

In contrast to the pre-liquid loading impedance values of bar graph 700, FIG. 7 shows a bar graph 800 that shows the impedance measurements acquired with fluid present at certain reservoirs of droplet actuator 100. That is, bar graph 800 shows post-liquid loading impedance values at certain reservoirs of droplet actuator 100. For example, bar graph 800 shows a plot of another set of seven detection operations (runs 1 through 7). In runs 1, 2, and 3, reservoir R3, reservoir R6, and sample reservoir R7 are loaded with a certain amount of fluid. In runs 4, 5, 6, and 7, reservoir R1, reservoir R3, reservoir R6, and sample reservoir R7 are loaded with a certain amount of fluid.

Reservoir R3, reservoir R6, and sample reservoir R7 are used in all runs, while reservoir R1 is only used in runs 4 through 7. The impedance values at reservoir R3 and reservoir R6, which are used in all runs, are consistent across runs. The impedance value at sample reservoir R7 is consistent across runs, unlike the blank values of sample reservoir R7 shown in bar graph 700 of FIG. 6.

Figure 8:
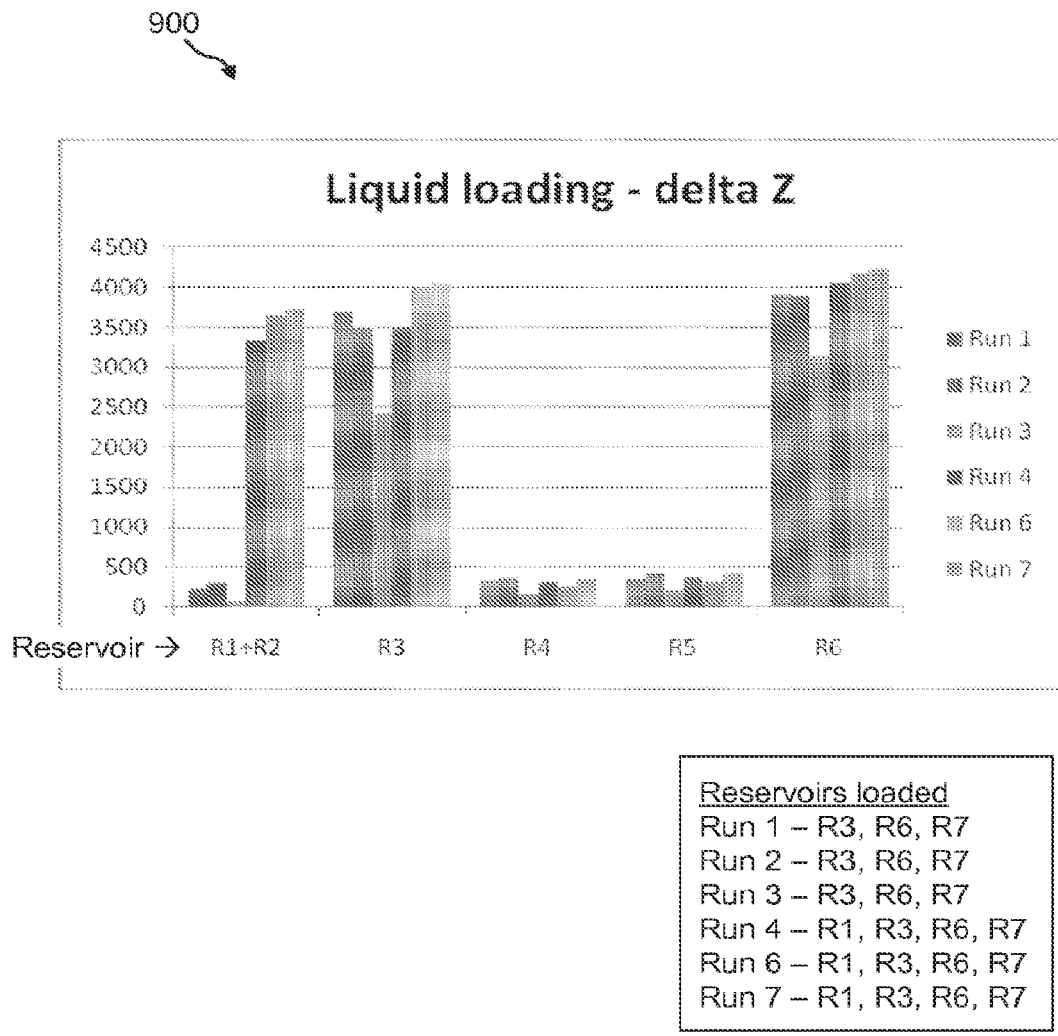

Referring to FIG. 8, a bar graph 900 shows a plot of the liquid loading delta Z values. That is, bar graph 900 shows the difference (called delta Z) between the pre-liquid loading impedance values of bar graph 700 of FIG. 6 and the post-liquid loading impedance values of bar graph 800 of FIG. 7. Bar graph 900 indicates noticeable delta Z values between reservoirs that are loaded with fluid and reservoirs that are not loaded, which shows clear separation between loaded and empty reservoirs.

Figure 9A:
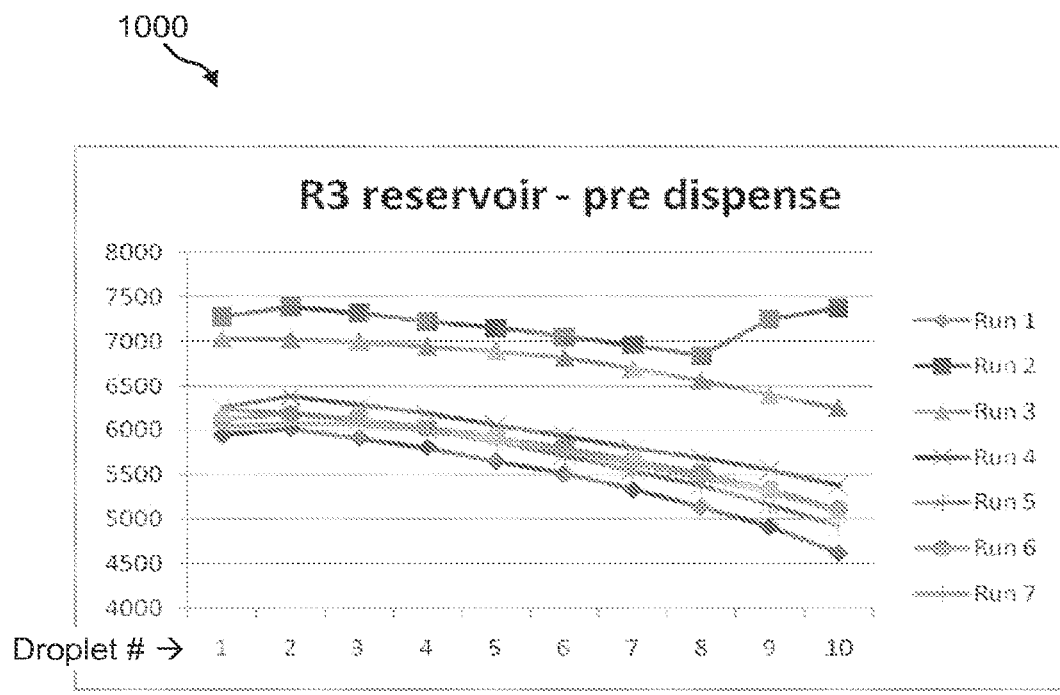
Figure 9B:
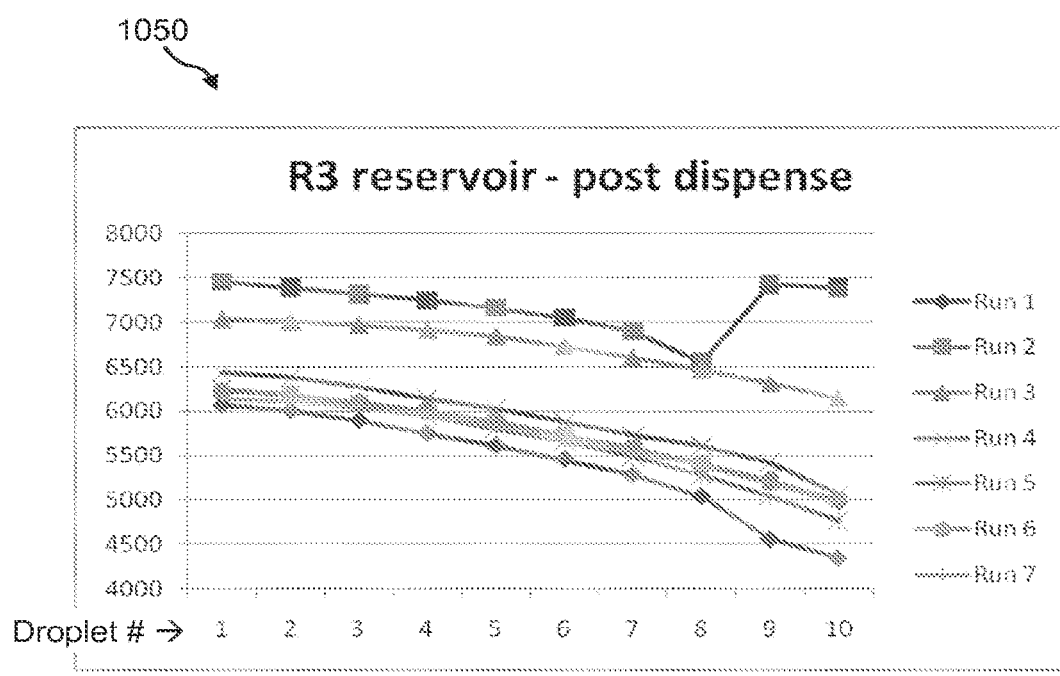

Referring to FIG. 9A, a plot 1000 of the pre-dispense impedance values at reservoir R3 is shown with respect to 10 droplets. That is, 10 droplets are dispensed from reservoir R3 of droplet actuator 100 and an impedance measurement is taken on reservoir electrode 120*c* of reservoir R3 just prior to the dispensing of each droplet. By contrast and referring now to FIG. 9B, a plot 1050 of the post-dispense impedance values at reservoir R3 is shown with respect to the same 10 droplets. That is, when the 10 droplets are dispensed from reservoir R3 of droplet actuator 100, an impedance measurement is taken on reservoir electrode 120*c* of reservoir R3 just after the dispensing of each droplet. Again, seven runs of pre-dispense impedance values and post-dispense impedance values are collected. The seven runs may include one or more instances of droplet actuator 100.

Referring to plot 1000 of FIG. 9A, there may be some variation in the pre-dispense impedance values of the droplet #1 of runs 1 through 7, which may be due to variation in the position of the fluid that is loaded in reservoir R3. This variation is not seen in the post-dispense curves of plot 1050 of FIG. 9B.

Figure 10:
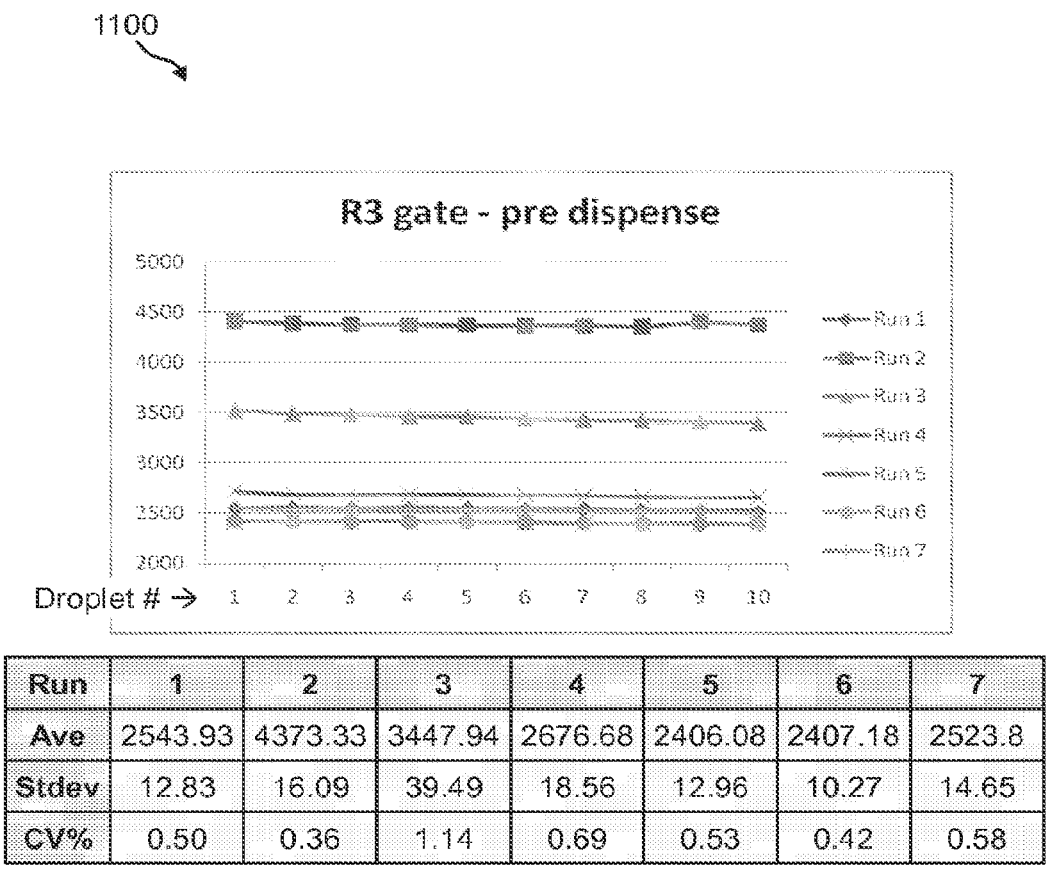

Referring to FIG. 10, a plot 1100 of the pre-dispense impedance values at gate electrode 162 of reservoir R3 is shown with respect to 10 droplets. That is, 10 droplets are dispensed from reservoir R3 of droplet actuator 100. As each droplet passes atop the gate electrode 162 of reservoir R3 an impedance measurement is acquired. FIG. 10 also shows a table that includes for each of the seven runs (1) the average pre-dispense impedance value of the 10 droplets, (2) the standard deviation, and (3) the percent capacitance-voltage (CV %).

Figure 11:
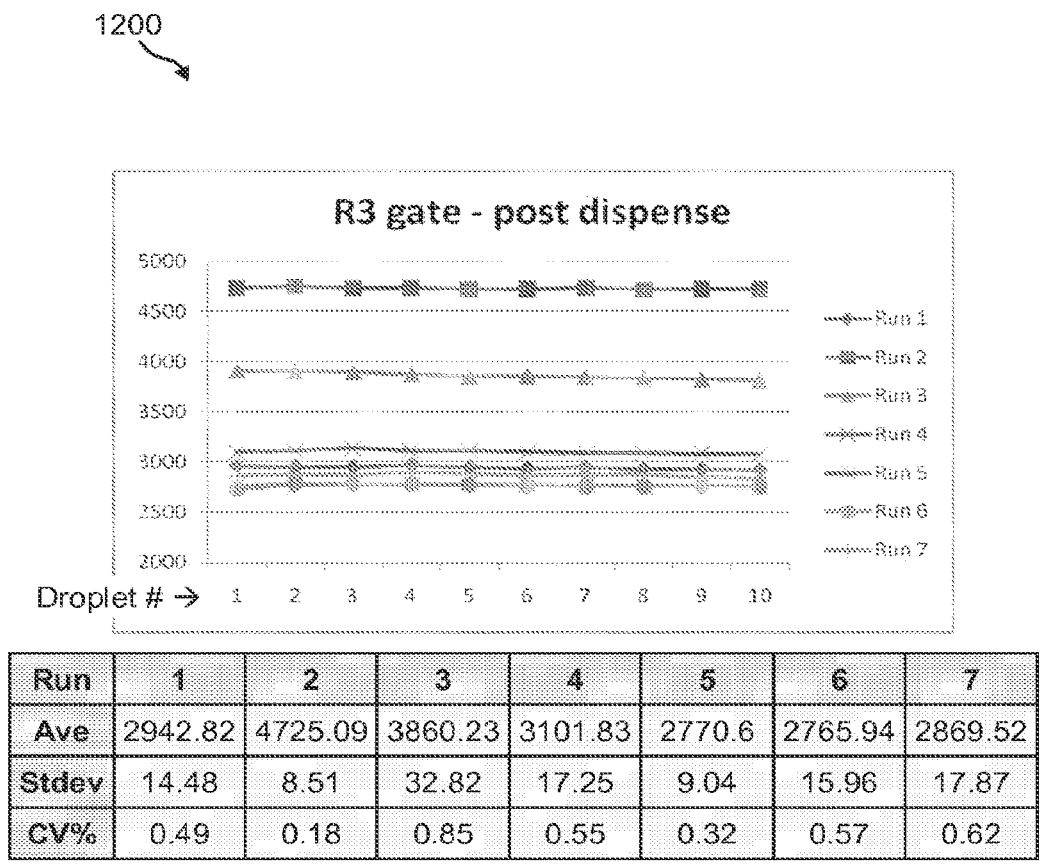

By contrast and referring now to FIG. 11, a plot 1200 of the post-dispense impedance values at gate electrode 162 of reservoir R3 is shown with respect to the same 10 droplets. That is, 10 droplets are dispensed from reservoir R3 of droplet actuator 100. As each of the 10 droplets is transported off of the gate electrode 162 of reservoir R3 an impedance measurement is acquired. FIG. 11 also shows a table that includes for each of the seven runs (1) the average post-dispense impedance value of the 10 droplets, (2) the standard deviation, and (3) the CV %.

Figure 12:
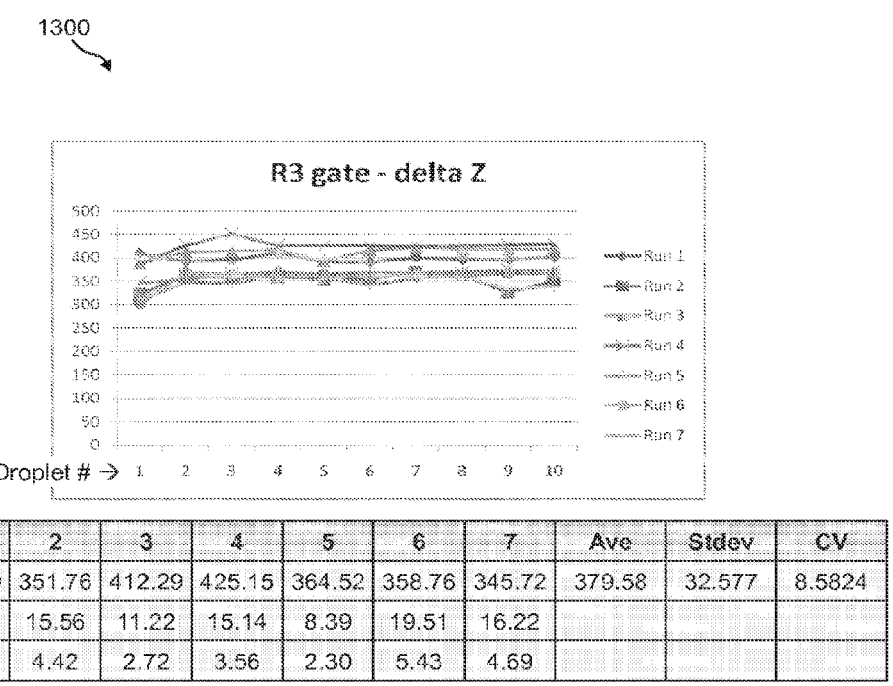

Referring to FIG. 12, a bar graph 1300 shows a plot of the delta Z values of gate electrode 162 of reservoir R3. That is, bar graph 1300 shows the difference (called delta Z) between the pre-dispense impedance values of bar graph 1100 of FIG. 10 and the post-dispense impedance values of bar graph 1200 of FIG. 11. FIG. 12 also shows a table that includes for each of the seven runs (1) the average delta Z value, (2) the standard deviation of the delta Z values, and (3) the CV % of the delta Z values. Additionally, the table shows the average delta Z value of all runs, the standard deviation of the delta Z value of all runs, and the CV % of the delta Z value of all runs.

Figure 13A:
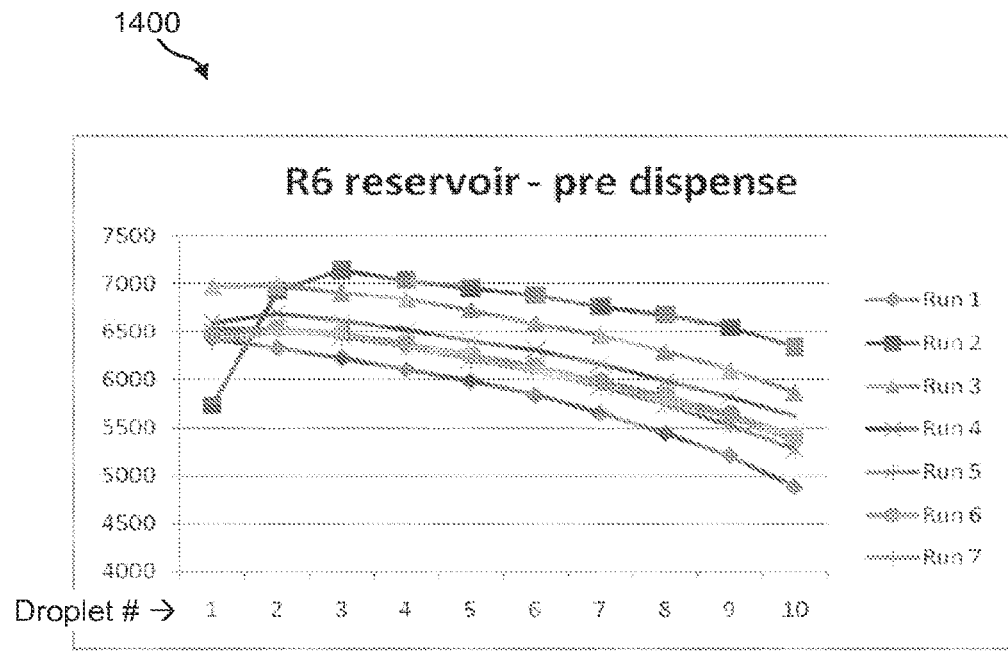
Figure 13B:
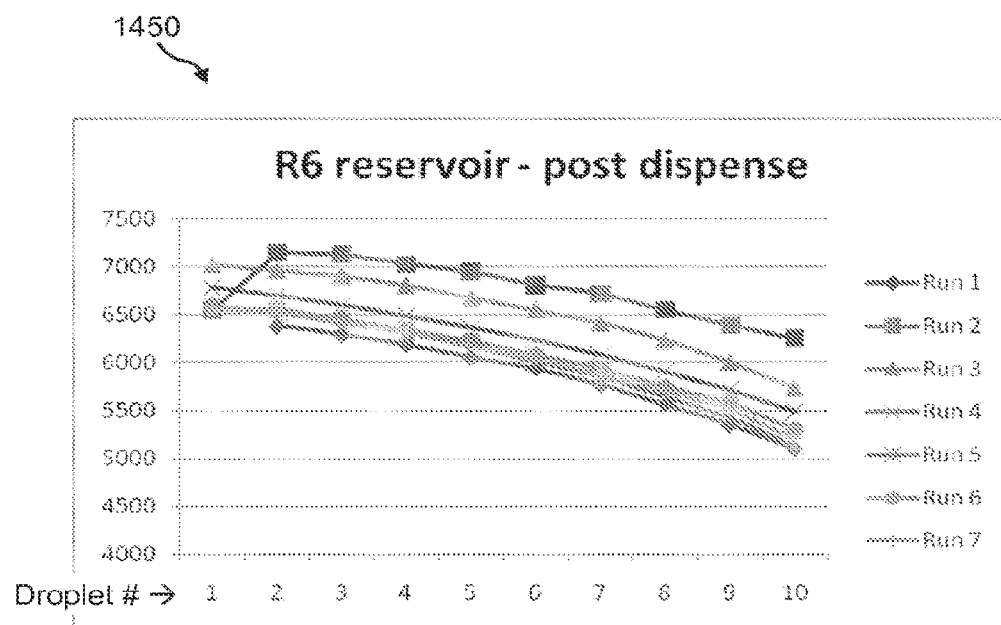

Referring to FIG. 13A, a plot 1400 of the pre-dispense impedance values at reservoir R6 is shown with respect to 10 droplets. That is, 10 droplets are dispensed from reservoir R6 of droplet actuator 100 and an impedance measurement is taken on reservoir electrode 120*f* of reservoir R6 just prior to the dispensing of each droplet. By contrast and referring now to FIG. 13B, a plot 1450 of the post-dispense impedance values at reservoir R6 is shown with respect to the same 10 droplets. That is, when the 10 droplets are dispensed from reservoir R6 of droplet actuator 100, an impedance measurement is taken on reservoir electrode 120*f* of reservoir R6 just after the dispensing of each droplet. Again, seven runs of pre-dispense impedance values and post-dispense impedance values are collected. The seven runs may include one or more instances of droplet actuator 100.

Referring to plot 1400 of FIG. 13A, there may be some variation in the pre-dispense impedance values of the droplet #1 of runs 1 through 7, which may be due to variation in the position of the fluid that is loaded in reservoir R6. This variation is not seen in the post-dispense curves of plot 1450 of FIG. 13B.

Figure 14:
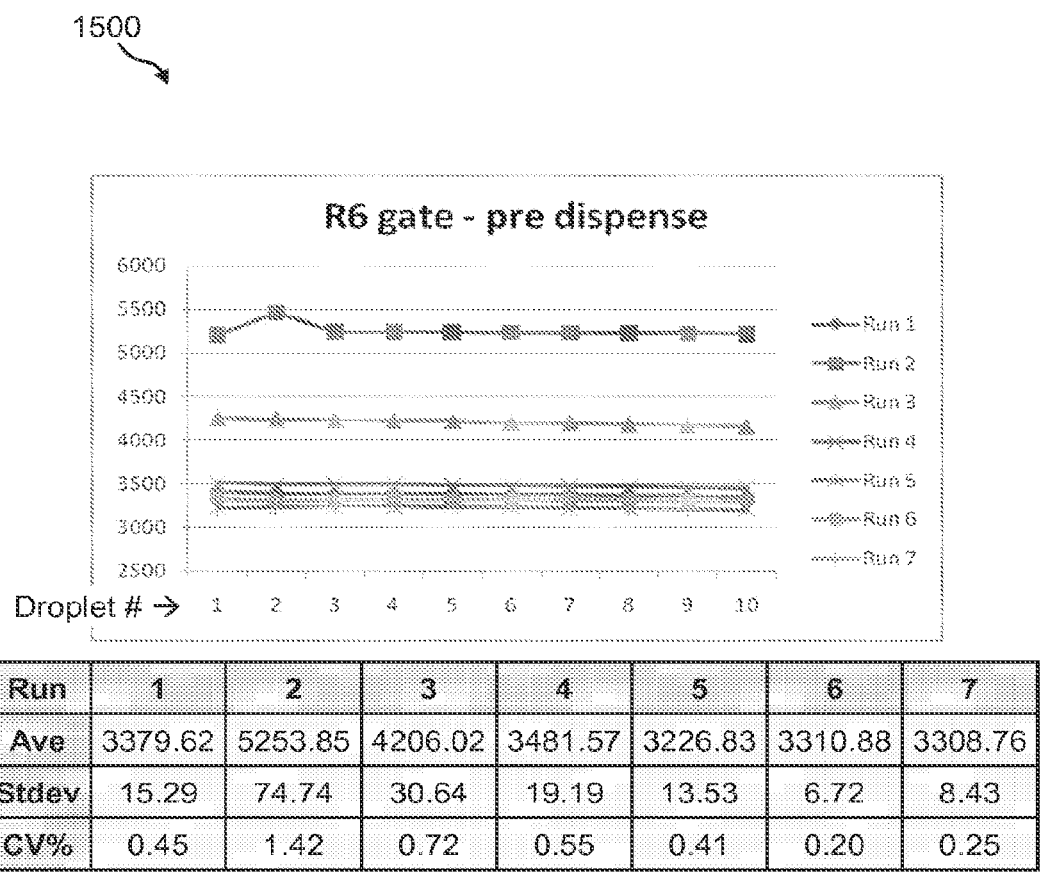

Referring to FIG. 14, a plot 1500 of the pre-dispense impedance values at gate electrode 162 of reservoir R6 is shown with respect to 10 droplets. That is, 10 droplets are dispensed from reservoir R6 of droplet actuator 100. As each droplet passes atop the gate electrode 162 of reservoir R6 an impedance measurement is acquired. FIG. 14 also shows a table that includes for each of the seven runs (1) the average pre-dispense impedance value of the 10 droplets, (2) the standard deviation, and (3) the CV %.

Figure 15:
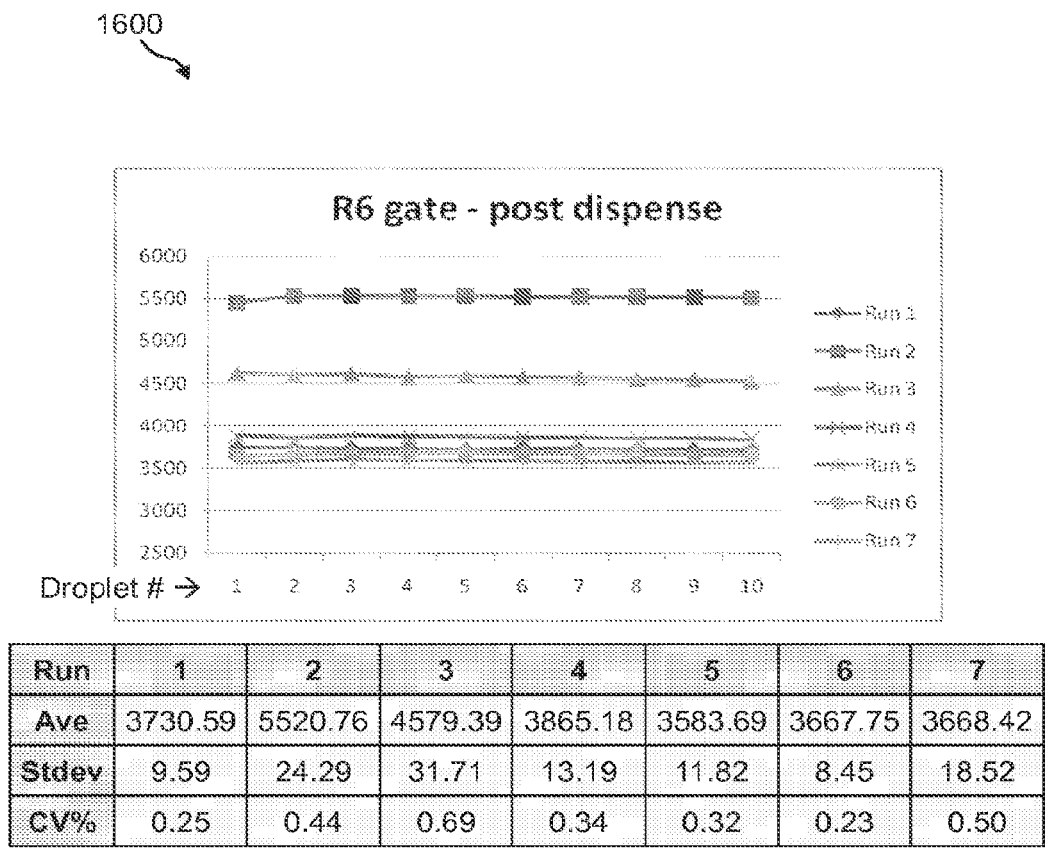

By contrast and referring now to FIG. 15, a plot 1600 of the post-dispense impedance values at gate electrode 162 of reservoir R6 is shown with respect to the same 10 droplets. That is, 10 droplets are dispensed from reservoir R6 of droplet actuator 100. As each of the 10 droplets is transported off of the gate electrode 162 of reservoir R6 an impedance measurement is acquired. FIG. 15 also shows a table that includes for each of the seven runs (1) the average post-dispense impedance value of the 10 droplets, (2) the standard deviation, and (3) the CV %.

Figure 16:
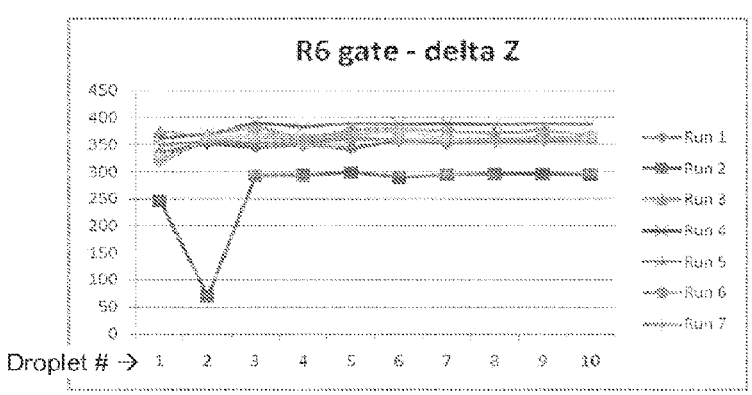

Referring to FIG. 16, a bar graph 1700 shows a plot of the delta Z values of gate electrode 162 of reservoir R6. That is, bar graph 1700 shows the difference (called delta Z) between the pre-dispense impedance values of plot 1500 of FIG. 14 and the post-dispense impedance values of plot 1600 of FIG. 15. FIG. 16 also shows a table that includes for each of the seven runs (1) the average delta Z value, (2) the standard deviation of the delta Z values, and (3) the CV % of the delta Z values. Additionally, the table shows the average delta Z value of all runs, the standard deviation of the delta Z value of all runs, and the CV % of the delta Z value of all runs. Referring again to FIGS. 1 through 16, other variables may effect impedance measurements. For example, temperature and/or droplet size may have an effect on the impedance measurements.

6.2.1 Impedance Sensing Circuits

Currently, the impedance sensing circuit that is used with a droplet actuator may utilize an impedance signal that is superimposed on a reference voltage. The reference voltage source is typically a switching power supply, which is a high voltage AC power supply for providing the electrowetting voltage (e.g., about 300 volts) to the electrodes of a droplet actuator. The stability of the high voltage AC power supply is critical because it is used as the impedance reference measurement voltage. However, a drawback of this arrangement is that switching power supplies may be noisy. For example, in a droplet actuator application, a ripple voltage of about 1 to about 3 volts may be present on the about 300V output. While this ripple voltage is of little or no consequence when performing droplet operations, it may contribute to certain inaccuracies during impedance detection operations. Voltage regulators, such as linear regulators, may be used to smooth out the ripple. However, voltage regulators are not completely effective in eliminating the noise, consume a large amount of power at high voltages (e.g., about 300 volts), and add expense and complexity to the circuit. Therefore, the impedance sensing circuit of the present invention provides a novel approach that does not rely on a voltage regulator to ensure stability of the high voltage AC power supply during impedance detection operations. For example, the impedance sensing circuit includes an electrowetting voltage suppression mechanism for reducing noise during impedance detection operations, which is described with reference to FIGS. 17 and 18.

Figure 17:
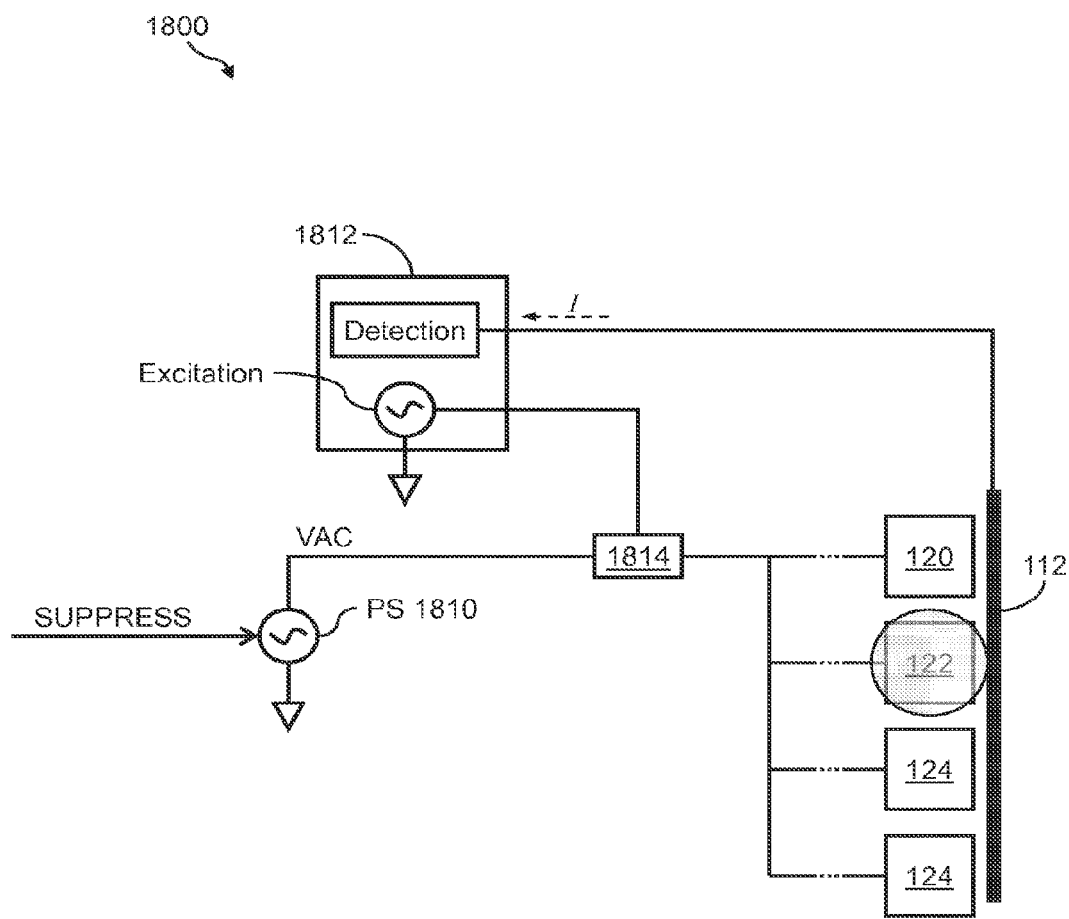
FIG. 17 illustrates a schematic diagram of an example of an impedance sensing circuit of a droplet actuator that includes an electrowetting voltage suppression mechanism for reducing noise.

FIG. 17 illustrates a schematic diagram of an example of an impedance sensing circuit 1800 of a droplet actuator that includes an electrowetting voltage suppression mechanism for reducing noise. Impedance sensing circuit 1800 may include a power supply (PS) 1810. PS 1810 provides the electrowetting voltage source that is needed to perform droplet operations. In one example, PS 1810 is a 300 VAC power supply. Impedance sensing circuit 1800 may also include an impedance sensing system 1812. Impedance sensing system 1812 includes an excitation portion for generating an excitation signal and a detection portion for processing the return signal.

The excitation signal of impedance sensing system 1812 is superimposed on the output of PS 1810 via, for example, a voltage adder 1814. The output of voltage adder 1814 may be selectively connected to any electrode of a droplet actuator. By way of example, FIG. 17 shows the output of voltage adder 1814 selectively connected to any reservoir electrode 120, sample reservoir electrode 122, and/or any droplet operations electrode 124 of droplet actuator 100 of FIGS. 1, 2, and 3. During impedance detection operations, the return path (with respect to the electrodes) to the detection portion of impedance sensing system 1812 is the electrical ground plane of the top substrate, such as top substrate 112 of droplet actuator 100.

An aspect of the impedance sensing circuit 1800 of the invention is that it also includes a mechanism for suppressing the output of PS 1810 during impedance detection operations, thereby reducing, preferably entirely eliminating, noise on the output of PS 1810. In this way, the accuracy and/or reliability of impedance measurements taken by impedance sensing system 1812 may be improved. For example, the switching action of PS 1810, which is the source of the noise, is suppressed (i.e., stopped) during impedance detection operations. Impedance sensing circuit 1800 includes a SUPPRESS signal that feeds the control of PS 1810 for disabling the switching action thereof during impedance detection operations. More details of the suppression mechanism of the invention are described with reference to FIG. 18.

Figure 18:
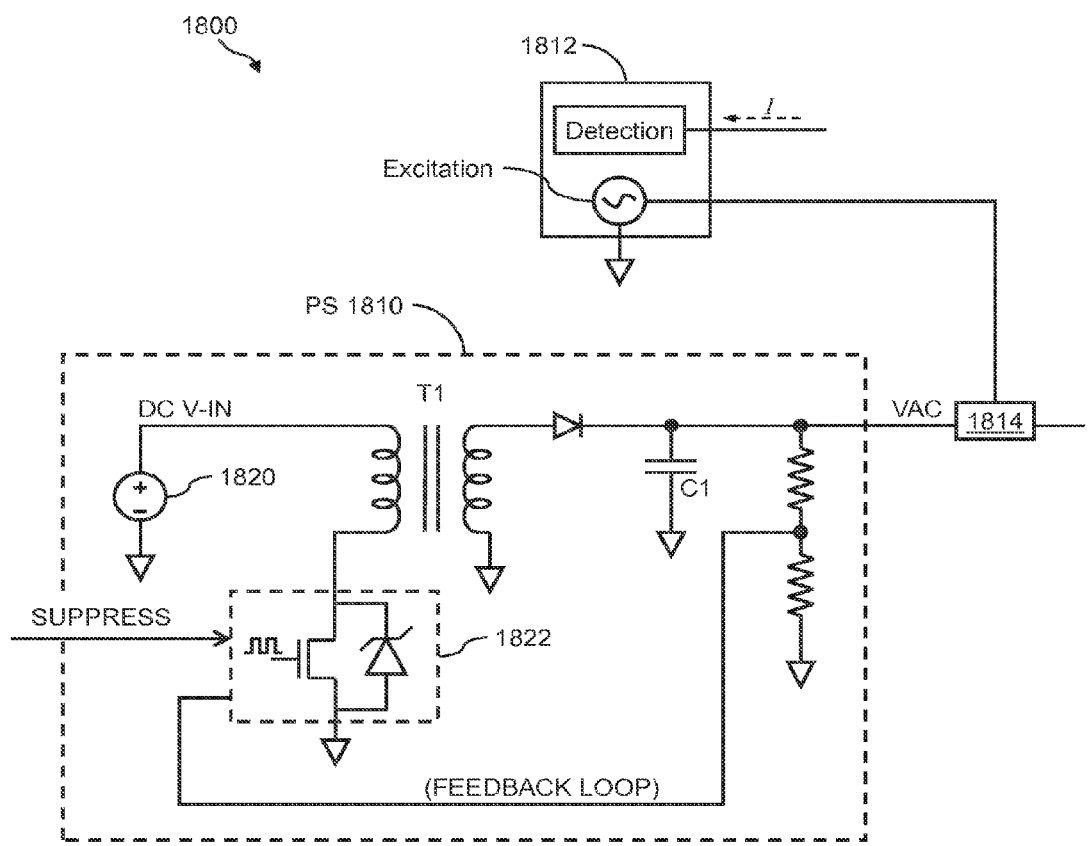
FIG. 18 illustrates a schematic diagram showing more details of the impedance sensing circuit of FIG. 17 that includes the electrowetting voltage suppression mechanism.

FIG. 18 illustrates a schematic diagram showing more details of impedance sensing circuit 1800 of FIG. 17 that includes the electrowetting voltage suppression mechanism. In particular, FIG. 18 shows more details of an example of the voltage suppression mechanism with respect to PS 1810. For example, PS 1810 includes a direct current (DC) power source 1820, a transformer T1, and a switching circuit 1822. DC power source 1820 and switching circuit 1822 are arranged in relation to the primary of transformer T1. Switching circuit 1822 may include any solid state switch device, such as an NMOS switch. In one example, the solid state switch device may be toggled off and on by a square wave from an oscillator (not shown). Switching circuit 1822 is used to develop a low voltage AC signal at the primary of transformer T1. A standard rectifier circuit at the secondary of transformer T1 provides an output voltage (VAC) that is a higher voltage than the input voltage. PS 1810 also includes a tank capacitor C1 at VAC (i.e., at the secondary of transformer T1). A feedback loop is provided from VAC back to switching circuit 1822.

In operation, the SUPPRESS signal feeds switching circuit 1822 of PS 1810. For example, when the SUPPRESS signal is active the switching action of the solid state switch device of PS 1810 is stopped. In one example, during impedance detection operations, the SUPPRESS signal is used to stop the switching action of PS 1810 for several milliseconds while the impedance measurements are taking place. Stopping the switching action reduces, preferably entirely eliminates, any noise (i.e., voltage ripple) on the output of PS 1810. At the same time, tank capacitor C1 stores the charge at the output of PS 1810. In this way, the output voltage of PS 1810 is maintained while the switching action of PS 1810 is being suppressed via the SUPPRESS signal. Once impedance measurements are complete, the SUPPRESS signal may be deactivated and the normal operation of PS 1810 resumes.

An example of a method of using impedance sensing circuit 1800 of the invention may include, but is not limited to, the following steps—(1) activate the SUPPRESS signal and, thereby, stop the switching action of PS 1810; (2) activate the excitation portion of impedance sensing system 1812 and, thereby, generate an excitation signal to any one or more electrodes of interest; (3) process the return signal(s) using the detection portion of impedance sensing system 1812; (4) correlate the impedance measurements to the presence and/or absence of fluid at the one or more electrodes of interest; (5) deactivate the excitation portion of impedance sensing system 1812; and (6) deactivate the SUPPRESS signal and, thereby, resume normal operation of PS 1810.

Figure 19:
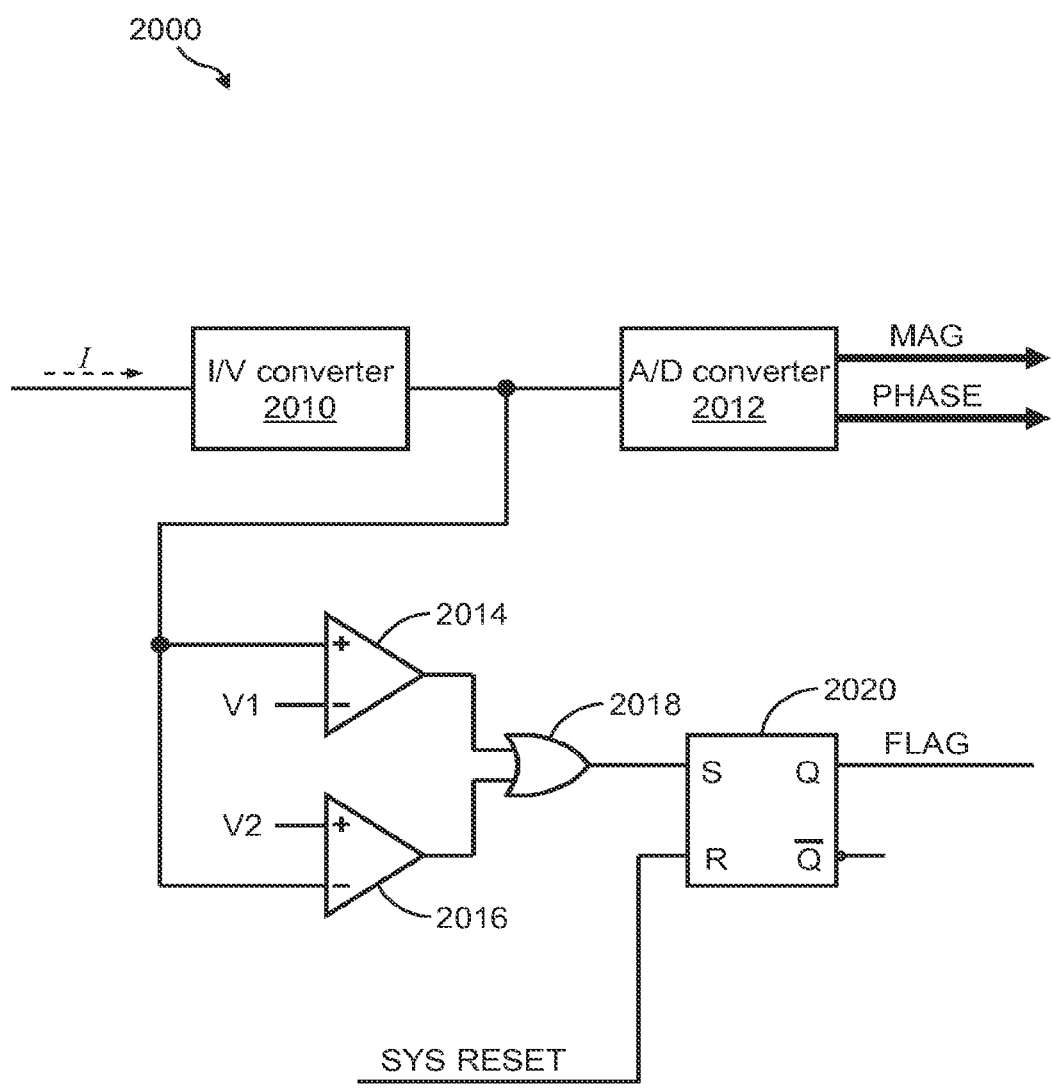
FIG. 19 illustrates a schematic diagram of the detection circuit of an impedance sensing system that includes a feature for logging a saturation condition of the response signal.
Figure 20:
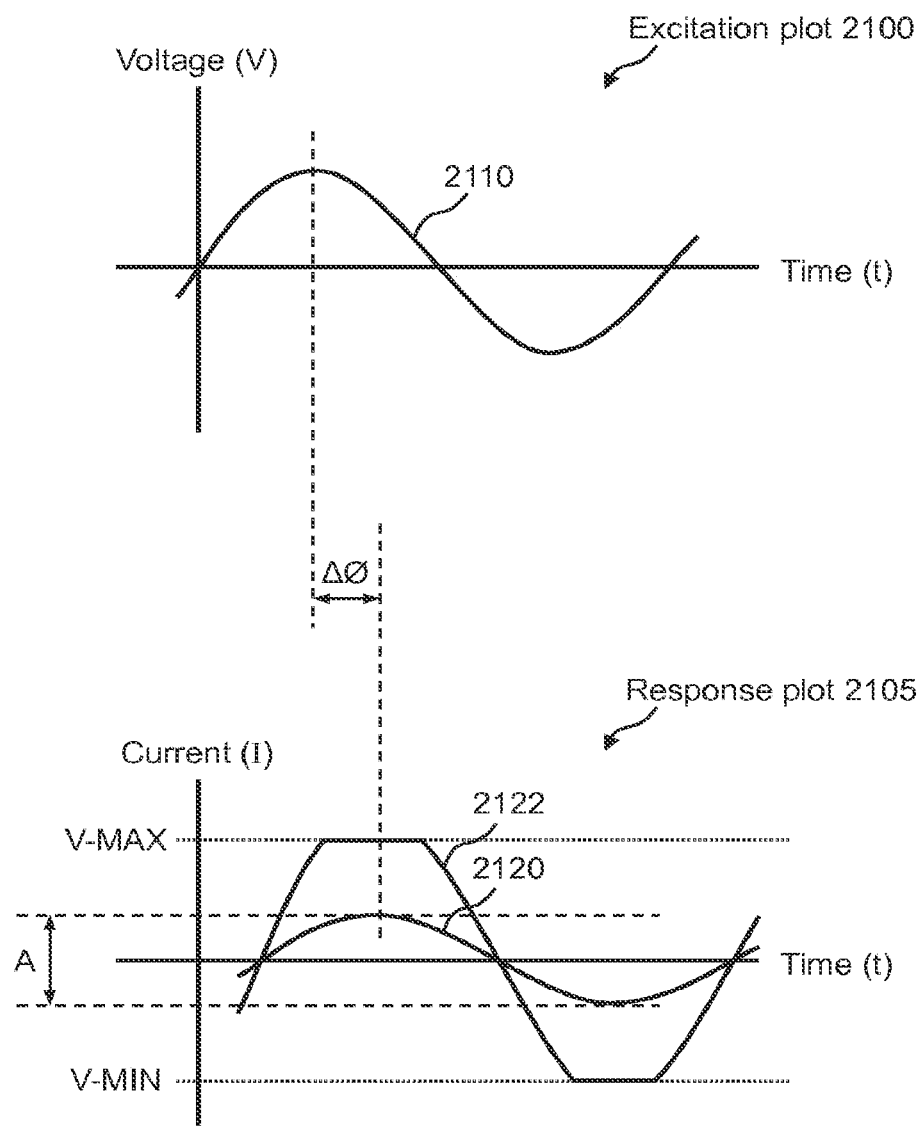
FIG. 20 illustrates an example of an excitation plot in relation to a response plot of an impedance sensing system showing a response non-saturation condition and a response saturation condition.

FIG. 19 illustrates a schematic diagram of a detection circuit 2000 of an impedance sensing system that includes a feature for logging a saturation condition of the response signal. In one example, detection circuit 2000 may be the detection portion of impedance sensing system 1812 of FIG. 17. Detection circuit 2000 may include, for example, a current-to-voltage (I/V) converter 2010 and an analog-to-digital (A/D) converter 2012. During an impedance measurement, an excitation signal is generated and I/V converter 2010 receives the response signal that is returned through the ground plane of the droplet actuator. I/V converter 2010 (e.g., an operational amplifier (op amp) arrangement) converts the current of the response signal to a voltage level, which feeds A/D converter 2012. A/D converter 2012 converts the voltage level to digital data and, in particular, to MAGNITUDE and PHASE data to be processed. By way of example, FIG. 20 illustrates an example of an excitation plot 2100 in relation to a response plot 2105 of an impedance sensing system. Further, response plot 2105 of FIG. 20 shows both a response non-saturation condition and a response saturation condition.

Excitation plot 2100 of FIG. 20 shows a plot of the excitation signal voltage vs. time. For example, excitation plot 2100 shows a plot of an excitation signal 2110, which is, for example, a sign wave that has a certain frequency and amplitude. Response plot 2105 of FIG. 20 shows a plot of the response signal current vs. time. For example, response plot 2105 shows a plot of a response signal 2120, which is, for example, a sign wave that has a certain frequency and amplitude. Response signal 2120 is an example of a signal at the input of I/V converter 2010. One output of A/D converter 2012 is the relative phase (ΔØ), which is the difference in phase between, for example, excitation signal 2110 of excitation plot 2100 and response signal 2120 of response plot 2105. Referring to FIG. 19, this may be called PHASE data. Another output of A/D converter 2012 is peak-to-peak amplitude of, for example, response signal 2120 of response plot 2105. Referring to FIG. 19, this may be called MAGNITUDE data.

There may be certain scenarios in which the response signal response is saturated. That is, impedance sensing system is trying to measure an admittance that is so high and an impedance that is so low that the response signal is hitting the rails of what the current sense amplifier (e.g., I/V converter 2010) can handle. For example, response signal 2120 of response plot 2105 is an example of a response signal that is in a non-saturation condition. By contrast, response plot 2105 also shows a plot of a response signal 2122, which is an example of a response signal that is in a saturation condition with respect to I/V converter 2010. For example, a V-MAX and a V-MIN voltage is associated with I/V converter 2010. Any response signal, such as response signal 2122, reaching and/or exceeding the V-MAX and/or V-MIN thresholds is in saturation (e.g., response signal 2122 shown flattened out at V-MAX and V-MIN).

This saturation condition is not always evident in the mathematical output of A/D converter 2012, which is MAGNITUDE and PHASE data. That is, the digital MAGNITUDE and PHASE data of A/D converter 2012 is not always reliable to indicate a saturation condition. Therefore, according to the invention, detection circuit 2000 includes a feature for logging a saturation condition of the response signal during any impedance detection operation.

For example, in addition to feeding the input of A/D converter 2012, the output of I/V converter 2010 feeds a pair of comparators. For example, the output of I/V converter 2010 is connected to the positive input of a comparator 2014 and to the negative input of a comparator 2016. A voltage V1 is provided at the negative input of comparator 2014. A voltage V2 is provided at the positive input of comparator 2016. V1 may be set just slightly above V-MIN and V2 may be set just slightly below V-MAX (see response plot 2105 of FIG. 20).

The outputs of comparator 2014 and comparator 2016 feed an OR gate 2018. The output of OR gate 2018 feeds a latch 2020. The output of latch 2020 provides a saturation FLAG signal. If the response signal (e.g., response signal 2122 of response plot 2105 of FIG. 20) exceeds V1 or V2, the output of at least one of comparator 2014 and comparator 2016 transitions to a logic high. This causes the output of OR gate 2018 to also go high and sets latch 2020, which means the FLAG signal is active indicating that a saturation condition is present. At beginning of any impedance detection operation latch 2020 may be reset. However, at the end of any impedance detection operation, the state of the FLAG signal is read to determine whether a saturation condition occurred. In this way, the impedance detection operation does not depend on the digital MAGNITUDE and PHASE data alone to determine whether a saturation condition has occurred.

6.2.2 Other Impedance Detection Mechanisms

Figure 21:
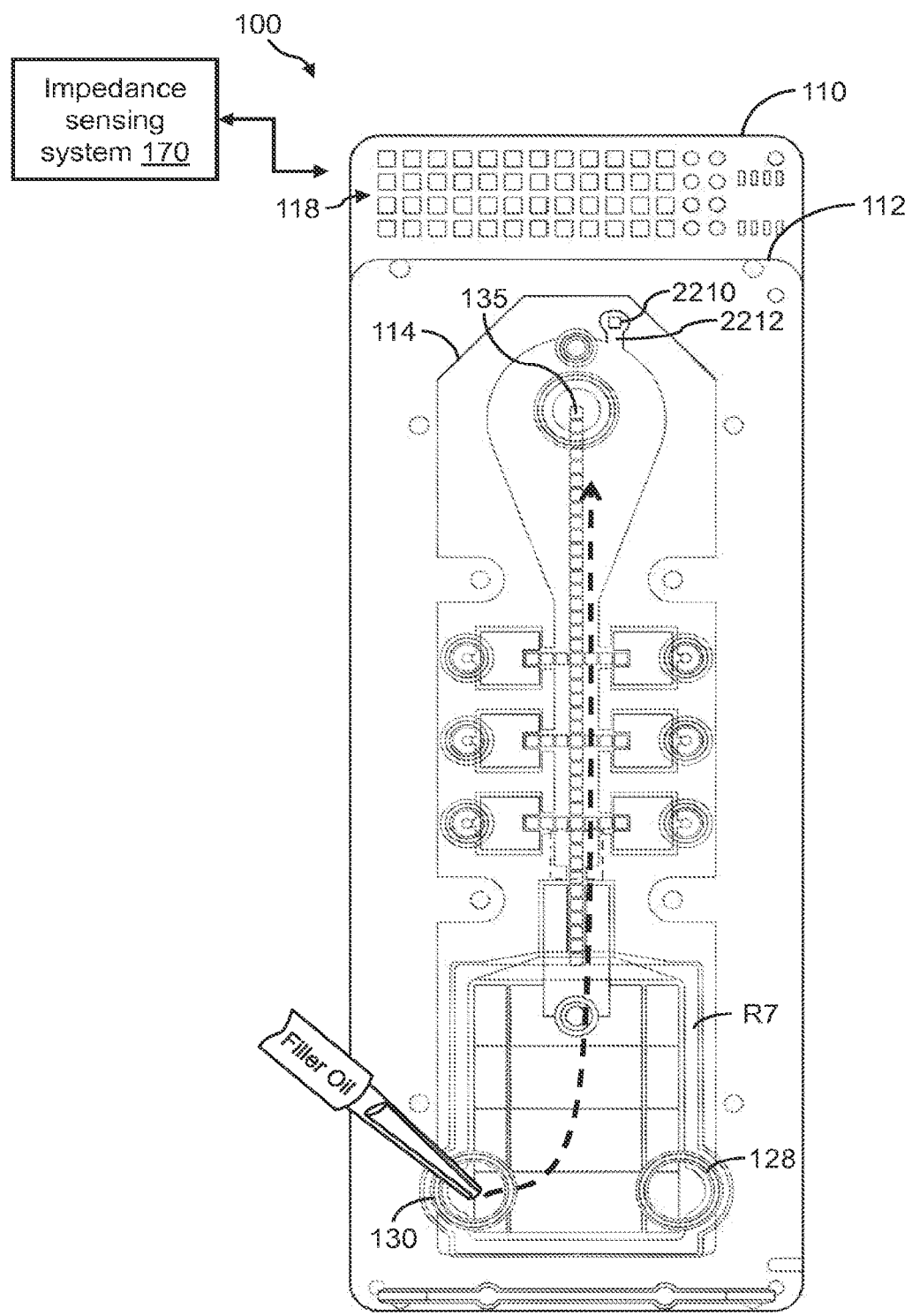
FIG. 21 illustrates a top down view of the droplet actuator of FIG. 1 that further includes an oil sensing electrode.

FIG. 21 illustrates a top down view of droplet actuator 100 of FIG. 1 that further includes an oil sensing electrode. An impedance detection operation of the oil sensing electrode may be used to verify that the gap of the droplet actuator is fully filled with filler oil. For example, patterned on the end of bottom substrate 110 that is nearest detection electrode 135 is an oil sensing electrode 2210. A fluid path 2212 that leads to oil sensing electrode 2210 is provided in gasket 114. In this way a small on-actuator fluid reservoir is created at oil sensing electrode 2210.

In operation, filler oil may be injected into the end of droplet actuator 100 that is opposite oil sensing electrode 2210. Therefore, oil sensing electrode 2210 is the last location to fill with oil. At the same time, using impedance detection, oil sensing electrode 2210 may be monitored for the presence of oil thereon. For example, filler oil may be injected into the gap of droplet actuator 100 using input port 128 and/or input port 130 of sample reservoir R7. The filler oil then flows in the direction from sample reservoir R7 to oil sensing electrode 2210 in order to fill the active area of droplet actuator 100. During the oil filling process, oil sensing electrode 2210 is monitored using, for example, impedance sensing system 170. As long the impedance measurements of impedance sensing system 170 indicate that no oil is present atop oil sensing electrode 2210, the filling process continues. However, because the small fluid reservoir at oil sensing electrode 2210 is the last location to fill with oil, as soon as the impedance measurements of impedance sensing system 170 indicate that oil is present atop oil sensing electrode 2210, the filling process is ended. The inclusion of an oil sensing electrode, such as oil sensing electrode 2210, provides a way to use impedance detection to ensure that the active area of droplet actuator 100 is fully filled with oil, according to the present invention.

Figure 22:
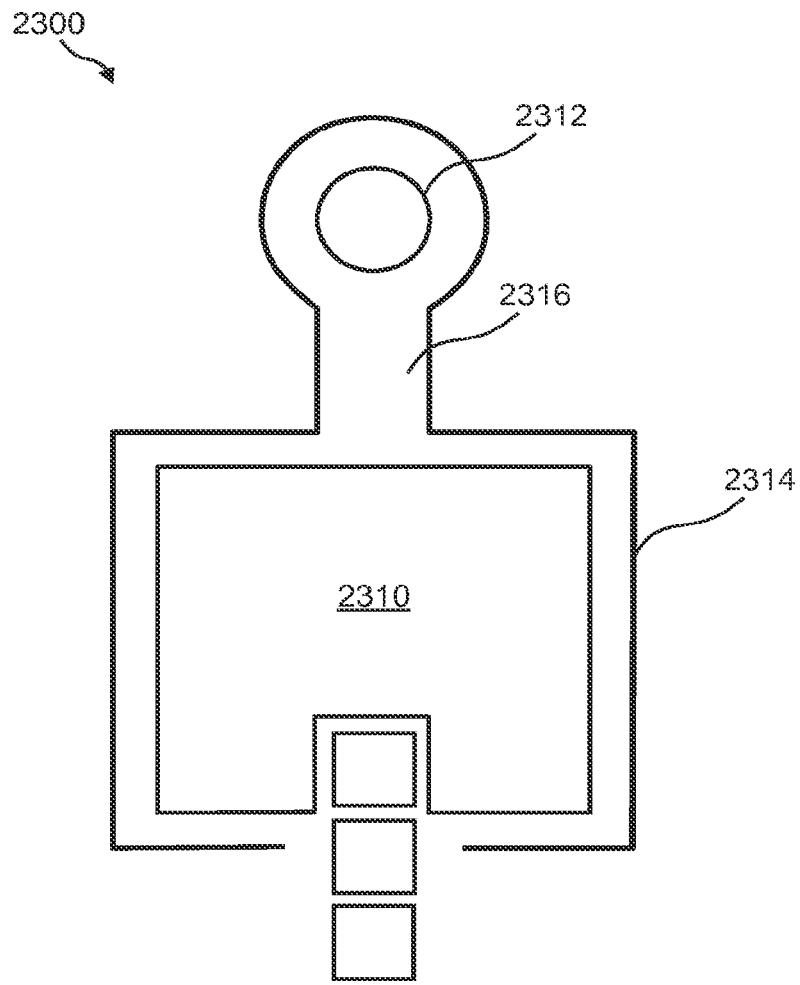
FIG. 22 illustrates a top view of a portion of a droplet actuator in which the input port of an on-actuator reservoir is not directly over any portion of the reservoir electrode.

FIG. 22 illustrates a top view of a portion of a droplet actuator 2300 in which the input port of an on-actuator reservoir is not directly over any portion of the reservoir electrode. This invention is an example of an arrangement for ensuring that a reservoir is fully loaded. In this example, droplet actuator 2300 includes a reservoir electrode 2310 that has a loading port 2312 in the top substrate (not shown) that is not directly over any portion of reservoir electrode 2310. A reservoir boundary 2314 is shown that defines the size, shape, and/or volume of the on-actuator reservoir. The reservoir boundary 2314 may be established by, for example, a gasket, features in the top substrate, features in the bottom substrate, and/or any combinations thereof. A fluid path 2316 is present from loading port 2312 to reservoir electrode 2310.

Currently, when an input port (i.e., loading opening) of an on-actuator reservoir is directly over the electrode, certain variability of the fluid volume at the reservoir may occur. This variability may be indicated by impedance measurement variability of the reservoir electrode during filling and/or use. Therefore, according to this invention, loading port 2312 is not directly over reservoir electrode 2310 and fluid path 2316 is provided by which fluid may flow to the reservoir electrode 2310 for filling. In this way, the variability of the fluid volume at the reservoir may be reduced, preferably entirely eliminated, as indicated by less impedance measurement variability during filling and/or use.

Figure 23A:
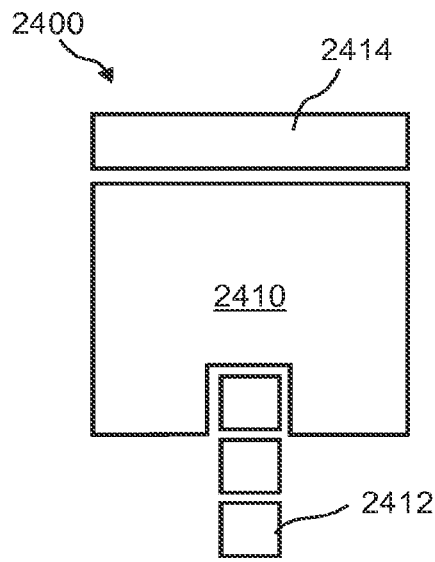
FIGS. 23A and 23B illustrate top views of two electrode arrangements, respectively, which are examples of electrode configurations for helping to detect whether a sample reservoir is fully loaded.
Figure 23B:
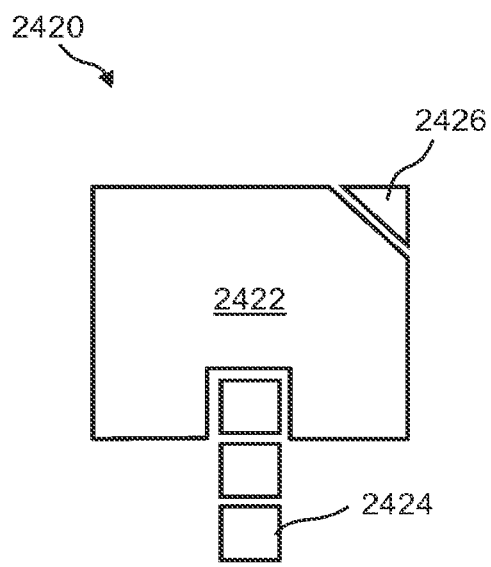

FIGS. 23A and 23B illustrate top views of an electrode arrangement 2400 and an electrode arrangement 2420, respectively, which are examples of electrode configurations for helping to detect whether a sample reservoir is fully loaded. Currently, when an on-actuator reservoir is filled, it may be difficult to determine with great accuracy the amount of fluid at the reservoir. This invention provides a separate electrode at the fringe of the primary storage reservoir for measuring impedance in order to verify that the reservoir is fully loaded (i.e., not underloaded).

In one example, electrode arrangement 2400 of FIG. 23A includes a reservoir electrode 2410. Reservoir electrode 2410 may be associated with an on-actuator reservoir. One side of reservoir electrode 2410 feeds a line, path, and/or array of droplet operations electrodes 2412 (e.g., electrowetting electrodes). An elongated impedance electrode 2414 is provided along the side of reservoir electrode 2410 that is opposite the droplet operations electrodes 2412. The impedance electrode 2414 is a separate electrode at the fringe of the primary storage reservoir. Using impedance detection, one may verify that liquid is atop impedance electrode 2414, which provides assurance that the associated reservoir is fully loaded. For example, when a certain expected impedance measurement that indicates liquid atop impedance electrode 2414 is read at impedance electrode 2414, this indicates that the reservoir is fully loaded. However, when the impedance measurement indicates little or no liquid atop impedance electrode 2414, this indicates that the reservoir may be underloaded.

In another example, electrode arrangement 2420 of FIG. 23B includes a reservoir electrode 2422. Reservoir electrode 2422 may be associated with an on-actuator reservoir. One side of reservoir electrode 2422 feeds a line, path, and/or array of droplet operations electrodes 2424 (e.g., electrowetting electrodes). In this example, a triangular-shaped impedance electrode 2426 is provided at one of the corners of reservoir electrode 2422 that is opposite the droplet operations electrodes 2424. Again, the impedance electrode 2426 is a separate electrode at the fringe of the primary storage reservoir. Using impedance detection, one may verify that liquid is atop impedance electrode 2426, which provides assurance that the associated reservoir is fully loaded. While FIGS. 23A and 23B describe examples of a single impedance electrode at one location with respect to the primary storage reservoir, FIGS. 24A, 24B, and 24C describe examples of impedance electrodes at multiple locations of the primary storage reservoir.

FIGS. 24A, 24B, and 24C illustrate top views of an electrode arrangement 2500, an electrode arrangement 2520, and an electrode arrangement 2540, respectively, which are more examples of electrode configurations for helping to detect whether a sample reservoir is fully loaded.

In one example, electrode arrangement 2500 of FIG. 24A includes a reservoir electrode 2510. Reservoir electrode 2510 may be associated with an on-actuator reservoir. One side of reservoir electrode 2510 feeds a line, path, and/or array of droplet operations electrodes 2512 (e.g., electrowetting electrodes). A U-shaped impedance electrode 2514 is provided along the three sides of reservoir electrode 2510 that do not feed droplet operations electrodes 2512. Again, the impedance electrode 2514 is a separate electrode at the fringe of the primary storage reservoir. Using impedance detection, one may verify that liquid is atop impedance electrode 2514, which provides assurance that the associated reservoir is fully loaded.

In another example, electrode arrangement 2520 of FIG. 24B includes a reservoir electrode 2522. Reservoir electrode 2522 may be associated with an on-actuator reservoir. One side of reservoir electrode 2510 feeds a line, path, and/or array of droplet operations electrodes 2524 (e.g., electrowetting electrodes). Reservoir electrode 2522 is flanked by two elongated impedance electrodes 2526 (e.g., impedance electrodes 2526a and 2525b). Again, impedance electrodes 2526a and 2525b are separate electrodes at the fringe of the primary storage reservoir. Using impedance detection, one may verify that liquid is atop impedance electrodes 2526a and 2525b, which provides assurance that the associated reservoir is fully loaded.

In yet another example, electrode arrangement 2540 of FIG. 24C includes a reservoir electrode 2542. Reservoir electrode 2542 may be associated with an on-actuator reservoir. One side of reservoir electrode 2542 feeds a line, path, and/or array of droplet operations electrodes 2544 (e.g., electrowetting electrodes). In this example, four triangular-shaped impedance electrodes 2546 (e.g., impedance electrodes 2546a, 2546b, 2546c, and 2546d) are provided at the four corners of reservoir electrode 2542. Again, impedance electrodes 2546a, 2546b, 2546c, and 2546d are separate electrodes at the fringe of the primary storage reservoir. Using impedance detection, one may verify that liquid is atop impedance electrodes 2546a, 2546b, 2546c, and 2546d, which provides assurance that the associated reservoir is fully loaded.

6.3 Systems

It will be appreciated that various aspects of the invention may be embodied as a method, system, computer readable medium, and/or computer program product. Aspects of the invention may take the form of hardware embodiments, software embodiments (including firmware, resident software, micro-code, etc.), or embodiments combining software and hardware aspects that may all generally be referred to herein as a "circuit," "module" or "system." Furthermore, the methods of the invention may take the form of a computer program product on a computer-usable storage medium having computer-usable program code embodied in the medium.

Any suitable computer useable medium may be utilized for software aspects of the invention. The computer-usable or computer-readable medium may be, for example but not limited to, an electronic, magnetic, optical, electromagnetic, infrared, or semiconductor system, apparatus, device, or propagation medium. The computer readable medium may include transitory and/or non-transitory embodiments. More specific examples (a non-exhaustive list) of the computer-readable medium would include some or all of the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a transmission medium such as those supporting the Internet or an intranet, or a magnetic storage device. Note that the computer-usable or computer-readable medium could even be paper or another suitable medium upon which the program is printed, as the program can be electronically captured, via, for instance, optical scanning of the paper or other medium, then compiled, interpreted, or otherwise processed in a suitable manner, if necessary, and then stored in a computer memory. In the context of this document, a computer-usable or computer-readable medium may be any medium that can contain, store, communicate, propagate, or transport the program for use by or in connection with the instruction execution system, apparatus, or device.

Program code for carrying out operations of the invention may be written in an object oriented programming language such as Java, Smalltalk. C++ or the like. However, the program code for carrying out operations of the invention may also be written in conventional procedural programming languages, such as the "C" programming language or similar programming languages. The program code may be executed by a processor, application specific integrated circuit (ASIC), or other component that executes the program code. The program code may be simply referred to as a software application that is stored in memory (such as the computer readable medium discussed above). The program code may cause the processor (or any processor-controlled device) to produce a graphical user interface ("GUI"). The graphical user interface may be visually produced on a display device, yet the graphical user interface may also have audible features. The program code, however, may operate in any processor-controlled device, such as a computer, server, personal digital assistant, phone, television, or any processor-controlled device utilizing the processor and/or a digital signal processor.

The program code may locally and/or remotely execute. The program code, for example, may be entirely or partially stored in local memory of the processor-controlled device. The program code, however, may also be at least partially remotely stored, accessed, and downloaded to the processor-controlled device. A user's computer, for example, may entirely execute the program code or only partly execute the program code. The program code may be a stand-alone software package that is at least partly on the user's computer and/or partly executed on a remote computer or entirely on a remote computer or server. In the latter scenario, the remote computer may be connected to the user's computer through a communications network.

The invention may be applied regardless of networking environment. The communications network may be a cable network operating in the radio-frequency domain and/or the Internet Protocol (IP) domain. The communications network, however, may also include a distributed computing network, such as the Internet (sometimes alternatively known as the "World Wide Web"), an intranet, a local-area network (LAN), and/or a wide-area network (WAN). The communications network may include coaxial cables, copper wires, fiber optic lines, and/or hybrid-coaxial lines. The communications network may even include wireless portions utilizing any portion of the electromagnetic spectrum and any signaling standard (such as the IEEE 802 family of standards, GSM/CDMA/TDMA or any cellular standard, and/or the ISM band). The communications network may even include powerline portions, in which signals are communicated via electrical wiring. The invention may be applied to any wireless/wireline communications network, regardless of physical componentry, physical configuration, or communications standard(s).

Certain aspects of invention are described with reference to various methods and method steps. It will be understood that each method step can be implemented by the program code and/or by machine instructions. The program code and/or the machine instructions may create means for implementing the functions/acts specified in the methods.

The program code may also be stored in a computer-readable memory that can direct the processor, computer, or other programmable data processing apparatus to function in a particular manner, such that the program code stored in the computer-readable memory produce or transform an article of manufacture including instruction means which implement various aspects of the method steps.

The program code may also be loaded onto a computer or other programmable data processing apparatus to cause a series of operational steps to be performed to produce a processor/computer implemented process such that the program code provides steps for implementing various functions/acts specified in the methods of the invention.

7 CONCLUDING REMARKS

The foregoing detailed description of embodiments refers to the accompanying drawings, which illustrate specific embodiments of the invention. Other embodiments having different structures and operations do not depart from the scope of the present invention. The term "the invention" or the like is used with reference to certain specific examples of the many alternative aspects or embodiments of the applicants' invention set forth in this specification, and neither its use nor its absence is intended to limit the scope of the applicants' invention or the scope of the claims. This specification is divided into sections for the convenience of the reader only. Headings should not be construed as limiting of the scope of the invention. The definitions are intended as a part of the description of the invention. It will be understood that various details of the present invention may be changed without departing from the scope of the present invention. Furthermore, the foregoing description is for the purpose of illustration only, and not for the purpose of limitation.

The invention claimed is:

1. A method, comprising:
   a. receiving an output voltage signal produced by a power supply;
   b. superimposing an excitation signal onto the output voltage signal to produce a superimposed signal;
   c. connecting the superimposed signal to one or more certain electrowetting electrodes in a droplet actuator, wherein the droplet actuator comprises:
      i. a first substrate and a second substrate separated to form a gap therebetween;
      ii. electrowetting electrodes arranged on a gap facing surface of at least one of the first substrate and second substrate; and
      iii. a filler fluid in the gap;
   d. suppressing the output voltage signal when detecting an impedance of the one or more certain electrowetting electrodes; and
   e. measuring the impedance of the one or more certain electrowetting electrodes produced by the excitation signal, wherein the impedance indicates presence of liquid at the one or more certain electrowetting electrodes.

2. The method of claim 1, wherein the filler fluid comprises an oil filler fluid.

3. The method of claim 2, wherein the oil filler fluid comprises a silicone oil.

4. The method of claim 1, wherein superimposing the excitation signal comprises adding the excitation signal to the output voltage signal.

5. The method of claim 1, wherein suppressing the output voltage signal comprises stopping the output voltage signal.

6. The method of claim 1, wherein suppressing the output voltage signal comprises disabling a switching action of the power supply.

7. The method of claim 1, wherein suppressing the output voltage signal comprises disabling the power supply.

8. The method of claim 1, further comprising receiving a suppression signal to suppress the output voltage signal from the power supply.

9. The method of claim 1, further comprising determining a saturation of the impedance.

10. The method of claim 1, further comprising:
    a. injecting the liquid into the gap of the droplet actuator; and
    b. stopping injection when the impedance indicates the liquid has flowed to the one or more certain electrowetting electrodes.

11. The method of claim 1, further comprising:
    a. injecting the liquid into a reservoir in the droplet actuator; and b. stopping injection when the impedance indicates the liquid has flowed to the one or more certain electrowetting electrodes.

12. The method of claim 1, further comprising:
a. injecting the liquid to fill a reservoir in the droplet actuator; and
b. stopping injection when the impedance indicates the liquid has flowed from the reservoir to the one or more certain electrowetting electrodes.

13. The method of claim 1, further comprising:
a. establishing a fluid path in the droplet actuator from an input port to a reservoir to the one or more certain electrowetting electrodes;
b. injecting the liquid through the input port to fill the reservoir; and
c. stopping injection when the impedance indicates the liquid has flowed to the one or more certain electrowetting electrodes.

14. The method of claim 1, further comprising:
a. arranging an input port outside a boundary of a reservoir in the droplet actuator;
b. forming a fluid path from the input port to the reservoir to the one or more certain electrowetting electrodes;
c. injecting the liquid through the input port to fill the reservoir; and
d. stopping injection when the impedance indicates the liquid has flowed to the one or more certain electrowetting electrodes.

15. A method, comprising:
a. generating an output voltage by a power supply;
b. storing charge produced by the output voltage;
c. superimposing an excitation signal onto the output voltage to produce a superimposed signal;
d. connecting the superimposed signal to one or more certain electrowetting electrodes in a droplet actuator, wherein the droplet actuator comprises:
  i. a first substrate and a second substrate separated to form a gap therebetween;
  ii. electrowetting electrodes arranged on a gap facing surface of at least one of the first substrate and second substrate; and
  iii. a filler fluid in the gap;
e. suppressing the output voltage from the power supply when detecting an impedance at the one or more certain electrowetting electrodes;
f. supplying the charge to the droplet actuator to activate the one or more certain electrowetting electrodes during the impedance; and
g. measuring the impedance produced by the excitation signal while the output voltage is suppressed, wherein the impedance indicates presence of liquid at the one or more certain electrowetting electrodes.

16. The method of claim 15, wherein the filler fluid comprises an oil filler fluid.

17. The method of claim 16, wherein the oil filler fluid comprises a silicone oil.

18. The method of claim 15, wherein superimposing the excitation signal comprises adding the excitation signal to the output voltage.

19. The method of claim 15, wherein suppressing the output voltage comprises at least one of stopping the output voltage generated by the power supply, disabling a switching action of the power supply, and disabling the power supply during the impedance measurement.

20. The method of claim 15, further comprising activating a suppression signal to suppress the output voltage generated by the power supply.

21. The method of claim 20, further comprising deactivating the suppression signal to resume the output voltage generated by the power supply.

22. The method of claim 15, further comprising charging a capacitor to store the charge.

23. The method of claim 15, further comprising determining the impedance is saturated.

24. The method of claim 15, further comprising:
a. injecting the liquid into the droplet actuator; and
b. stopping injection when the impedance indicates the liquid has flowed to the one or more certain electrowetting electrodes.

25. The method of claim 15, further comprising:
a. injecting the liquid into the gap in the droplet actuator; and
b. stopping injection into the gap when the impedance indicates the liquid has flowed to the one or more certain electrowetting electrodes.

26. The method of claim 15, further comprising:
a. injecting the liquid into a reservoir in the droplet actuator; and
b. stopping injection into the reservoir when the impedance indicates the liquid has flowed to the one or more certain electrowetting electrodes.

27. The method of claim 15, further comprising:
a. establishing a fluid path in the droplet actuator from an input port to a reservoir to the one or more certain electrowetting electrodes;
b. injecting the liquid through the input port to fill the reservoir; and
c. stopping injection when the impedance indicates the liquid has flowed to the one or more certain electrowetting electrodes.

28. The method of claim 1, further comprising:
a. arranging an input port outside a boundary of a reservoir in the droplet actuator;
b. forming a fluid path from the input port to the reservoir to the one or more certain electrowetting electrodes;
c. injecting the liquid through the input port to fill the reservoir; and
d. stopping injection when the impedance indicates the liquid has flowed to the one or more certain electrowetting electrodes.

29. A system, comprising:
a. a controller;
b. memory; and
c. the controller configured to:
  i. receive an output voltage signal;
  ii. superimpose an excitation signal onto the output voltage signal to produce a superimposed signal;
  iii. connect the superimposed signal to one or more certain electrowetting electrodes in a droplet actuator; wherein the droplet actuator comprises:
    a first substrate and a second substrate separated to form a gap therebetween;
    electrowetting electrodes arranged on a gap facing surface of at least one of the first substrate and second substrate; and
    a filler fluid in the gap;
  iv. suppress the output voltage signal when detecting an impedance of the one or more certain electrowetting electrodes; and
  v. measure the impedance of the one or more certain electrowetting electrodes produced by the excitation signal, wherein the impedance indicates presence of liquid at the one or more certain electrowetting electrodes.

30. The method of claim 29, wherein the filler fluid comprises an oil filler fluid.

31. The method of claim 30, wherein the oil filler fluid comprises a silicone oil.

32. The system of claim 29, wherein the controller is further configured to at least one of add the excitation signal to the output voltage signal, stop the output voltage signal, disable a switching action of the power supply, and disable the power supply.

33. The system of claim 29, wherein the controller is further configured to determine a saturation of the impedance.

34. The system of claim 29, wherein the controller is further configured to:
  a. cause injection of the liquid into the droplet actuator; and
  b. stop the injection when the impedance indicates the liquid has flowed to the one or more certain electrowetting electrodes.

35. The system of claim 29, wherein the controller is further configured to:
  a. cause injection of the liquid into the gap in the droplet actuator; and
  b. stop the injection when the impedance indicates the liquid has flowed to the one or more certain electrowetting electrodes.

36. The system of claim 29, wherein the controller is further configured to:
  a. cause injection of the liquid into a reservoir in the droplet actuator; and
  b. stop the injection when the impedance indicates the liquid has flowed to the one or more certain electrowetting electrodes.

37. The system of claim 29, wherein the controller is further configured to:
  a. cause the injection of the liquid to fill a reservoir in the droplet actuator; and
  b. stop the injection when the impedance indicates the liquid has flowed from the reservoir to the one or more certain electrowetting electrodes.

38. The system of claim 29, wherein the controller is further configured to:
  a. cause injection of the liquid into an input port of a reservoir in the droplet actuator; and
  b. stop the injection when the impedance indicates the liquid has flowed along a fluid path from the reservoir to the one or more certain electrowetting electrodes.

39. A non-transitory computer readable medium comprising:
  a. generating an output voltage by a power supply;
  b. storing charge produced by the output voltage;
  c. superimposing an excitation signal onto the output voltage to produce a superimposed signal;
  d. connecting the superimposed signal to one or more certain electrowetting electrodes in a droplet actuator, wherein the droplet actuator comprises:
    i. a first substrate and a second substrate separated to form a gap therebetween;
    ii. electrowetting electrodes arranged on a gap facing surface of at least one of the first substrate and second substrate; and
    iii. a filler fluid in the gap;
  e. suppressing the output voltage from the power supply when detecting an impedance at the one or more certain electrowetting electrodes;
  f. supplying the charge to the droplet actuator to activate the one or more certain electrowetting electrodes during the impedance; and
  g. measuring the impedance produced by the excitation signal while the output voltage is suppressed, wherein the impedance indicates presence of liquid at the one or more certain electrowetting electrodes.

40. The method of claim 39, wherein the filler fluid comprises an oil filler fluid.

41. The method of claim 40, wherein the oil filler fluid comprises a silicone oil.

42. The non-transitory computer readable medium of claim 39, further comprising instructions for at least one of adding the excitation signal to the output voltage, stopping the output voltage generated by the power supply, disabling a switching action of the power supply, and disabling the power supply during the impedance measurement.

43. The non-transitory computer readable medium of claim 39, further comprising instructions for activating a suppression signal to suppress the output voltage generated by the power supply.

44. The non-transitory computer readable medium of claim 43, further comprising instructions for deactivating the suppression signal to resume the output voltage generated by the power supply.

45. The non-transitory computer readable medium of claim 39, further comprising instructions for charging a capacitor to store the charge.

46. The non-transitory computer readable medium of claim 39, further comprising instructions for determining the impedance is saturated.

47. The non-transitory computer readable medium of claim 39, further comprising instructions for:
  a. injecting the liquid into the droplet actuator; and
  b. stopping injection when the impedance indicates the liquid has flowed to the one or more certain electrowetting electrodes.

48. The non-transitory computer readable medium of claim 39, further comprising instructions for:
  a. injecting the liquid into a gap in the droplet actuator; and
  b. stopping injection into the gap when the impedance indicates the liquid has flowed to the one or more certain electrowetting electrodes.

49. The non-transitory computer readable medium of claim 39, further comprising instructions for:
  a. injecting the liquid into a reservoir in the droplet actuator; and
  b. stopping injection into the reservoir when the impedance indicates the liquid has flowed to the one or more certain electrowetting electrodes.

50. The non-transitory computer readable medium of claim 39, further comprising instructions for:
  a. injecting the liquid through an input port to fill a reservoir in the droplet actuator;
  b. stopping injection when the impedance indicates the liquid has flowed to the one or more certain electrowetting electrodes.

51. The non-transitory computer readable medium of claim 39, further comprising instructions for:
  a. injecting the liquid into an input port of a reservoir in the droplet actuator; and
  b. stopping injection when the impedance indicates the liquid has flowed along a fluid path from the reservoir to the one or more certain electrowetting electrodes.

* * * * *